(12) United States Patent
Moore et al.

(10) Patent No.: US 7,582,605 B2
(45) Date of Patent: Sep. 1, 2009

(54) PHOSPHORUS-CONTAINING HEPATITIS C SERINE PROTEASE INHIBITORS

(75) Inventors: Joel D. Moore, Somerville, MA (US); Deqiang Niu, Lexington, MA (US); Guoyou Xu, Auburndale, MA (US); Dong Liu, Waltham, MA (US); Yat Sun Or, Watertown, MA (US); Zhe Wang, Hockessin, DE (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 272 days.

(21) Appl. No.: 11/503,407

(22) Filed: Aug. 11, 2006

(65) Prior Publication Data

US 2008/0039375 A1 Feb. 14, 2008

(51) Int. Cl.
*A61K 38/06* (2006.01)
*C07K 5/08* (2006.01)

(52) U.S. Cl. .......................... 514/11; 514/18; 530/331
(58) Field of Classification Search ........................ None
See application file for complete search history.

(56) References Cited

U.S. PATENT DOCUMENTS

| 6,323,180 | B1 | 11/2001 | Llinas-Brunet et al. | |
|---|---|---|---|---|
| 2005/0261200 | A1 | 11/2005 | Miao et al. | |
| 2006/0122123 | A1* | 6/2006 | Chaudhary et al. | 514/18 |

\* cited by examiner

*Primary Examiner*—Jeffrey E Russel
(74) *Attorney, Agent, or Firm*—Carolyn S. Elmore; Edgar W. Harlan; Elmore Patent Law Group P.C.

(57) ABSTRACT

The present invention relates to phosphorus-derived compounds of Formula I or Formula II, or a pharmaceutically acceptable salt, ester, or prodrug, thereof, which inhibit serine protease activity, particularly the activity of hepatitis C virus (HCV) NS3-NS4A protease. Consequently, the compounds of the present invention interfere with the life cycle of the hepatitis C virus and are also useful as antiviral agents. The present invention further relates to pharmaceutical compositions comprising the aforementioned compounds for administration to a subject suffering from HCV infection. The invention also relates to methods of treating an HCV infection in a subject by administering a pharmaceutical composition comprising the compounds of the present invention.

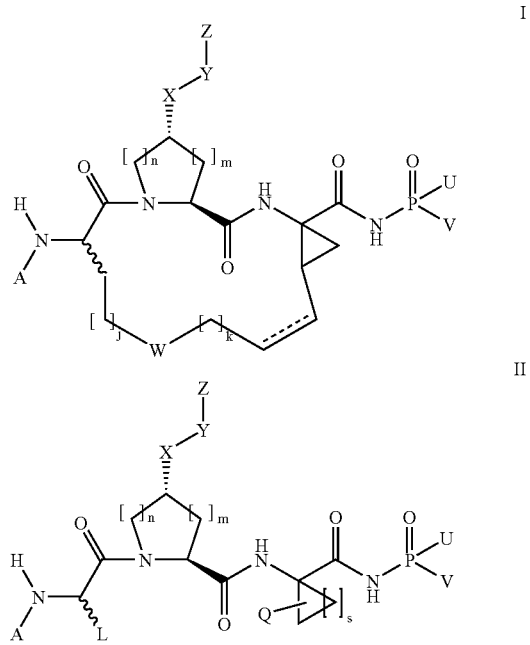

9 Claims, No Drawings

PHOSPHORUS-CONTAINING HEPATITIS C SERINE PROTEASE INHIBITORS

TECHNICAL FIELD

The present invention relates to novel hepatitis C virus (HCV) protease inhibitor compounds having antiviral activity against HCV, which are also useful in the treatment of HCV infections. More specifically, the invention relates to novel, phosphorus-containing HCV protease inhibitor compounds, compositions containing such compounds and methods for using the same, as well as processes for making such compounds.

BACKGROUND OF THE INVENTION

HCV is the principal cause of non-A, non-B hepatitis and is an increasingly severe public health problem both in the developed and developing world. It is estimated that the virus infects over 200 million people worldwide, surpassing the number of individuals infected with the human immunodeficiency virus (HIV) by nearly five fold. HCV infected patients, due to the high percentage of individuals inflicted with chronic infections, are at an elevated risk of developing cirrhosis of the liver, subsequent hepatocellular carcinoma and terminal liver disease. HCV is the most prevalent cause of hepatocellular cancer and cause of patients requiring liver transplantations in the western world.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

Only two approved therapies for HCV infection are currently available. The original treatment regimen generally involves a 3-12 month course of intravenous interferon-α (IFN-α), while a new approved second-generation treatment involves co-treatment with IFN-α and the general antiviral nucleoside mimics like ribavirin. Both of these treatments suffer from interferon related side effects as well as low efficacy against HCV infections. There exists a need for the development of effective antiviral agents for treatment of HCV infection due to the poor tolerability and disappointing efficacy of existing therapies.

In a patient population where the majority of individuals are chronically infected and asymptomatic and the prognoses are unknown, an effective drug would desirably possess significantly fewer side effects than the currently available treatments. The hepatitis C non-structural protein-3 (NS3) is a proteolytic enzyme required for processing of the viral polyprotein and consequently viral replication. Despite the huge number of viral variants associated with HCV infection, the active site of the NS3 protease remains highly conserved thus making its inhibition an attractive mode of intervention. Recent success in the treatment of HIV with protease inhibitors supports the concept that the inhibition of NS3 is a key target in the battle against HCV.

HCV is a flaviridae type RNA virus. The HCV genome is enveloped and contains a single strand RNA molecule composed of circa 9600 base pairs. It encodes a polypeptide comprised of approximately 3010 amino acids.

The HCV polyprotein is processed by viral and host peptidase into 10 discreet peptides, which serve a variety of functions. There are three structural proteins, C, E1 and E2. The P7 protein is of unknown function and is comprised of a highly variable sequence. There are six non-structural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease.

The NS4A-NS4B protease is responsible for cleaving four sites on the viral polyprotein. The NS3-NS4A cleavage is autocatalytic, occurring in cis. The remaining three hydrolyses, NS4A-NS4B, NS4B-NS5A and NS5A-NS5B all occur in trans. NS3 is a serine protease, which is structurally classified as a chymotrypsin-like protease. While the NS serine protease possesses proteolytic activity by itself, the HCV protease enzyme is not an efficient enzyme in terms of catalyzing polyprotein cleavage. It has been shown that a central hydrophobic region of the NS4A protein is required for this enhancement. The complex formation of the NS3 protein with NS4A seems necessary to the processing events, enhancing the proteolytic efficacy at all of the sites.

A general strategy for the development of antiviral agents is to inactivate virally encoded enzymes, including NS3, that are essential for the replication of the virus. Current efforts directed toward the discovery of NS3 protease inhibitors were reviewed by S. Tan, A. Pause, Y. Shi, N. Sonenberg, Hepatitis C Therapeutics: Current Status and Emerging Strategies, *Nature Rev. Drug Discov.*, 1, 867-881 (2002). Other patent disclosures describing the synthesis of HCV protease inhibitors are: WO 00/59929 (2000); WO 99/07733 (1999); WO 00/09543 (2000); WO 99/50230 (1999); U.S. Pat. No. 5,861, 297 (1999); and US2002/0037998 (2002).

SUMMARY OF THE INVENTION

The present invention relates to novel phosphorus-containing HCV protease inhibitor compounds including pharmaceutically acceptable salts, esters, or prodrugs thereof which inhibit serine protease activity, particularly the activity of hepatitis C virus (HCV) NS3-NS4A protease. Consequently, the compounds of the present invention interfere with the life cycle of the hepatitis C virus and are also useful as antiviral agents. The present invention further relates to pharmaceutical compositions comprising the aforementioned compounds for administration to a subject suffering from HCV infection. The invention also relates to methods of treating an HCV infection in a subject by administering a pharmaceutical composition comprising the compounds of the present invention.

In one embodiment of the present invention there are disclosed compounds represented by Formula I or Formula II, or pharmaceutically acceptable salts, esters, or prodrugs thereof:

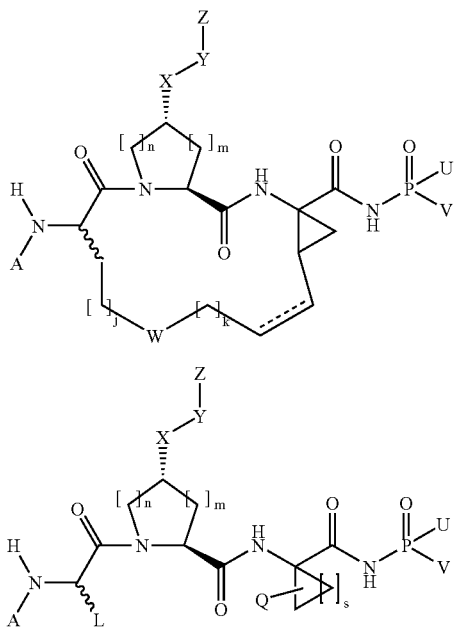

wherein
A is selected from —(C=O)—O—R₁, —(C=O)—R₂, —C(=O)—NH—R₂, and —S(O)₂—R₁, —S(O)₂NHR₂;

R₁ is selected from the group consisting of:
(i) aryl;
(ii) substituted aryl;
(iii) heteroaryl;
(iv) substituted heteroaryl;
(v) heterocycloalkyl;
(vi) substituted heterocycloalkyl;
(vii) —C₁-C₈ alkyl;
(viii) —C₂-C₈ alkenyl;
(ix) —C₂-C₈ alkynyl containing 0, 1, 2, or 3 heteroatoms selected from O, S, or N;
(x) substituted —C₁-C₈ alkyl;
(xi) substituted —C₂-C₈ alkenyl;
(xii) substituted —C₂-C₈ alkynyl containing 0, 1, 2, or 3 heteroatoms selected from O, S or N;
(xiii) —C₃-C₁₂ cycloalkyl;
(xiv) substituted —C₃-C₁₂ cycloalkyl;
(xv) —C₃-C₁₂ cycloalkenyl; and
(xvi) substituted —C₃-C₁₂ cycloalkenyl;

R₂ is selected from the group consisting of:
(i) hydrogen;
(ii) aryl;
(iii) substituted aryl;
(iv) heteroaryl;
(v) substituted heteroaryl;
(vi) heterocycloalkyl;
(vii) substituted heterocycloalkyl;
(viii) —C₁-C₈ alkyl;
(ix) —C₂-C₈ alkenyl;
(x) —C₂-C₈ alkynyl containing 0, 1, 2, or 3 heteroatoms selected from O, S, or N;
(xi) substituted —C₁-C₈ alkyl;
(xii) substituted —C₂-C₈ alkenyl;
(xiii) substituted —C₂-C₈ alkynyl containing 0, 1, 2, or 3 heteroatoms selected from O, S or N;
(xiv) —C₃-C₁₂ cycloalkyl;
(xv) substituted —C₃-C₁₂ cycloalkyl;
(xvi) —C₃-C₁₂ cycloalkenyl; and
(xvii) substituted —C₃-C₁₂ cycloalkenyl;

L is selected from the group consisting of:
(i) —C₁-C₈ alkyl;
(ii) —C₂-C₈ alkenyl;
(iii) —C₂-C₈ alkynyl containing 0, 1, 2, or 3 heteroatoms selected from O, S or N;
(iv) substituted —C₁-C₈ alkyl;
(v) substituted —C₂-C₈ alkenyl;
(vi) substituted —C₂-C₈ alkynyl containing 0, 1, 2, or 3 heteroatoms selected from O, S or N;
(vii) —C₃-C₁₂ cycloalkyl;
(viii) substituted —C₃-C₁₂ cycloalkyl;
(ix) —C₃-C₁₂ cycloalkenyl;
(x) substituted —C₃-C₁₂ cycloalkenyl;
(xi) heterocyclic;
(xii) substituted heterocyclic;
(xiii) aryl; and
(xiv) substituted aryl;

∼∼∼=a bond connected to an undefined stereogenic center;
----=either a carbon-carbon single bond or a carbon-carbon double bond X is absent or is selected from the group consisting of:
(i) O;
(ii) S; and
(iii) NR₃;

R₃ is selected from the group consisting of:
(i) hydrogen;
(ii) aryl;
(iii) substituted aryl;
(iv) heteroaryl;
(v) substituted heteroaryl;
(vi) heterocycloalkyl;
(vii) substituted heterocycloalkyl;
(viii) —C₁-C₈ alkyl;
(ix) —C₂-C₈ alkenyl;
(x) —C₂-C₈ alkynyl containing 0, 1, 2, or 3 heteroatoms selected from O, S, or N;
(xi) substituted —C₁-C₈ alkyl;
(xii) substituted —C₂-C₈ alkenyl;
(xiii) substituted —C₂-C₈ alkynyl containing 0, 1, 2, or 3 heteroatoms selected from O, S or N;
(xiv) —C₃-C₁₂ cycloalkyl;
(xv) substituted —C₃-C₁₂ cycloalkyl;
(xvi) —C₃-C₁₂ cycloalkenyl; and
(xvii) substituted —C₃-C₁₂ cycloalkenyl;

Y is absent or is selected from the group consisting of:
(i) —C₁-C₆ alkyl containing 0, 1, 2, or 3 heteroatoms selected from O, S, or N, optionally substituted with one or more substituent selected from halogen, aryl, substituted aryl, heteroaryl, or substituted heteroaryl;
(ii) —C₂-C₆ alkenyl containing 0, 1, 2, or 3 heteroatoms selected from O, S, or N, optionally substituted with one or more substituent selected from halogen, aryl, substituted aryl, heteroaryl, or substituted heteroaryl;
(iii) —C₂-C₆ alkynyl containing 0, 1, 2, or 3 heteroatoms selected from O, S, or N, optionally substituted with one or more substituent selected from halogen, aryl, substituted aryl, heteroaryl, or substituted heteroaryl; and
(iv) —C₃-C₁₂ cycloalkyl, substituted —C₃-C₁₂ cycloalkyl, heterocycloalkyl, substituted heterocycloalkyl;

Z is selected from aryl, substituted aryl, heteroaryl, and substituted heteroaryl;
Q is selected from the group consisting of:
(i) hydrogen;
(ii) $SR_4$;
(iii) —$C_1$-$C_8$ alkyl;
(iv) —$C_2$-$C_8$ alkenyl;
(v) —$C_2$-$C_8$ alkynyl containing 0, 1, 2, or 3 heteroatoms selected from O, S or N;
(vi) substituted —$C_1$-$C_8$ alkyl;
(vii) substituted —$C_2$-$C_8$ alkenyl;
(viii) substituted —$C_2$-$C_8$ alkynyl containing 0, 1, 2, or 3 heteroatoms selected from O, S or N;
(ix) —$C_3$-$C_{12}$ cycloalkyl;
(x) substituted —$C_3$-$C_{12}$ cycloalkyl;
(xi) —$C_3$-$C_{12}$ cycloalkenyl;
(xii) substituted —$C_3$-$C_{12}$ cycloalkenyl;
(xiii) heterocyclic; and
(xiv) substituted heterocyclic
$R_4$ is selected from:
(i) aryl;
(ii) substituted aryl;
(iii) heteroaryl;
(iv) substituted heteroaryl;
(v) heterocycloalkyl;
(vi) substituted heterocycloalkyl;
(vii) —$C_1$-$C_8$ alkyl;
(viii) —$C_2$-$C_8$ alkenyl;
(ix) —$C_2$-$C_8$ alkynyl containing 0, 1, 2, or 3 heteroatoms selected from O, S, or N;
(x) substituted —$C_1$-$C_8$ alkyl;
(xi) substituted —$C_2$-$C_8$ alkenyl;
(xii) substituted —$C_2$-$C_8$ alkynyl containing 0, 1, 2, or 3 heteroatoms selected from O, S or N;
(xiii) —$C_3$-$C_{12}$ cycloalkyl;
(xiv) substituted —$C_3$-$C_{12}$ cycloalkyl;
(xv) —$C_3$-$C_{12}$ cycloalkenyl; and
(xvi) substituted —$C_3$-$C_{12}$ cycloalkenyl;
W is selected from —$CH_2$—, —O—, —S—, —$S(O)_2$—, —CO—, —C(O)O—, —C(O)NH—, —CHF—, —$CF_2$—, aryl, substituted aryl, heteroaryl, and substituted heteroaryl;
U and V are independently chosen from the following groups:
(i) $R_5$; and
(ii) $XR_6$ where X is as previously defined; or, in the alternative, U and V taken together with the phosphorus atom to which they are attached form a phosphorus-derived heterocyclic moiety;
$R_5$ is selected from the group consisting of:
(i) aryl;
(ii) substituted aryl;
(iii) heteroaryl;
(iv) substituted heteroaryl;
(v) heterocycloalkyl;
(vi) substituted heterocycloalkyl;
(vii) —$C_1$-$C_8$ alkyl;
(viii) —$C_2$-$C_8$ alkenyl;
(ix) —$C_2$-$C_8$ alkynyl containing 0, 1, 2, or 3 heteroatoms selected from O, S, or N;
(x) substituted —$C_1$-$C_8$ alkyl;
(xi) substituted —$C_2$-$C_8$ alkenyl;
(xii) substituted —$C_2$-$C_8$ alkynyl containing 0, 1, 2, or 3 heteroatoms selected from O, S or N;
(xiii) —$C_3$-$C_{12}$ cycloalkyl;
(xiv) substituted —$C_3$-$C_{12}$ cycloalkyl;
(xv) —$C_3$-$C_{12}$ cycloalkenyl; and
(xvi) substituted —$C_3$-$C_{12}$ cycloalkenyl;
$R_6$ is selected from the group consisting of:
(i) hydrogen;
(ii) aryl;
(iii) substituted aryl;
(iv) heteroaryl;
(v) substituted heteroaryl;
(vi) heterocycloalkyl;
(vii) substituted heterocycloalkyl;
(viii) —$C_1$-$C_8$ alkyl;
(ix) —$C_2$-$C_8$ alkenyl;
(x) —$C_2$-$C_8$ alkynyl containing 0, 1, 2, or 3 heteroatoms selected from O, S, or N;
(xi) substituted —$C_1$-$C_8$ alkyl;
(xii) substituted —$C_2$-$C_8$ alkenyl;
(xiii) substituted —$C_2$-$C_8$ alkynyl containing 0, 1, 2, or 3 heteroatoms selected from O, S or N;
(xiv) —$C_3$-$C_{12}$ cycloalkyl;
(xv) substituted —$C_3$-$C_{12}$ cycloalkyl;
(xvi) —$C_3$-$C_{12}$ cycloalkenyl; and
(xvii) substituted —$C_3$-$C_{12}$ cycloalkenyl;
j=0, 1, 2, 3, or 4;
k=1, 2, or 3;
s=0, 1, 2, or 3;
m=0, 1, or 2;
n=1, 2, or 3;

DETAILED DESCRIPTION OF THE INVENTION

A first embodiment of the invention is a compound represented by either Formula I or Formula II, as described above, or a pharmaceutically acceptable salt, ester or prodrug thereof, alone or in combination with a pharmaceutically acceptable carrier or excipient.

Representative subgenera of the invention include, but are not limited to compounds of Formula III or Formula IV:

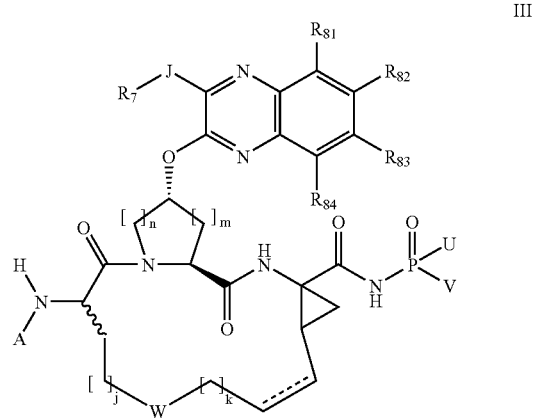

-continued

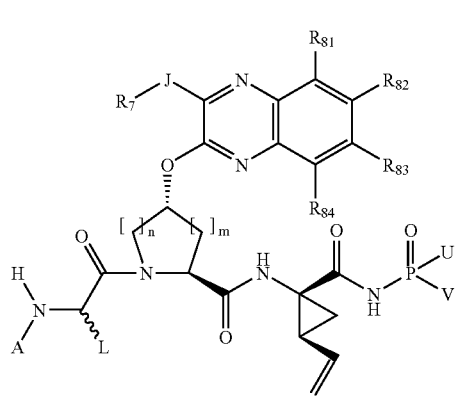

IV wherein A, L, j, k, m, n, W, U, and V are all as previously defined;

J is either absent or =O, S, NR$_5$, CO, (CO)NR$_5$, (CO)O, NR$_5$(CO), NH(CO)NH, NR$_5$SO$_2$, wherein R$_5$ is as previously defined R$_7$ is selected from aryl, substituted aryl, heteroaryl, and substituted heteroaryl;

R$_{81}$, R$_{82}$, R$_{83}$, and R$_{84}$ are independently chosen from:
(i) hydrogen;
(ii) halogen;
(iii) —NO$_2$;
(iv) —CN;
(v) MR$_9$, wherein M is absent, or =O, S, NR$_3$R$_6$, wherein R$_3$ and R$_6$ are as previously defined;
(vi) aryl;
(vii) substituted aryl;
(viii) heteroaryl;
(ix) substituted heteroaryl;
(x) heterocycloalkyl; and
(xi) substituted heterocycloalkyl;

R$_9$ is selected from the group consisting of:
(i) hydrogen;
(ii) aryl;
(iii) substituted aryl;
(iv) heteroaryl;
(v) substituted heteroaryl;
(vi) heterocycloalkyl;
(vii) substituted heterocycloalkyl;
(viii) —C$_1$-C$_8$ alkyl;
(ix) —C$_2$-C$_8$ alkenyl;
(x) —C$_2$-C$_8$ alkynyl containing 0, 1, 2, or 3 heteroatoms selected from O, S, or N;
(xi) substituted —C$_1$-C$_8$ alkyl;
(xii) substituted —C$_2$-C$_8$ alkenyl; and
(xiii) substituted —C$_2$-C$_8$ alkynyl containing 0, 1, 2, or 3 heteroatoms selected from O, S or N;

Representative subgenera of the invention also include, but are not limited to compounds of Formula V or Formula VI:

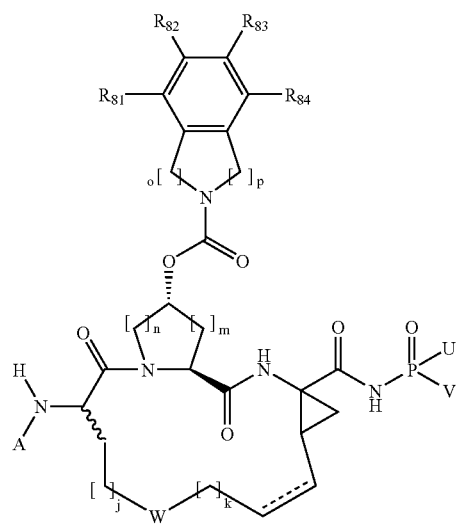

V

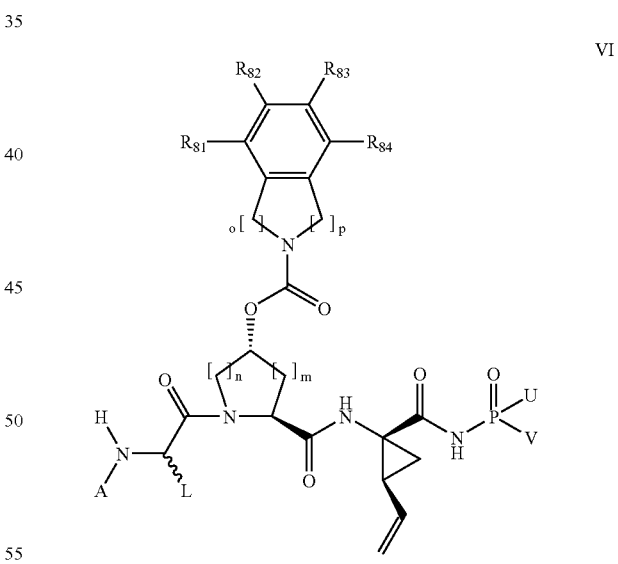

VI wherein A, L, j, k, m, n, W, U, V, R$_{81}$, R$_{82}$, R$_{83}$, and R$_{84}$ are all as previously defined;
o=1, 2, or 3
p=1, 2, or 3

Representative compounds of the invention include, but are not limited to, compounds 1-113 of Formula VII:

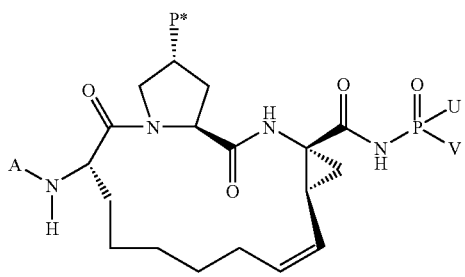

Wherein A, P* and

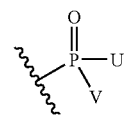

are delineated for each compound as set forth in Table 1

TABLE 1

| CPD# | A | P* | (V)-) |
|---|---|---|---|
| 1 | cyclopentyl-O-C(=O)- | 2-thienyl-quinoxalin-3-yloxy | P(=O)(Ph)(Ph) |
| 2 | cyclopentyl-O-C(=O)- | 2-thienyl-quinoxalin-3-yloxy | P(=O)(OPh)(OPh) |
| 3 | cyclopentyl-O-C(=O)- | 2-thienyl-quinoxalin-3-yloxy | P(=O)(OEt)(OEt) |
| 4 | tert-butyl-O-C(=O)- | isoindolin-2-yl-C(=O)-O- | P(=O)(Ph)(Ph) |

TABLE 1-continued

| CPD# | A | P* | (O=P(U)(V)-) |
|---|---|---|---|
| 5 | thiophene-2-sulfonyl | 3-(thiophen-2-yl)quinoxalin-2-yloxy | P(=O)Ph₂ |
| 6 | N-cyclopentylsulfamoyl | 3-(thiophen-2-yl)quinoxalin-2-yloxy | P(=O)Ph₂ |
| 7 | tert-butoxycarbonyl | 4-fluoroisoindoline-2-carbonyloxy | P(=O)(OMe)₂ |
| 8 | cyclopentyloxycarbonyl | 4-fluoroisoindoline-2-carbonyloxy | P(=O)Ph₂ |
| 9 | cyclobutyloxycarbonyl | 4-fluoroisoindoline-2-carbonyloxy | P(=O)Ph₂ |
| 10 | cyclopentylaminocarbonyl | 4-fluoroisoindoline-2-carbonyloxy | P(=O)Ph₂ |

TABLE 1-continued

| CPD# | A | P* | (phosphoryl group with U, V) |
|------|---|-----|------|
| 11 | thiophene-2-sulfonyl | 4-fluoroisoindoline-2-carbonyloxy | P(=O)(Ph)(Ph) |
| 12 | cyclopentylaminosulfonyl | 4-fluoroisoindoline-2-carbonyloxy | P(=O)(Ph)(Ph) |
| 13 | tert-butoxycarbonyl | 3-(thiophen-2-yl)quinoxalin-2-yloxy | P(=O)(OEt)(OEt) |
| 14 | cyclopentyloxycarbonyl | 3-(thiophen-2-yl)quinoxalin-2-yloxy | P(=O)(OBn)(OBn) |
| 15 | cyclobutyloxycarbonyl | 3-(thiophen-2-yl)quinoxalin-2-yloxy | P(=O)(OEt)(OEt) |
| 16 | cyclopentylaminocarbonyl | 3-(thiophen-2-yl)quinoxalin-2-yloxy | P(=O)(OEt)(OEt) |

TABLE 1-continued
| CPD# | A | P* | 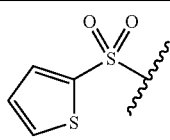 |
|---|---|---|---|
| 17 | 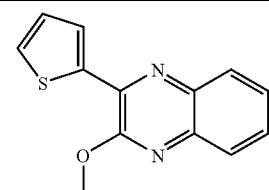 | 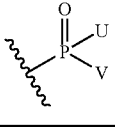 | 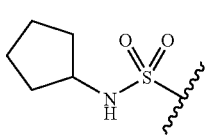 |
| 18 | 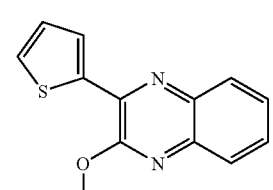 | 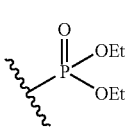 | 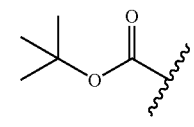 |
| 19 | 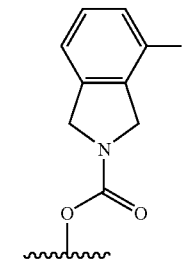 | 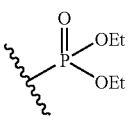 | 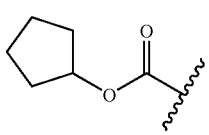 |
| 20 | 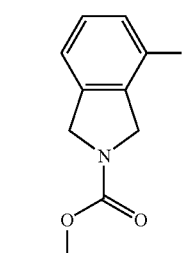 | 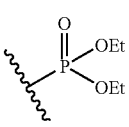 | 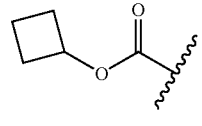 |
| 21 | 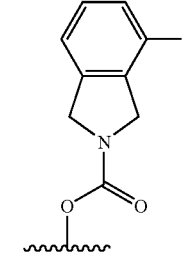 | 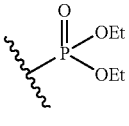 | 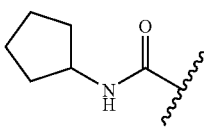 |
| 22 | 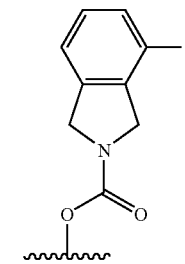 | 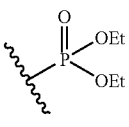 | |

TABLE 1-continued
| CPD# | A | P* | 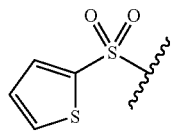 |
|---|---|---|---|
| 23 | 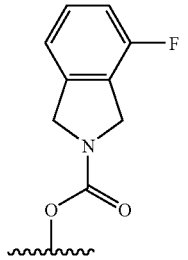 | 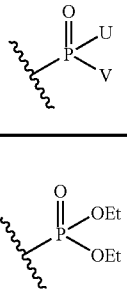 | 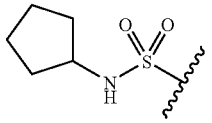 |
| 24 | 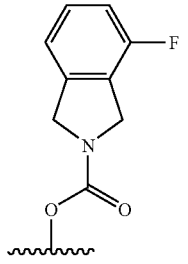 | 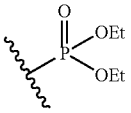 | 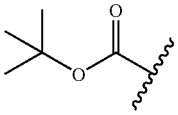 |
| 25 | 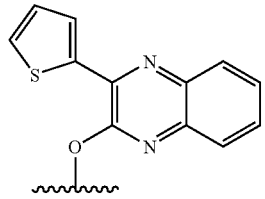 | 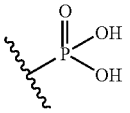 | 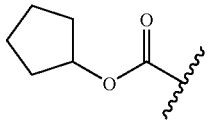 |
| 26 | 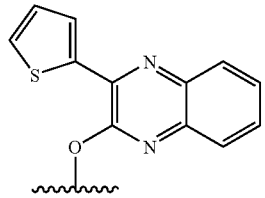 | 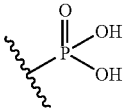 | 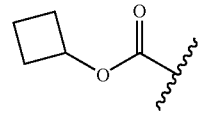 |
| 27 | 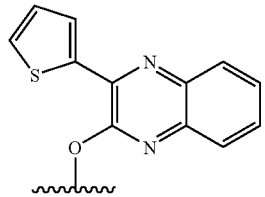 | 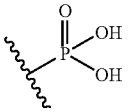 | 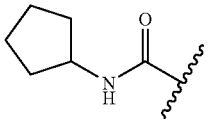 |
| 28 | 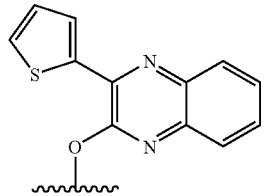 | 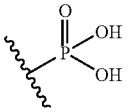 | |

TABLE 1-continued

| CPD# | A | P* | (phosphonate group) |
|---|---|---|---|
| 29 | thiophene-2-sulfonyl | 3-(thiophen-2-yl)quinoxalin-2-yloxy | P(=O)(OH)(OH) |
| 30 | N-cyclopentylsulfamoyl | 3-(thiophen-2-yl)quinoxalin-2-yloxy | P(=O)(OH)(OH) |
| 31 | tert-butoxycarbonyl | 4-fluoroisoindoline-2-carbonyloxy | P(=O)(OH)(OH) |
| 32 | cyclopentyloxycarbonyl | 4-fluoroisoindoline-2-carbonyloxy | P(=O)(OH)(OH) |
| 33 | cyclobutyloxycarbonyl | 4-fluoroisoindoline-2-carbonyloxy | P(=O)(OH)(OH) |
| 34 | N-cyclopentylcarbamoyl | 4-fluoroisoindoline-2-carbonyloxy | P(=O)(OH)(OH) |

TABLE 1-continued

| CPD# | A | P* | (O=P(U)(V)) |
|---|---|---|---|
| 35 | thiophene-2-sulfonyl | 4-fluoro-isoindoline-2-carboxylate (O-linked) | P(=O)(OH)(OH) |
| 36 | cyclopentyl-NH-SO2- | 4-fluoro-isoindoline-2-carboxylate (O-linked) | P(=O)(OH)(OH) |
| 37 | tert-butyl ester | 3-(thiophen-2-yl)quinoxalin-2-yloxy | P(=O)(OPh)(OPh) |
| 38 | cyclopentyl ester | 3-(thiophen-2-yl)quinoxalin-2-yloxy | P(=O)(OMe)(OMe) |
| 39 | cyclobutyl ester | 3-(thiophen-2-yl)quinoxalin-2-yloxy | P(=O)(OPh)(OPh) |
| 40 | cyclopentyl amide | 3-(thiophen-2-yl)quinoxalin-2-yloxy | P(=O)(OPh)(OPh) |

TABLE 1-continued

| CPD# | A | P* | (phosphonate group) |
|---|---|---|---|
| 41 | thiophene-2-sulfonyl | 3-(thiophen-2-yl)quinoxalin-2-yloxy | P(=O)(OPh)(OPh) |
| 42 | N-cyclopentylsulfamoyl | 3-(thiophen-2-yl)quinoxalin-2-yloxy | P(=O)(OPh)(OPh) |
| 43 | tert-butoxycarbonyl | 4-fluoroisoindoline-2-carbonyloxy | P(=O)(OPh)(OPh) |
| 44 | cyclopentyloxycarbonyl | 4-fluoroisoindoline-2-carbonyloxy | P(=O)(OPh)(OPh) |
| 45 | cyclobutyloxycarbonyl | 4-fluoroisoindoline-2-carbonyloxy | P(=O)(OPh)(OPh) |
| 46 | N-cyclopentylcarbamoyl | 4-fluoroisoindoline-2-carbonyloxy | P(=O)(OPh)(OPh) |

TABLE 1-continued
| CPD# | A | P* | 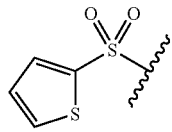 |
|---|---|---|---|
| 47 | 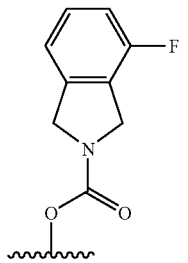 | 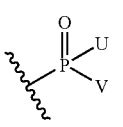 | 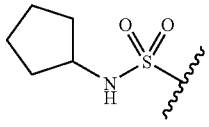 |
| 48 | 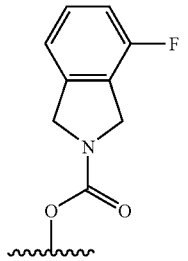 | 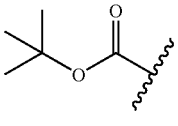 | 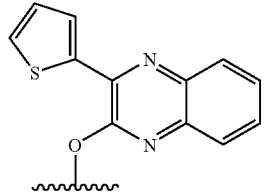 |
| 49 | 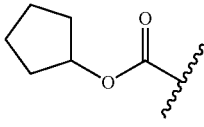 | 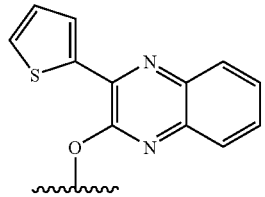 | 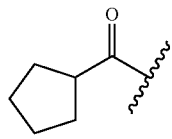 |
| 50 | 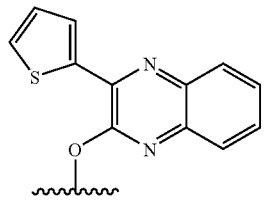 | 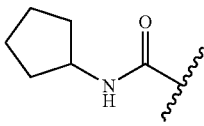 | 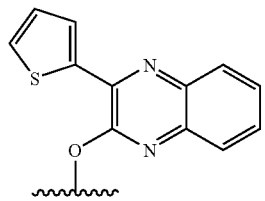 |
| 51 | | | |
| 52 | | | |

TABLE 1-continued

| CPD# | A | P* | (phosphine oxide group) |
|---|---|---|---|
| 53 | thiophene-2-sulfonyl | 3-(thiophen-2-yl)quinoxalin-2-yloxy | P(=O)(CH₃)(CH₃) |
| 54 | N-cyclopentylsulfamoyl | 3-(thiophen-2-yl)quinoxalin-2-yloxy | P(=O)(CH₃)(CH₃) |
| 55 | tert-butoxycarbonyl | (4-fluoroisoindolin-2-yl)carbonyloxy | P(=O)(CH₃)(CH₃) |
| 56 | cyclopentyloxycarbonyl | (4-fluoroisoindolin-2-yl)carbonyloxy | P(=O)(CH₃)(CH₃) |
| 57 | cyclopentylcarbonyl | (4-fluoroisoindolin-2-yl)carbonyloxy | P(=O)(CH₃)(CH₃) |
| 58 | N-cyclopentylcarbamoyl | (4-fluoroisoindolin-2-yl)carbonyloxy | P(=O)(CH₃)(CH₃) |

TABLE 1-continued
| CPD# | A | P* | 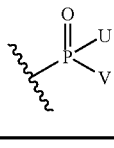 |
|---|---|---|---|
59
60
61
62
63
64

TABLE 1-continued

| CPD# | A | P* | (phosphonate group) |
|------|---|----|----|
| 65 | 2-thienylsulfonyl | 3-(thien-2-yl)quinoxalin-2-yloxy | diisopropyl phosphonate |
| 66 | N-cyclopentylsulfamoyl | 3-(thien-2-yl)quinoxalin-2-yloxy | diisopropyl phosphonate |
| 67 | tert-butoxycarbonyl | 4-fluoro-isoindoline-2-carbonyloxy | diisopropyl phosphonate |
| 68 | cyclopentyloxycarbonyl | 4-fluoro-isoindoline-2-carbonyloxy | diisopropyl phosphonate |
| 69 | cyclopentylcarbonyl | 4-fluoro-isoindoline-2-carbonyloxy | diisopropyl phosphonate |
| 70 | N-cyclopentylcarbamoyl | 4-fluoro-isoindoline-2-carbonyloxy | diisopropyl phosphonate |

TABLE 1-continued
| CPD# | A | P* | 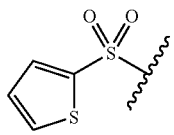 |
|------|---|----|----|
| 71 | 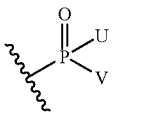 | 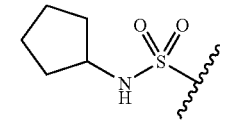 | 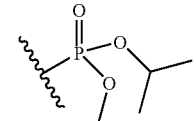 |
| 72 | 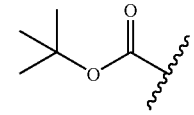 | 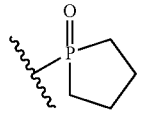 | 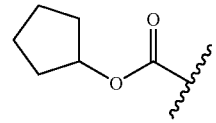 |
| 73 | 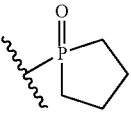 | 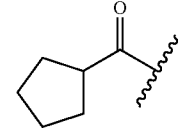 | 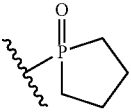 |
| 74 | 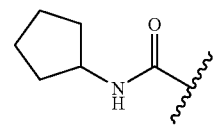 | 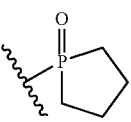 | |
| 75 | | | |
| 76 | | | |

TABLE 1-continued
| CPD# | A | P* | (phosphine oxide group) |
|---|---|---|---|
| 77 | 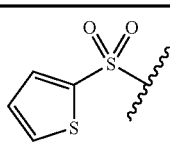 | 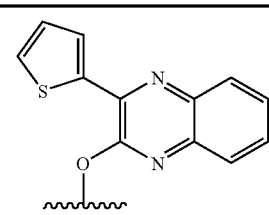 | 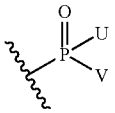 |
| 78 | 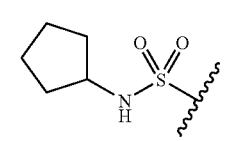 | 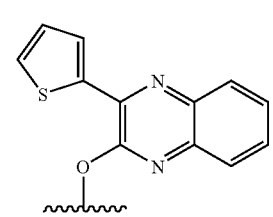 | 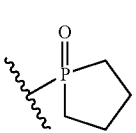 |
| 79 | 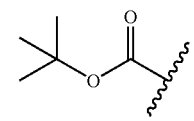 | 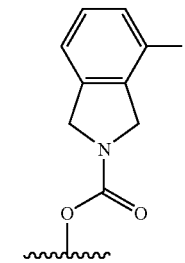 | 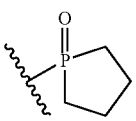 |
| 80 | 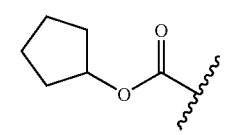 | 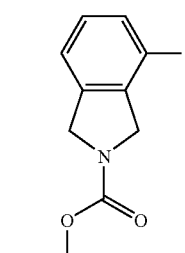 | 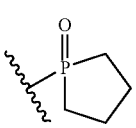 |
| 81 | 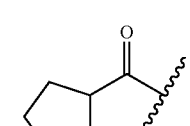 | 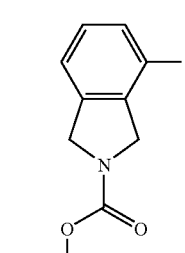 | 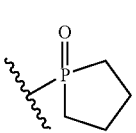 |
| 82 | 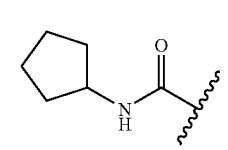 | 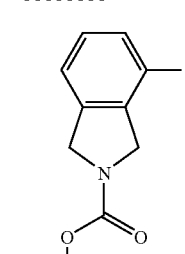 | 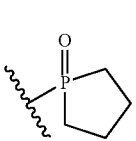 |

TABLE 1-continued

| CPD# | A | P* | (phosphorus group with U, V) |
|---|---|---|---|
| 83 | | | |
| 84 | | | |
| 85 | | | |
| 86 | | | |
| 87 | | | |
| 88 | | | |

TABLE 1-continued

| CPD# | A | P* | (phosphonate group) |
|------|---|----|----|
| 89 | 2-thienylsulfonyl | 3-(2-thienyl)quinoxalin-2-yloxy | cyclopentyl phosphonate, O-cyclopentyl |
| 90 | N-cyclopentylsulfamoyl | 3-(2-thienyl)quinoxalin-2-yloxy | cyclopentyl phosphonate, O-cyclopentyl |
| 91 | tert-butoxycarbonyl | 4-fluoroisoindolin-2-ylcarbonyloxy | cyclopentyl phosphonate, O-cyclopentyl |
| 92 | cyclopentyloxycarbonyl | 4-fluoroisoindolin-2-ylcarbonyloxy | cyclopentyl phosphonate, O-cyclopentyl |
| 93 | cyclopentylcarbonyl | 4-fluoroisoindolin-2-ylcarbonyloxy | cyclopentyl phosphonate, O-cyclopentyl |
| 94 | N-cyclopentylcarbamoyl | 4-fluoroisoindolin-2-ylcarbonyloxy | cyclopentyl phosphonate, O-cyclopentyl |

TABLE 1-continued
| CPD# | A | P* | 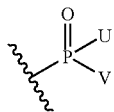 |
|---|---|---|---|
95, 96, 97, 98, 99, 100

TABLE 1-continued
| CPD# | A | P* | |
|------|---|----|---|
| 101 | 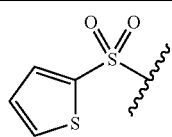 | 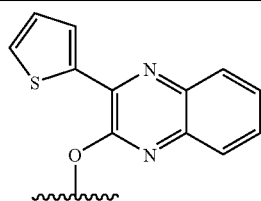 | 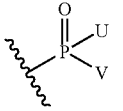 |
| 102 | 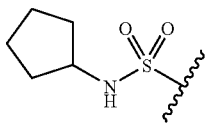 | 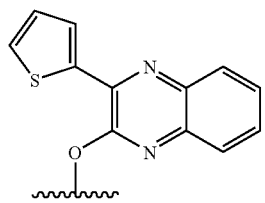 | 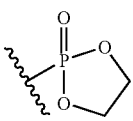 |
| 103 | 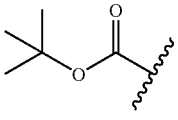 | 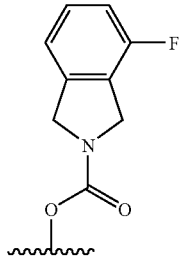 | 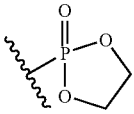 |
| 104 | 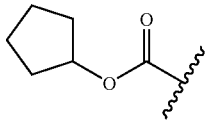 | 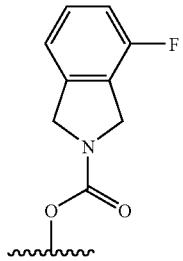 | 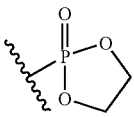 |
| 105 | 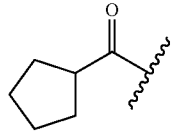 | 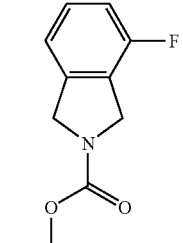 | 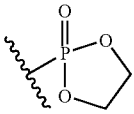 |
| 106 | 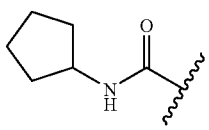 | 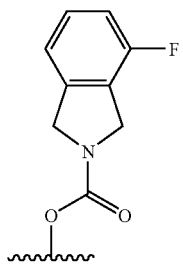 | 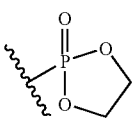 |

TABLE 1-continued

| CPD# | A | P* | (O=P(U)(V)-) |
|------|---|----|----|
| 107 | thiophene-2-sulfonyl | 4-fluoroisoindoline-2-carboxylate (O-linked) | 1,3,2-dioxaphospholane 2-oxide |
| 108 | cyclopentylaminosulfonyl | 4-fluoroisoindoline-2-carboxylate (O-linked) | 1,3,2-dioxaphospholane 2-oxide |
| 109 | cyclopentyl ester | 2-(2-(isopropylamino)thiazol-4-yl)-7-methoxyquinolin-4-yloxy | P(=O)Ph₂ |
| 110 | cyclopentyl ester | 3-(2-(thiophen-3-yl)vinyl)quinoxalin-2-yloxy | P(=O)Ph₂ |
| 111 | cyclopentyl ester | 7-methoxy-2-phenylquinolin-4-yloxy | P(=O)Ph₂ |

TABLE 1-continued

| CPD# | A | P* | |
|---|---|---|---|
| 112 | cyclopentyl ester | 5,6-dimethyl-benzotriazol-2-yl | P(=O)Ph₂ |
| 113 | cyclopentyl ester | 2-(4-methoxyphenyl)tetrazol-5-yl | P(=O)Ph₂ |

Representative compounds of the invention also include, but are not limited to, compounds 114—of Formula VIII:

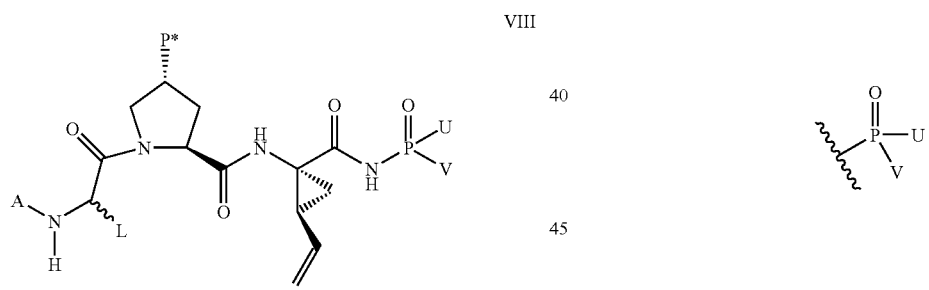

Wherein A, P*, and L are set forth for each compound in Table 2:

TABLE 2

| Cpd# | A | P* | P(=O)UV | L |
|---|---|---|---|---|
| 114 | t-butyl ester | 3-(thien-2-yl)quinoxalin-2-yloxy | P(=O)Ph₂ | t-butyl |

TABLE 2-continued
| Cpd# | A | P* | 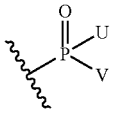 | L |
|---|---|---|---|---|
| 115 | 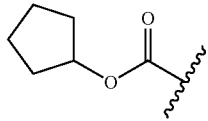 | 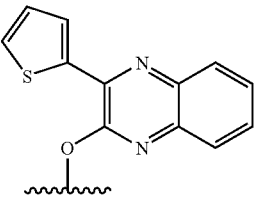 | 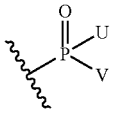 |  |
| 116 | 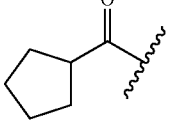 | 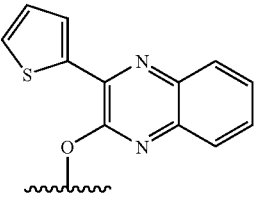 | 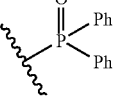 | 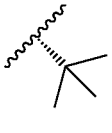 |
| 117 | 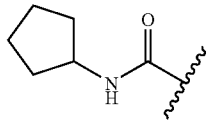 | 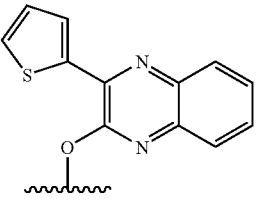 | 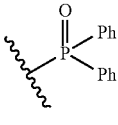 |  |
| 118 | 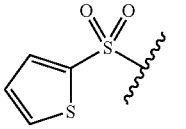 | 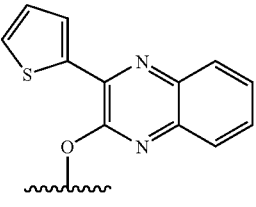 | 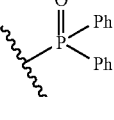 | 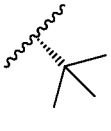 |
| 119 | 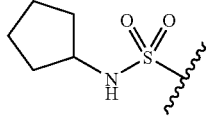 | 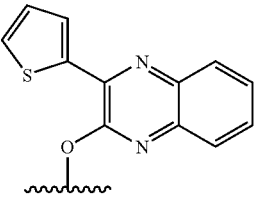 | 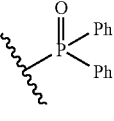 | 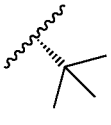 |
| 120 | 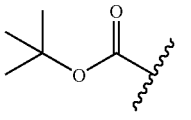 | 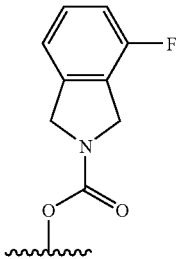 | 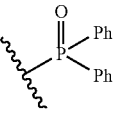 | 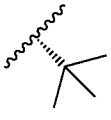 |

TABLE 2-continued
| Cpd# | A | P* | 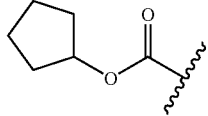 | L |
|---|---|---|---|---|
| 121 | 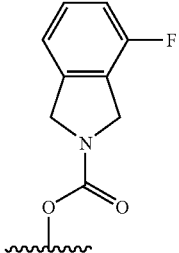 | 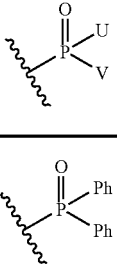 | 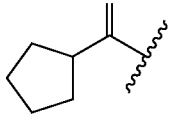 | 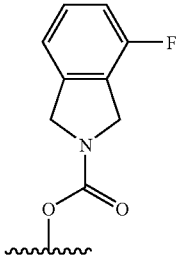 |
| 122 | 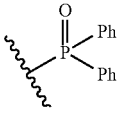 | 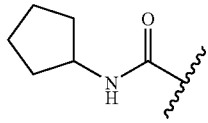 | 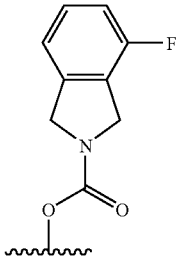 | 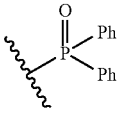 |
| 123 | 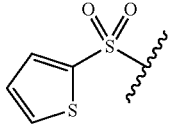 | 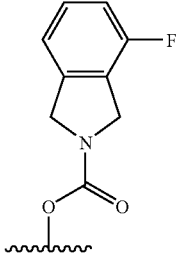 | 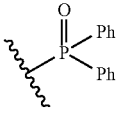 | 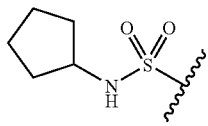 |
| 124 | 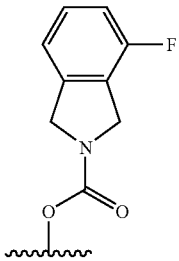 | | | |
| 125 | 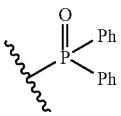 | | | |

TABLE 2-continued

| Cpd# | A | P* | $\begin{array}{c}O\\\|\\-P-U\\\|\\V\end{array}$ | L |
|---|---|---|---|---|
| 126 | tert-butyl ester group | 2-thienyl-quinoxalinyloxy | P(O)(OEt)₂ | tert-butyl |
| 127 | cyclopentyl ester group | 2-thienyl-quinoxalinyloxy | P(O)(OEt)₂ | tert-butyl |
| 128 | cyclopentyl ketone group | 2-thienyl-quinoxalinyloxy | P(O)(OEt)₂ | tert-butyl |
| 129 | cyclopentyl amide group | 2-thienyl-quinoxalinyloxy | P(O)(OEt)₂ | tert-butyl |
| 130 | 2-thienylsulfonyl group | 2-thienyl-quinoxalinyloxy | P(O)(OEt)₂ | tert-butyl |
| 131 | cyclopentyl sulfonamide group | 2-thienyl-quinoxalinyloxy | P(O)(OEt)₂ | tert-butyl |

TABLE 2-continued

| Cpd# | A | P* | (phosphonate) | L |
|---|---|---|---|---|
| 132 | tert-butyl ester | 4-F isoindoline carbamate | P(O)(OEt)₂ | tert-butyl |
| 133 | cyclopentyl ester | 4-F isoindoline carbamate | P(O)(OEt)₂ | tert-butyl |
| 134 | cyclopentyl ketone | 4-F isoindoline carbamate | P(O)(OEt)₂ | tert-butyl |
| 135 | cyclopentyl amide | 4-F isoindoline carbamate | P(O)(OEt)₂ | tert-butyl |
| 136 | 2-thienyl sulfonyl | 4-F isoindoline carbamate | P(O)(OEt)₂ | tert-butyl |

TABLE 2-continued

| Cpd# | A | P* | ![PUV] | L |
|------|---|----|----|---|
| 137 | cyclopentyl-NH-S(O)₂- | 4-fluoro-isoindoline-2-carboxylate (O-linked) | P(O)(OEt)(OEt) | t-Bu |
| 138 | t-BuO-C(O)-CH< | 3-(thiophen-2-yl)quinoxalin-2-yloxy | P(O)(OH)(OH) | t-Bu |
| 139 | cyclopentyl-O-C(O)- | 3-(thiophen-2-yl)quinoxalin-2-yloxy | P(O)(OH)(OH) | t-Bu |
| 140 | cyclopentyl-C(O)- | 3-(thiophen-2-yl)quinoxalin-2-yloxy | P(O)(OH)(OH) | t-Bu |
| 141 | cyclopentyl-NH-C(O)- | 3-(thiophen-2-yl)quinoxalin-2-yloxy | P(O)(OH)(OH) | t-Bu |
| 142 | thiophen-2-yl-S(O)₂- | 3-(thiophen-2-yl)quinoxalin-2-yloxy | P(O)(OH)(OH) | t-Bu |

TABLE 2-continued

| Cpd# | A | P* | [phosphonate group] | L |
|------|---|----|--------------------|---|
| 143 | cyclopentyl-NH-SO₂- | 2-thienyl-quinoxalin-3-yloxy | P(=O)(OH)₂ | tert-butyl |
| 144 | tert-butyl ester | 4-fluoro-isoindoline-2-carbonyloxy | P(=O)(OH)₂ | tert-butyl |
| 145 | cyclopentyl ester | 4-fluoro-isoindoline-2-carbonyloxy | P(=O)(OH)₂ | tert-butyl |
| 146 | cyclopentyl ketone | 4-fluoro-isoindoline-2-carbonyloxy | P(=O)(OH)₂ | tert-butyl |
| 147 | cyclopentyl-NH-C(=O)- | 4-fluoro-isoindoline-2-carbonyloxy | P(=O)(OH)₂ | tert-butyl |

TABLE 2-continued
| Cpd# | A | P* | ![P(O)(U)(V)] | L |
|---|---|---|---|---|
| 148 | 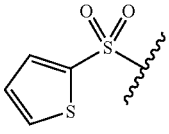 | 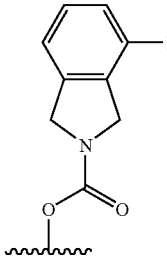 | 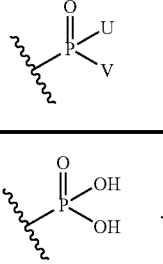 | 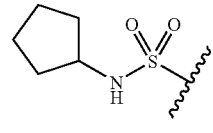 |
| 149 | 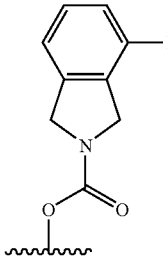 | 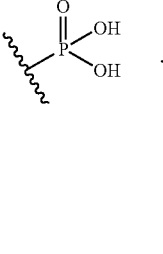 | 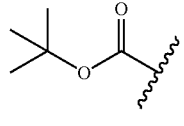 | 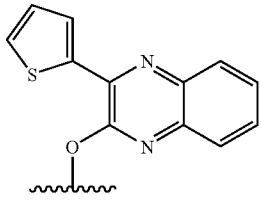 |
| 150 | 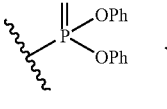 | 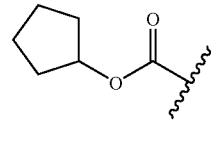 | 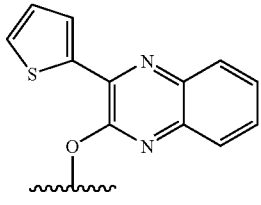 | 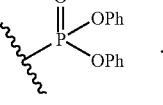 |
| 151 | 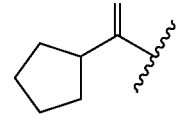 | 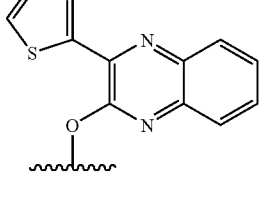 | 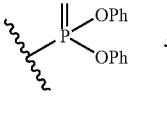 | 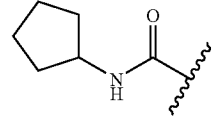 |
| 152 | 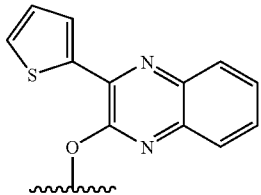 | 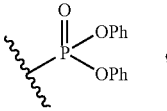 | | |
| 153 | | | | |

TABLE 2-continued

| Cpd# | A | P* | (phosphonate group) | L |
|---|---|---|---|---|
| 154 | thiophene-2-sulfonyl | 3-(thiophen-2-yl)quinoxalin-2-yloxy | P(=O)(OPh)(OPh) | tert-butyl |
| 155 | N-cyclopentyl sulfamoyl | 3-(thiophen-2-yl)quinoxalin-2-yloxy | P(=O)(OPh)(OPh) | tert-butyl |
| 156 | tert-butoxycarbonyl | 4-fluoroisoindoline-2-carbonyloxy | P(=O)(OPh)(OPh) | tert-butyl |
| 157 | cyclopentyloxycarbonyl | 4-fluoroisoindoline-2-carbonyloxy | P(=O)(OPh)(OPh) | tert-butyl |
| 158 | cyclopentylcarbonyl | 4-fluoroisoindoline-2-carbonyloxy | P(=O)(OPh)(OPh) | tert-butyl |
| 159 | N-cyclopentylcarbamoyl | 4-fluoroisoindoline-2-carbonyloxy | P(=O)(OPh)(OPh) | tert-butyl |

TABLE 2-continued
| Cpd# | A | P* | $\overset{O}{\underset{V}{\overset{\|}{P}}}\overset{U}{}$ | L |
|---|---|---|---|---|
| 160 | 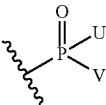 | 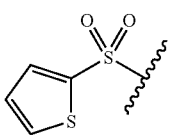 | 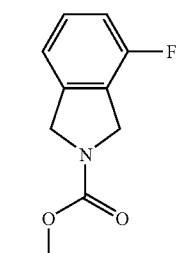 | 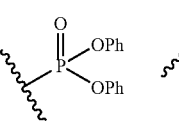 |
| 161 |  | 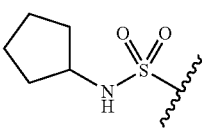 | 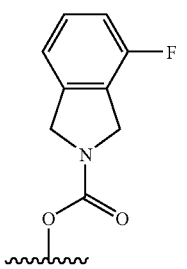 | 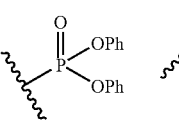 |
| 162 |  | 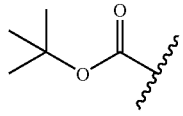 | 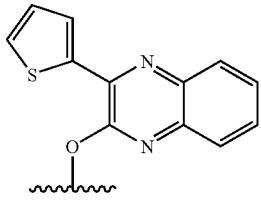 | 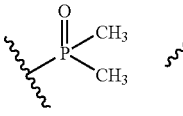 |
| 163 |  | 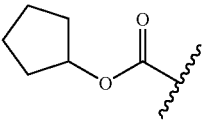 | 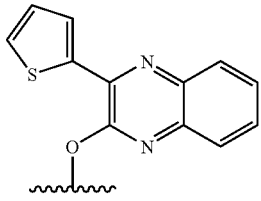 | 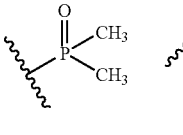 |
| 164 |  | 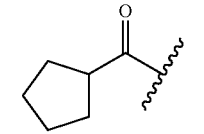 | 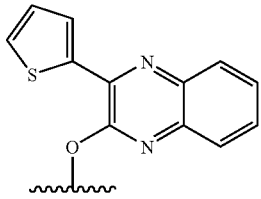 | 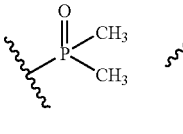 |
| 165 |  | 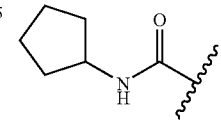 | 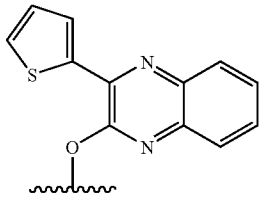 | 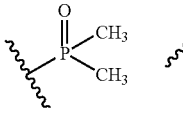 |

TABLE 2-continued

| Cpd# | A | P* | | L |
|---|---|---|---|---|
| 166 | | | | |
| 167 | | | | |
| 168 | | | | |
| 169 | | | | |
| 170 | | | | |
| 171 | | | | |

TABLE 2-continued
| Cpd# | A | P* | | L |
|---|---|---|---|---|
| 172 | 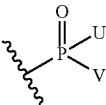 | 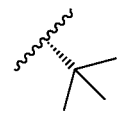 | 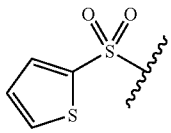 | 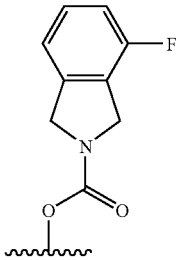 |
| 173 | 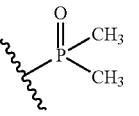 | 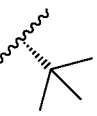 | 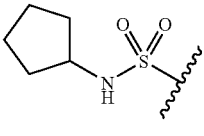 | 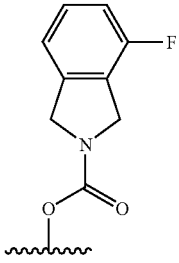 |
| 174 | 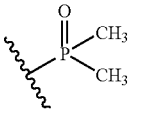 |  | 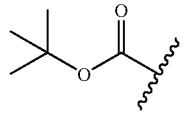 | 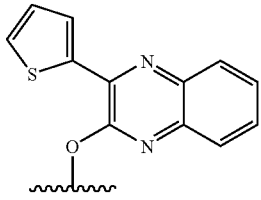 |
| 175 | 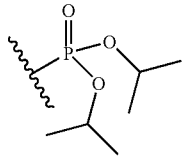 |  | 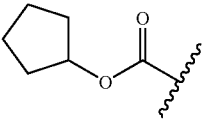 | 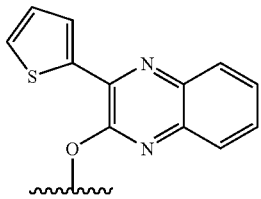 |
| 176 | 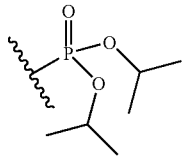 |  | 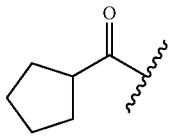 | 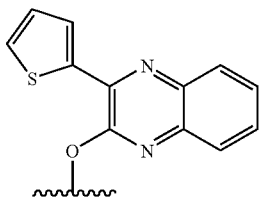 |
| 177 | 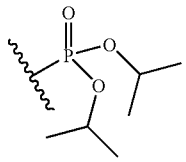 | 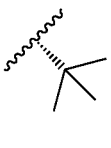 | 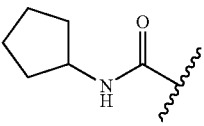 | 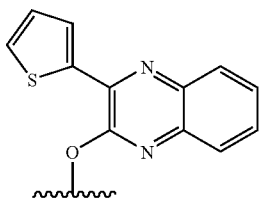 |

TABLE 2-continued

| Cpd# | A | P* | | L |
|---|---|---|---|---|
| 178 | thiophene-2-sulfonyl | 3-(thiophen-2-yl)quinoxalin-2-yloxy | isopropyl phosphonate | neopentyl |
| 179 | N-cyclopentyl sulfamoyl | 3-(thiophen-2-yl)quinoxalin-2-yloxy | isopropyl phosphonate | neopentyl |
| 180 | tert-butyl ester | 4-fluoroisoindoline-2-carbonyloxy | isopropyl phosphonate | neopentyl |
| 181 | cyclopentyl ester | 4-fluoroisoindoline-2-carbonyloxy | isopropyl phosphonate | neopentyl |
| 182 | cyclopentyl ketone | 4-fluoroisoindoline-2-carbonyloxy | isopropyl phosphonate | neopentyl |
| 183 | N-cyclopentyl amide | 4-fluoroisoindoline-2-carbonyloxy | isopropyl phosphonate | neopentyl |

TABLE 2-continued

| Cpd# | A | P* | (O=P(U)(V)-) | L |
|---|---|---|---|---|
| 184 | thiophene-2-sulfonyl | 4-fluoroisoindoline-2-carboxylate | diisopropyl phosphonate | tert-butyl |
| 185 | N-cyclopentylsulfamoyl | 4-fluoroisoindoline-2-carboxylate | diisopropyl phosphonate | tert-butyl |
| 186 | tert-butyl ester | 3-(thiophen-2-yl)quinoxalin-2-yloxy | phospholane 1-oxide | tert-butyl |
| 187 | cyclopentyl ester | 3-(thiophen-2-yl)quinoxalin-2-yloxy | phospholane 1-oxide | tert-butyl |
| 188 | cyclopentyl ketone | 3-(thiophen-2-yl)quinoxalin-2-yloxy | phospholane 1-oxide | tert-butyl |
| 189 | N-cyclopentyl amide | 3-(thiophen-2-yl)quinoxalin-2-yloxy | phospholane 1-oxide | tert-butyl |

TABLE 2-continued
| Cpd# | A | P* | 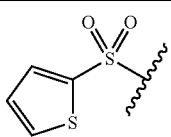 | L |
|------|---|----|----|---|
| 190 | 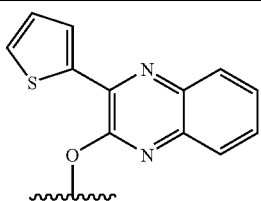 | 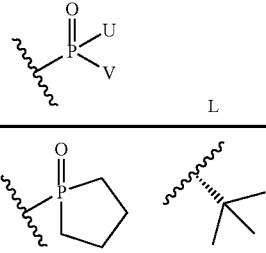 | 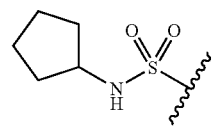 | 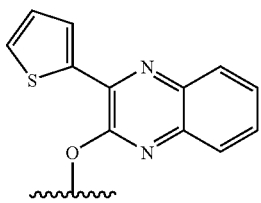 |
| 191 |  | 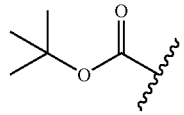 | 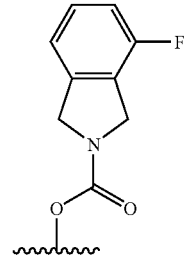 | 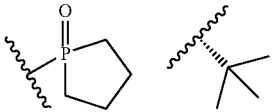 |
| 192 | 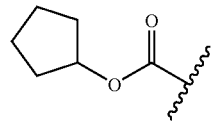 | 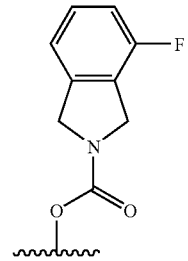 |  | 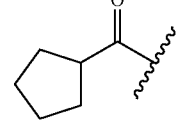 |
| 193 | 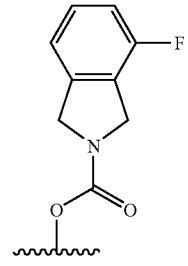 | 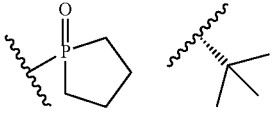 | 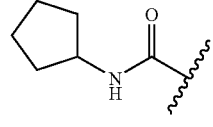 | 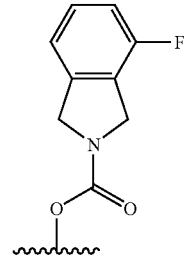 |
| 194 | 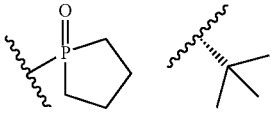 | | | |

TABLE 2-continued
| Cpd# | A | P* | 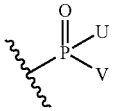 | L |
|---|---|---|---|---|
| 196 |  | 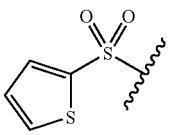 | 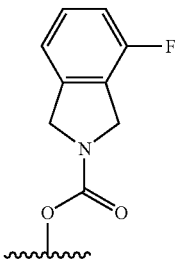 | 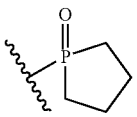 |
| 197 |  | 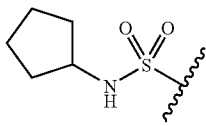 | 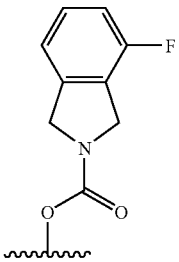 | 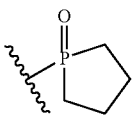 |
| 198 |  | 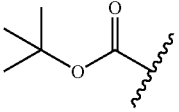 | 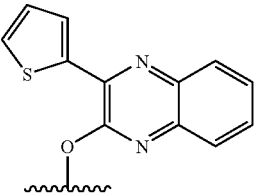 | 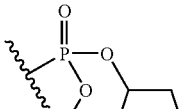 |
| 199 | 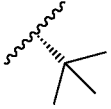 | 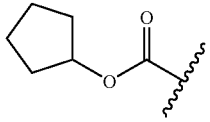 | 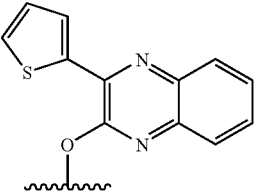 | 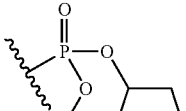 |
| 200 |  | 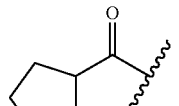 | 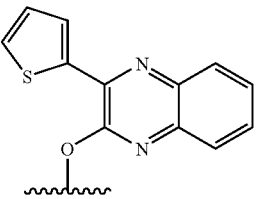 | 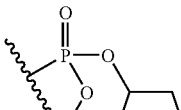 |
| 201 |  | 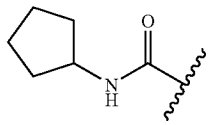 | 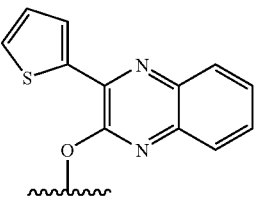 | 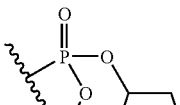 |

TABLE 2-continued
| Cpd# | A | P* | 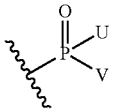 | L |
|---|---|---|---|---|
| 202 | 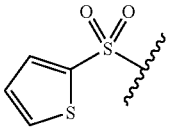 | 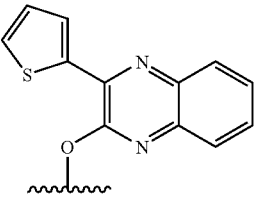 | 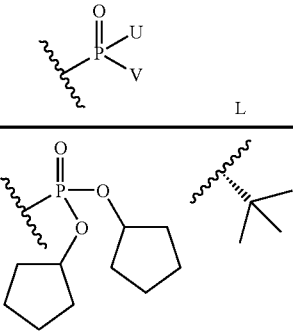 | 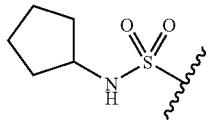 |
| 203 | 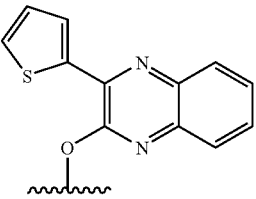 | 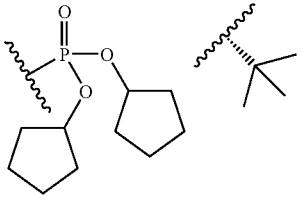 | 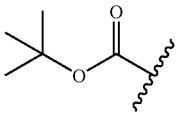 | 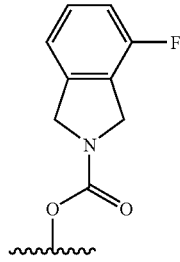 |
| 204 | 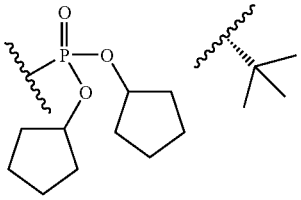 | 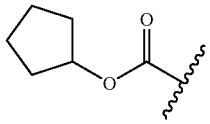 | 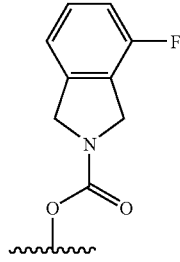 | 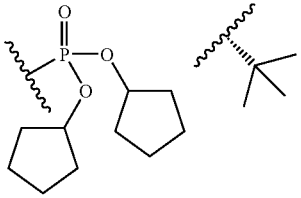 |
| 205 | 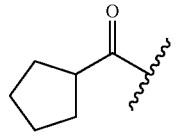 | 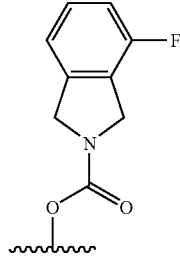 | 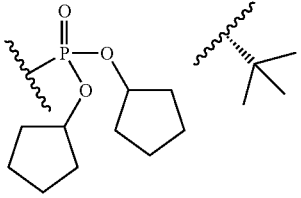 | 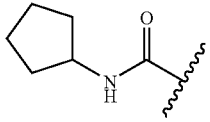 |
| 206 | 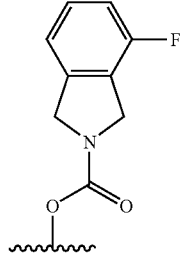 | 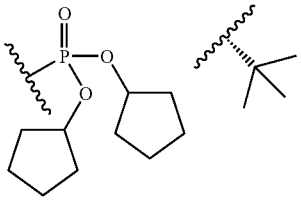 | | |
| 207 | | | | |

TABLE 2-continued
| Cpd# | A | P* | 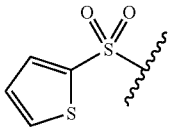 | L |
|---|---|---|---|---|
| 208 | 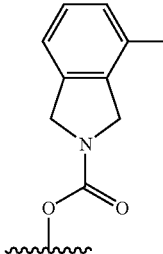 | 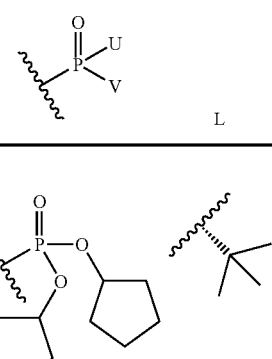 | 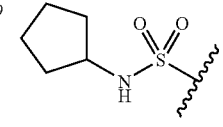 | 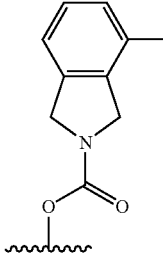 |
| 209 | 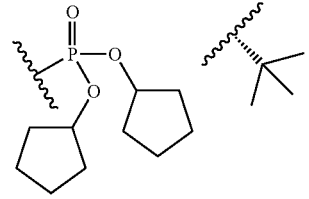 | 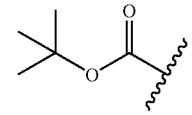 | 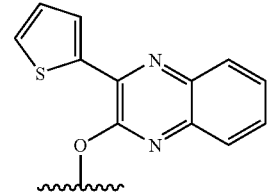 | 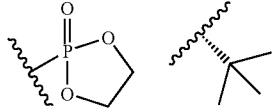 |
| 210 | 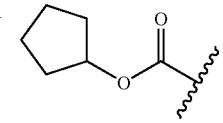 | 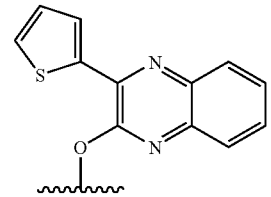 | 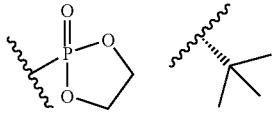 | 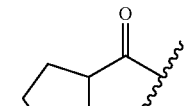 |
| 211 | 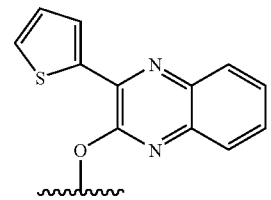 | 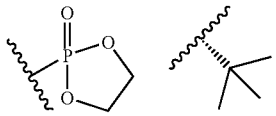 | 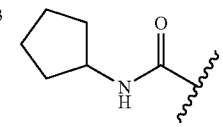 | 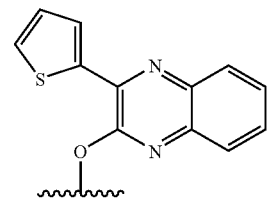 |
| 212 | 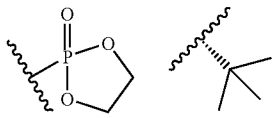 | | | |
| 213 | | | | |

TABLE 2-continued
| Cpd# | A | P* | 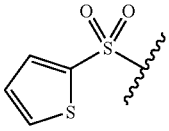 | L |
|---|---|---|---|---|
| 214 | 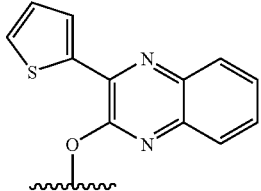 | 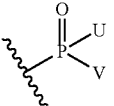 | 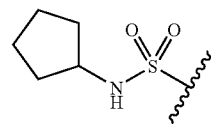 | 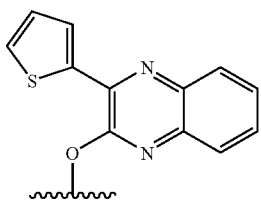 |
| 215 | 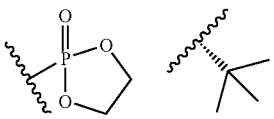 | 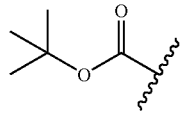 | 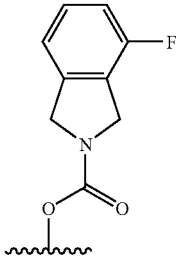 | 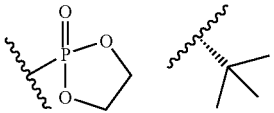 |
| 216 | 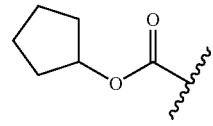 | 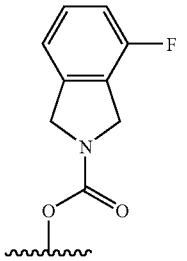 | 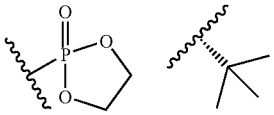 | 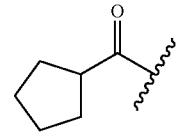 |
| 217 | 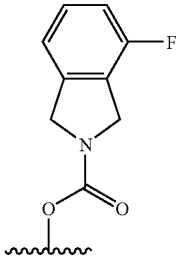 | 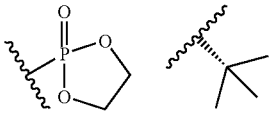 | 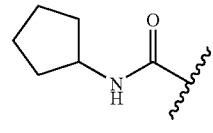 | 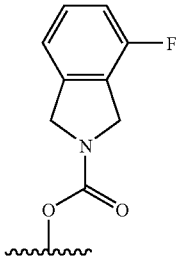 |
| 218 | 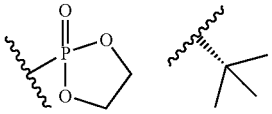 | | | |
| 219 | | | | |

TABLE 2-continued
| Cpd# | A | P* | 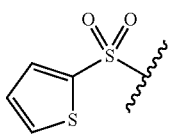 | L |
|---|---|---|---|---|
| 220 | 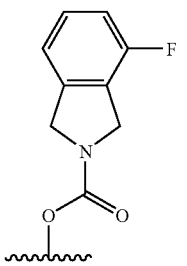 | 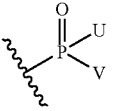 | 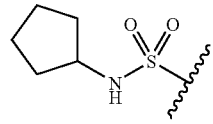 | 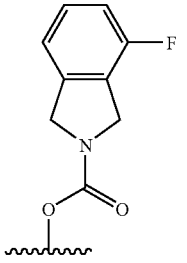 |
| 221 | 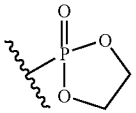 | 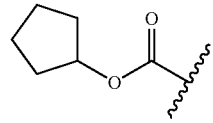 | 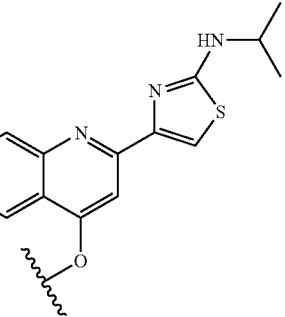 | 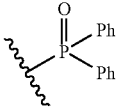 |
| 222 | 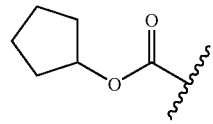 | 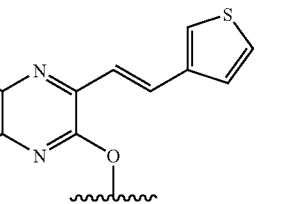 | 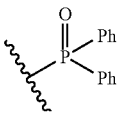 | 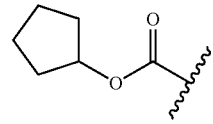 |
| 223 | 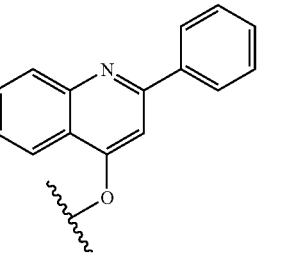 | 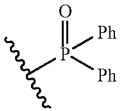 | | |
| 224 | | | | |

TABLE 2-continued

| Cpd# | A | P* | L |
|------|---|----|---|
| 225 | (cyclopentyl ester) | (5,6-dimethyl benzotriazole) | P(=O)Ph₂ / tert-butyl |
| 226 | (cyclopentyl ester) | (4-methoxyphenyl tetrazole) | P(=O)Ph₂ / tert-butyl |

A further embodiment of the present invention includes pharmaceutical compositions comprising any single compound delineated herein, or a pharmaceutically acceptable salt, ester, or prodrug thereof, with a pharmaceutically acceptable carrier or excipient.

Yet another embodiment of the present invention is a pharmaceutical composition comprising a combination of two or more compounds delineated herein, or a pharmaceutically acceptable salt, ester, or prodrug thereof, with a pharmaceutically acceptable carrier or excipient.

According to an alternate embodiment, the pharmaceutical compositions of the present invention may further contain other anti-HCV agents. Examples of anti-HCV agents include, but are not limited to, α-interferon, β-interferon, ribavirin, and amantadine. For further details see S. Tan, A. Pause, Y. Shi, N. Sonenberg, Hepatitis C Therapeutics: Current Status and Emerging Strategies, *Nature Rev. Drug Discov.*, 1, 867-881 (2002); WO 00/59929 (2000); WO 99/07733 (1999); WO 00/09543 (2000); WO 99/50230 (1999); U.S. Pat. No. 5,861,297 (1999); and US2002/0037998 (2002) which are herein incorporated by reference in their entirety.

According to an additional embodiment, the pharmaceutical compositions of the present invention may further contain other HCV protease inhibitors.

According to yet another embodiment, the pharmaceutical compositions of the present invention may further comprise inhibitor(s) of other targets in the HCV life cycle, including, but not limited to, helicase, polymerase, metalloprotease, and internal ribosome entry site (IRES).

According to another embodiment, the present invention includes methods of treating hepatitis C infections in a subject in need of such treatment by administering to said subject an therapeutically effective amount of the pharmaceutical compounds or compositions of the present invention. The methods can further include administration of an additional therapeutic agent, including another antiviral agent or an anti-HCV agent. The additional agent can be co-administered, concurrently administered or sequentially administered with the compound or composition delineated herein. The methods herein can further include the step of identifying that the subject is in need of treatment for hepatitis C infection. The identification can be by subjective (e.g., health care provider determination) or objective (e.g., diagnostic test) means.

An additional embodiment of the present invention includes methods of treating biological samples by contacting the biological samples with the compounds of the present invention.

Yet a further aspect of the present invention is a process of making any of the compounds delineated herein employing any of the synthetic means delineated herein.

DEFINITIONS

Listed below are definitions of various terms used to describe this invention. These definitions apply to the terms as they are used throughout this specification and claims, unless otherwise limited in specific instances, either individually or as part of a larger group.

The terms "$C_1$-$C_6$ alkyl," or "$C_1$-$C_8$ alkyl," as used herein, refer to saturated, straight- or branched-chain hydrocarbon radicals containing between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The terms "$C_2$-$C_6$ alkenyl," or "$C_2$-$C_8$ alkenyl," as used herein, denote a monovalent group derived from a hydrocarbon moiety containing from two to six, or two to eight carbon atoms having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl and the like.

The term "$C_2$-$C_6$ alkynyl," or "$C_2$-$C_8$ alkynyl," as used herein, denote a monovalent group derived from a hydrocarbon moiety containing from two to six, or two to eight carbon atoms having at least one carbon-carbon triple bond by the removal of a single hydrogen atom. Representative alkynyl groups include, but are not limited to, for example, ethynyl, 1-propynyl, 1-butynyl, heptynyl, octynyl and the like.

The term "$C_3$-$C_8$-cycloalkyl", or "$C_3$-$C_{12}$-cycloalkyl," as used herein, denotes a monovalent group derived from a monocyclic or polycyclic saturated carbocyclic ring compound by the removal of a single hydrogen atom, respectively. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl.

The term "$C_3$-$C_8$-cycloalkenyl", or "$C_3$-$C_{12}$-cycloalkenyl" as used herein, denote a monovalent group derived from a monocyclic or polycyclic carbocyclic ring compound having at least one carbon-carbon double bond by the removal of a single hydrogen atom. Examples of $C_3$-$C_8$-cycloalkenyl include, but not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, and the like.

The term "aryl," as used herein, refers to a mono- or bicyclic carbocyclic ring system having one or more aromatic rings including, but not limited to, phenyl, naphthyl, tetrahydronaphthyl, indanyl, idenyl and the like.

The term "arylalkyl," as used herein, refers to a $C_1$-$C_3$ alkyl or $C_1$-$C_6$ alkyl residue attached to an aryl ring. Examples include, but are not limited to, benzyl, phenethyl and the like.

The term "heteroaryl," as used herein, refers to a mono-, bi-, or tri-cyclic aromatic radical or ring having from five to ten ring atoms of which one ring atom is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroarylalkyl," as used herein, refers to a $C_1$-$C_3$ alkyl or $C_1$-$C_6$ alkyl residue residue attached to a heteroaryl ring. Examples include, but are not limited to, pyridinylmethyl, pyrimidinylethyl and the like.

The term "heterocycloalkyl," as used herein, refers to a non-aromatic 3-, 4-, 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The terms "substituted", "substituted $C_1$-$C_6$ alkyl," "substituted $C_1$-$C_8$ alkyl," "substituted $C_2$-$C_6$ alkenyl," "substituted $C_2$-$C_8$ alkenyl," "substituted $C_2$-$C_6$ alkynyl," "substituted $C_2$-$C_8$ alkynyl", "substituted $C_3$-$C_{12}$ cycloalkyl" "substituted $C_3$-$C_8$ cycloalkenyl," "substituted $C_3$-$C_{12}$ cycloalkenyl," "substituted aryl", "substituted heteroaryl," "substituted arylalkyl", "substituted heteroarylalkyl," "substituted heterocycloalkyl," as used herein, refer to CH, NH, $C_1$-$C_6$ alkyl, $C_1$-$C_8$ alkyl, $C_2$-$C_6$ alkenyl, $C_2$-$C_8$ alkenyl, $C_2$-$C_6$ alkynyl, $C_2$-$C_8$ alkynyl, $C_3$-$C_{12}$ cycloalkyl, $C_3$-$C_8$ cycloalkenyl, $C_3$-$C_{12}$ cycloalkenyl, aryl, heteroaryl, arylalkyl, heteroarylalkyl, heterocycloalkyl groups as previously defined, substituted by independent replacement of one, two, or three or more of the hydrogen atoms thereon with substituents including, but not limited to, —F, —Cl, —Br, —I, —OH, protected hydroxy, —$NO_2$, —CN, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, $NHC(S)NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —$SO_2NH_2$, —$SO_2$NH—$C_1$-$C_{12}$-alkyl, —$SO_2$NH—$C_2$-$C_{12}$-alkenyl, —$SO_2$NH—$C_2$-$C_{12}$-alkenyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkenyl, —$NHSO_2$—$C_3$-$C_{12}$-cycloalkyl, —$NHSO_2$-aryl, —$NHSO_2$-heteroaryl, —$NHSO_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl. It is understood that the aryls, heteroaryls, alkyls, and the like can be further substituted.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a monovalent group derived from a monocyclic or polycyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be divalent or trivalent. Thus, alkylene, alkenylene, and alkynylene, cycloalkylene, cycloalkenylene, cycloalkynylene, arylalkylene, heteroarylalkylene and heterocycloalkylene groups are to be included in the above definitions, and are applicable to provide the formulas herein with proper valency.

The terms "halo" and "halogen," as used herein, refer to an atom selected from fluorine, chlorine, bromine and iodine.

The compounds described herein contain one or more asymmetric centers and thus give rise to enantiomers, diastereomers, and other stereoisomeric forms that may be defined, in terms of absolute stereochemistry, as (R)- or (S)-, or as D- or L- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high-performance liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, viral infections are treated or prevented in a subject, such as a human, by administering to the subject a therapeutically effective amount of a compound of the invention, in such amounts and for such time as is necessary to achieve the desired result. The term "therapeutically effective amount" of a compound of the invention, as used herein, means a sufficient amount of the compound so as to decrease the viral load in a subject and/or decrease the subject's HCV symptoms. As is well understood in the medical arts a therapeutically effective amount of a compound of this invention will be at a reasonable benefit/risk ratio applicable to any medical treatment.

It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

An additional method of the present invention is the treatment of biological samples with an inhibitory amount of a compound of the present invention in such amounts and for such time as is necessary to inhibit viral replication and/or reduce viral load. The term "inhibitory amount" means a sufficient amount to inhibit viral replication and/or decrease the hepatitis C viral load in a biological sample. The term "biological sample(s)" as used herein means a substance of biological origin intended for administration to a subject. Examples of biological samples include, but are not limited to blood and components thereof such as plasma, platelets, subpopulations of blood cells and the like; organs such as kidney, liver, heart, lung, and the like; sperm and ova; bone marrow and components thereof; or stem cells. Thus another embodiment of the present invention is a method of treating a biological sample by contacting said biological sample with an inhibitory amount of a compound or pharmaceutical composition of the present invention.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations used in the descriptions of the schemes and the examples that follow are:
  aq. for aqueous;
  CDI for 1,1'-carbonyldiimidazole;
  DBU for 1,8-diazabicyclo[5.4.0]undec-7-ene;
  DCM for dichloromethane;
  DIAD for diisopropyl azodicarboxylate;
  DIEA for diisopropyl ethylamine;
  DME for ethylene glycol dimethyl ether;
  DMF for N,N-dimethyl formamide;
  ESI for electrospray ionization;
  Et for ethyl;
  EtOAc for ethyl acetate;
  g for gram(s);
  h for hour(s);
  HATU for O-(7-Azabenzotriazole-1-yl)-N,N,N',N'-tetramethyluronium hexafluoro-phosphate;
  HPLC for high-performance liquid chromatography;
  Ph for phenyl;
  Me for methyl;
  MeOH for methanol;
  mg for milligram(s);
  min for minute(s);
  MS for mass spectrometry;
  NMR for nuclear magnetic resonance;
  rt for room temperature;
  THF for tetrahydrofuran;
  TLC for thin layer chromatography;
  PPh$_3$ for triphenylphosphine;
  tBOC or Boc for tert-butyloxy carbonyl;

Synthetic Methods

The compounds and processes of the present invention will be better understood in connection with the following synthetic schemes that illustrate the methods by which the compounds of the invention may be prepared.

The targeted analogs were prepared from the common tripeptide intermediates 1-6 and 1-8 and the like. Synthesis toward these versatile intermediates began with the saponification of commercially available Boc-hydroxyproline methyl ester (1-1) with lithium hydroxide in a 3:1:1 mixture of THF/MeOH/water to generate corresponding acid 1-2 (Scheme 1). Subsequent coupling with the cyclopropyl-derived amino acid derivative 1-3 exploiting HATU afforded dipeptide 1-4. HCl-mediated Boc-deprotection in dioxane yielded proline salt 1-5, which was further coupled with Boc-tert-L-leucine to give the desired tripeptide 1-6. It is important to note, that alternative amino acid derivatives can be used in either coupling step to generate tripeptides analogous to 1-6, and therefore ultimately produce multiple alternative pyridazinone analogs. Conversely, 1-5 could also be coupled to the olefin-containing amino acid 1-7 delivering a tripeptide that could be cyclized to intermediate 1-8 utilizing the first generation Hoveyda-Grubbs catalyst.

It is important to note, that although only the cis-hydroxyproline series is shown in Scheme 1, the trans-hydroxyproline series can be carried through an identical synthetic sequence. Both series are used in order to generate the targeted HCV inhibitors.

Scheme 1.

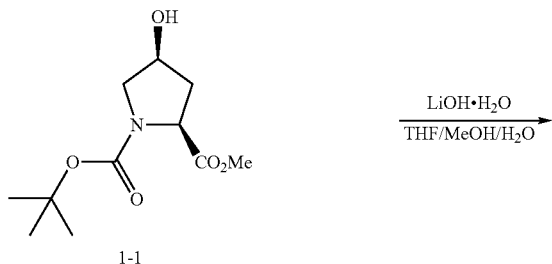

-continued
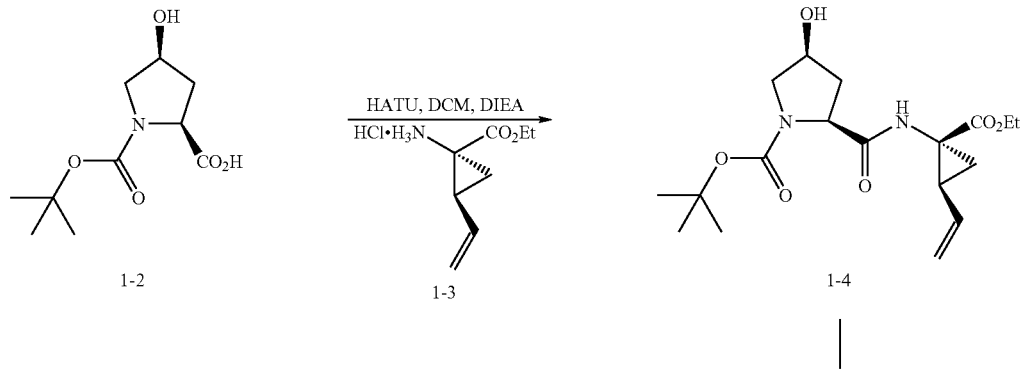
1-2  1-3  1-4
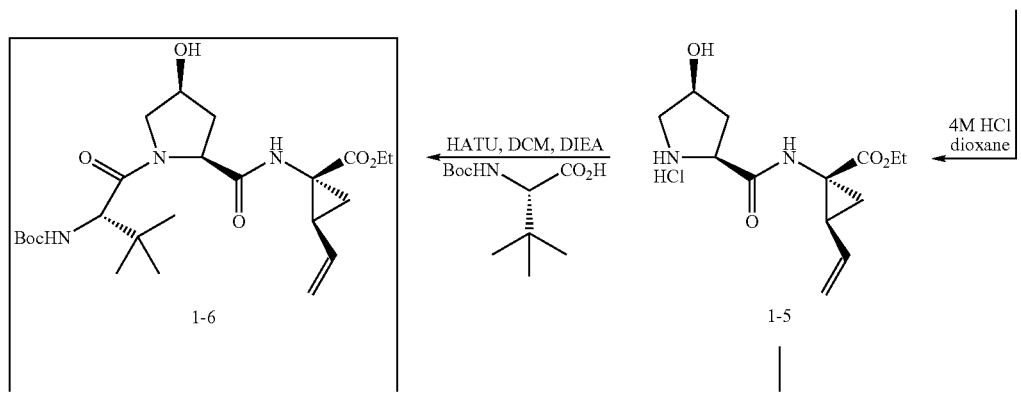
1-6  1-5
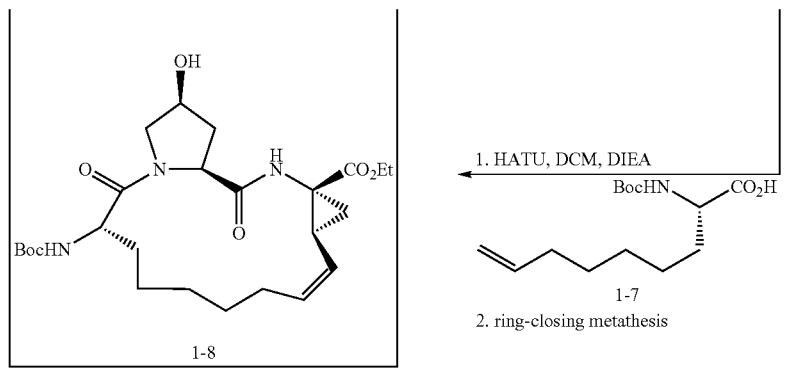
1-8  1-7
2. ring-closing metathesis Employing standard Mitsubobu protocols, cis-proline-containing intermediates 1-6 and 1-8 can be transformed to the versatile quinoxaline-containing compounds 2-1 and 2-2. Although this scheme is not comprehensive, the chemistry portrayed therein serves as a general guide toward multiple quinoxaline-derived species. For further details on the Mitsunobu reaction, see O. Mitsunobu, *Synthesis* 1981, 1-28.

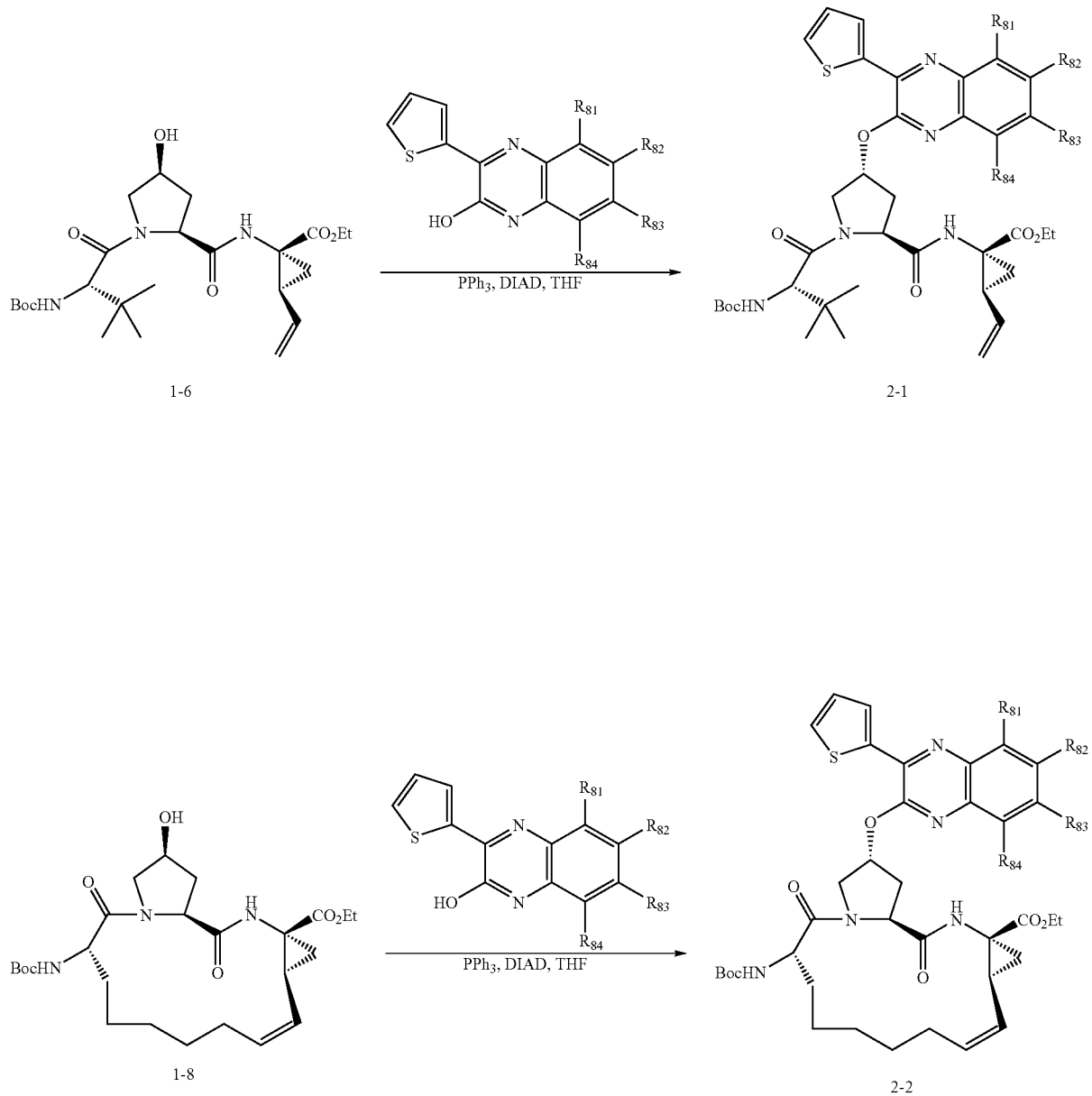

Scheme 2.

As stated above, both the cis-proline- and trans-proline-derived intermediates were used in this study. Consequently, epi-1-6 and epi-1-8 can both be condensed with CDI, and the resulting product subjected to various isoindolines to generate a variety of acyclic and cyclic carbamates, represented by 3-1 and 3-2, respectively. As before, scheme 3 is not comprehensive, however the chemistry portrayed therein serves as a general guide toward multiple carbamate-derived species.

Scheme 3.

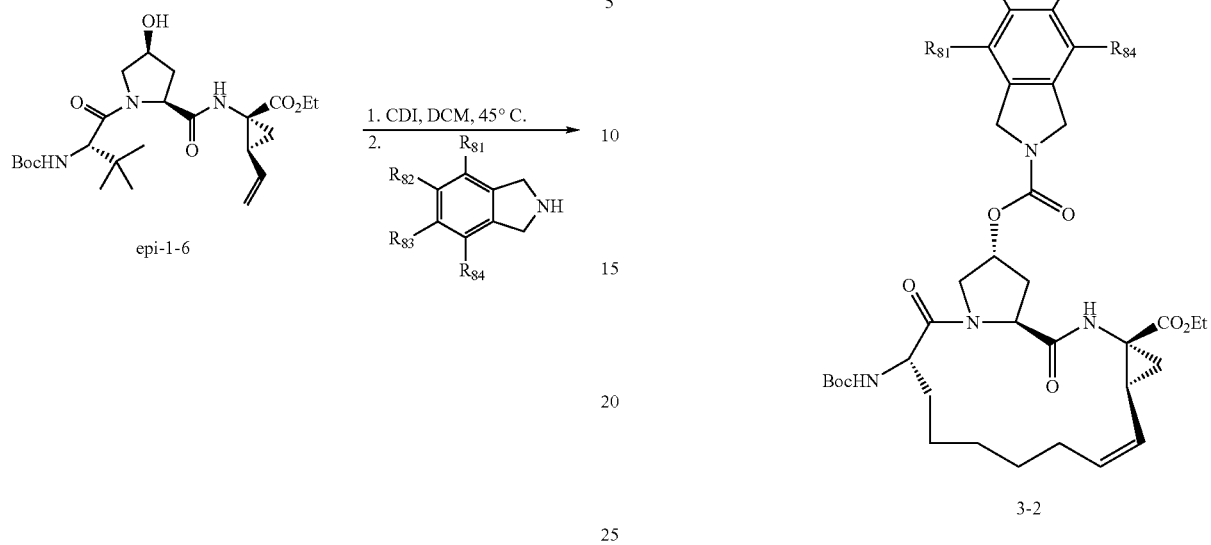

Functionalization at the N-terminus can be carried out using a two-step sequence (Scheme 4) beginning with HCl-mediated Boc-deprotection. Once the amine salts (4-1 and 4-2) are generated, they can then be condensed with an array of electrophiles under basic conditions to produce alternative carbamates [—(C=O)—O—$R_1$], amides [—(C=O)—$R_2$], ureas [—C(=O)—NH—$R_2$], or sulfonamides [—S(O)$_2$—$R_1$, —S(O)$_2$NH$R_2$], wherein $R_1$ and $R_2$ are as previously defined.

Scheme 4.

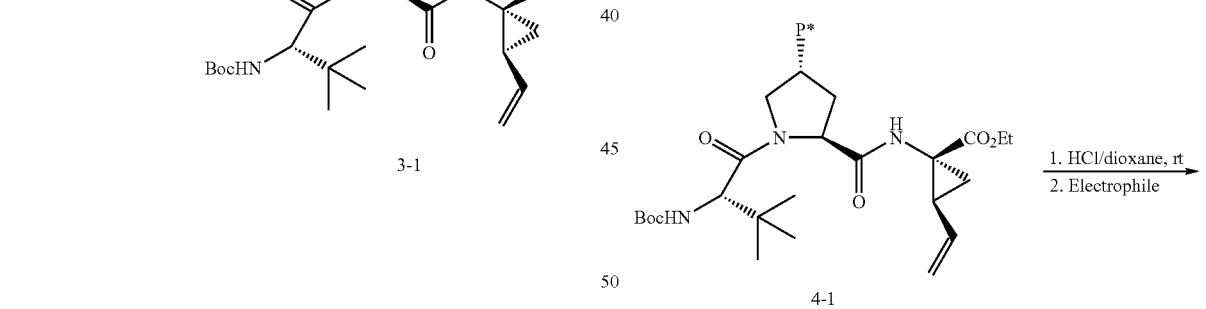

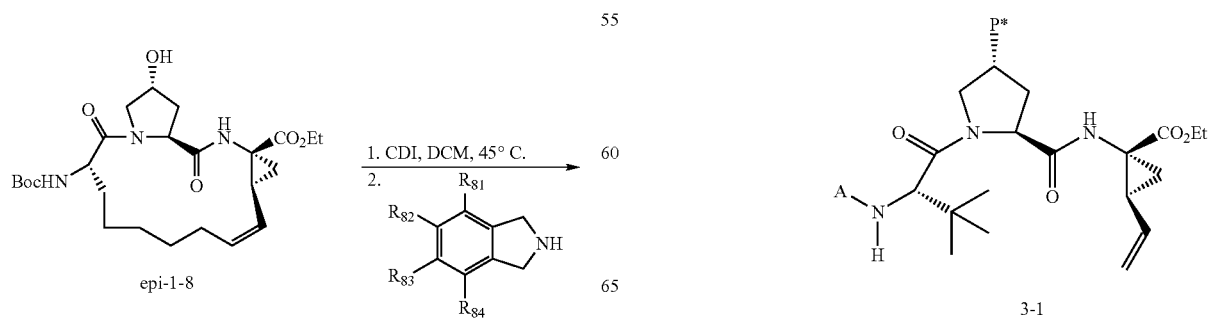

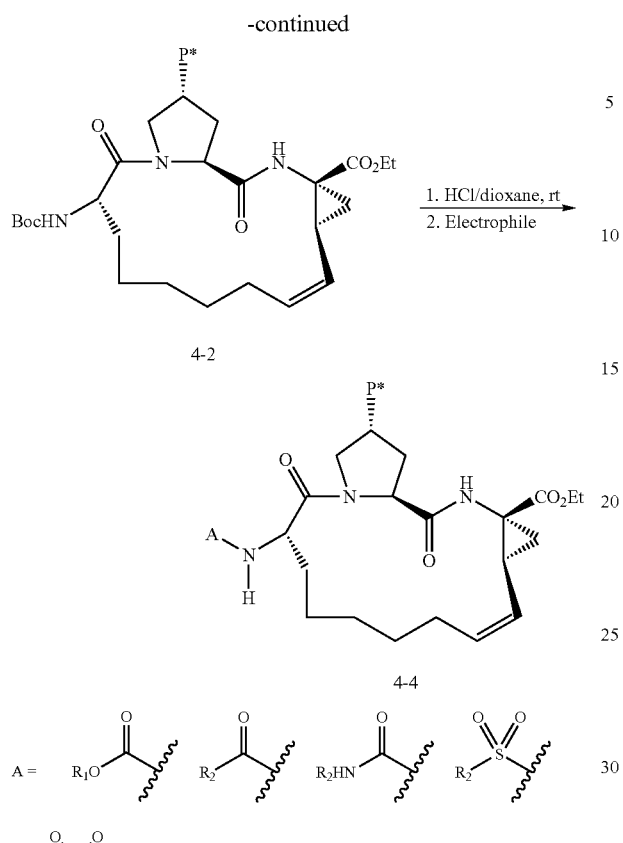

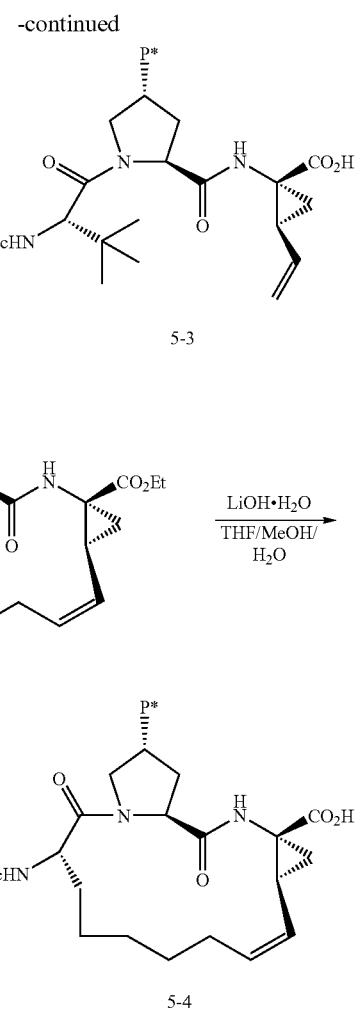

The final steps to the targeted analogs of the present invention include a saponification followed by the formation of the requisite phosphorus moiety. This strategy was initiated with the treatment of the ethyl esters 5-1 and 5-2 with lithium hydroxide in a 3:1:1 mixture of THF/MeOH/water (Scheme 5a). Once the carboxylic acids 5-3 and 5-4 were formed, they could be condensed with CDI, then subjected to the free phosphoramidate or phosphinamide (Scheme 5b). Examples of this methodology are illustrated in, but not limited to, the conversion of compounds represented by structure 5-1 and 5-2 to the phosphorus-derived compounds represented by structure 5-5 and 5-6.

Scheme 5a.

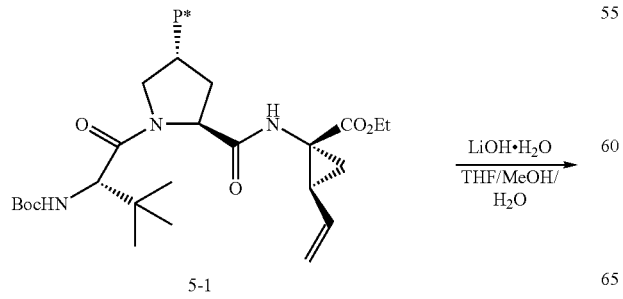

Scheme 5b.

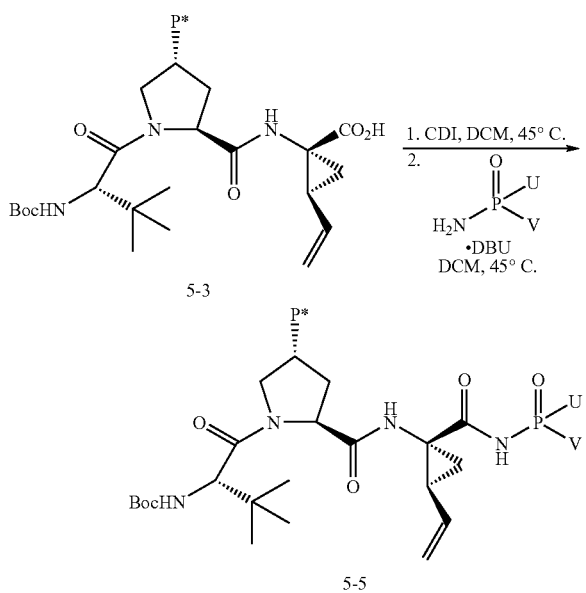

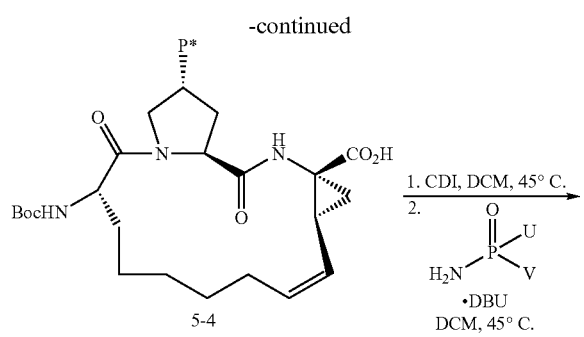

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as illustrations only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Synthesis of the Tri-Peptide Intermediates: (NOTE: this Sequence was Also Carried Out Using the Trans-Hydroxy Proline Compound Analogous to Structure 1a)

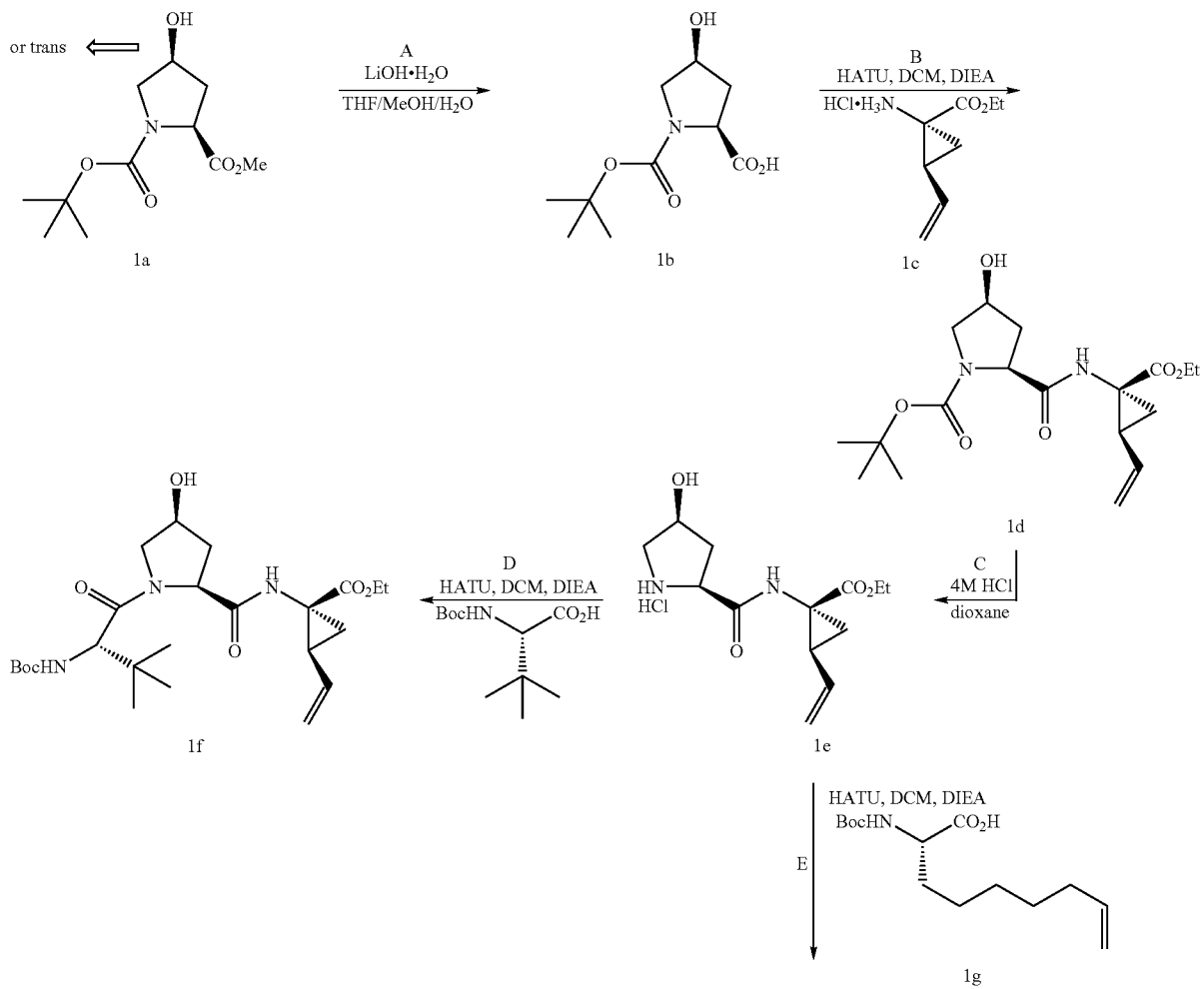

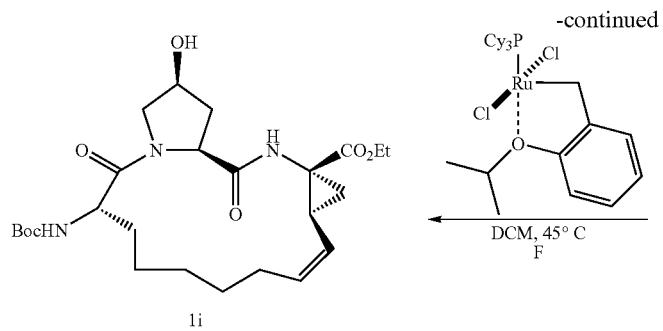

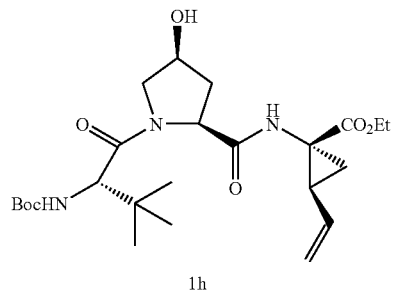

Step 1A. To a solution of commercially available cis-L-hydroxyproline methyl ester (1a) (1.00 g, 4.08 mmol) in 165 ml of a 3:1:1 mixture of THF/MeOH/water at room temperature was added LiOH.H$_2$O (0.51 g, 12.24 mmol). The resulting heterogeneous reaction was stirred at room temperature for 14 h, at which time the reaction was concentrated to ~⅕ of its original volume, then acidified with 6M HCl(aq). This aqueous solution was then diluted with 20 mL brine and extracted with DCM (4×50 mL). The organic washings were combined, washed with once with brine, dried (Na$_2$SO$_4$), filtered, and concentrated in vacuo. The resulting crude carboxylic acid 1b was carried on without further purification.

Step 1B. Carboxylic acid 1b (4.08 mmol) was diluted with 50 mL of DCM, cooled to 0° C., then consecutively treated with DIEA (4.12 g, 32.64 mmol), cyclopropyl-derived amino-acid hydrochloride salt 1c (0.78 g, 4.08 mmol), and HATU (1.94 g, 5.10 mmol). The reaction mixture was warmed to room temperature and closely monitored using mass spectrometric analysis. Once the reaction was complete, it was transferred to a 250 mL separatory funnel with 75 mL EtOAc, at which time it was extracted with saturated aqueous NaHCO$_3$ (2×20 ml) and brine (2×20 ml). The organic phase was dried over anhydrous Na$_2$SO$_4$, filtered, and then concentrated in vacuo. The residue was purified by silica gel flash chromatography using gradient elution with hexanes:EtOAc (5:1→3:1→1:1→1:2→1:5) yielding the dipeptide 1d (0.826 g, 55%).

MS (ESI) m/z=369.3 (M+H)$^+$.

Step 1C To neat dipeptide 1d was added 20 mL of a 4M HCl solution in dioxane. The resulting mixture was stirred at room temperature for 3 h. Once Boc-deprotection was complete, the excess HCl and organic solvent was removed in vacuo. The resulting amino salt 1e was used without any further purification.

MS (ESI) m/z=269.2 (M+H)$^+$.

Step 1D. Amine salt 1e (2.24 mmol) was diluted with 25 mL of DCM, cooled to 0° C., then consecutively treated with DIEA (1.41 g, 11.2 mmol), Boc-tert-L-leucine (0.52 g, 2.24 mmol), and HATU (1.06 g, 2.80 mmol). The reaction mixture was warmed to room temperature and closely monitored using mass spectrometric analysis. Once the reaction was complete, it was transferred to a 250 mL separatory funnel with 100 mL EtOAc, at which time it was extracted with saturated aqueous NaHCO$_3$ (2×20 ml) and brine (2×20 ml). The organic phase was dried over anhydrous Na$_2$SO$_4$, filtered, and then concentrated in vacuo. The residue was purified by silica gel flash chromatography using gradient elution with hexanes:EtOAc (5:1→3:1→1:1→1:2→1:5) yielding the desired tripeptide intermediate 1f (1.13 g, 93%) as a white solid.

MS (ESI) m/z=482.4 (M+H)$^+$.

Step 1E. Amine salt 1e (2.24 mmol) was diluted with 25 mL of DCM, cooled to 0° C., then consecutively treated with DIEA (1.41 g, 11.2 mmol), amino acid 1g (0.61 g, 2.24 mmol), and HATU (1.06 g, 2.80 mmol). The reaction mixture was warmed to room temperature and closely monitored using mass spectrometric analysis. Once the reaction was complete, it was transferred to a 250 mL separatory funnel with 100 mL EtOAc, at which time it was extracted with saturated aqueous NaHCO$_3$ (2×20 ml) and brine (2×20 ml). The organic phase was dried over anhydrous Na$_2$SO$_4$, filtered, and then concentrated in vacuo. The residue was purified by silica gel flash chromatography using gradient elution with hexanes:EtOAc (5:1→3:1→1:1→1:2→1:5) yielding the desired tripeptide intermediate 1h (1.0 g, 97%) as a white solid.

MS (ESI) m/z=544.84 (M+Na)$^+$.

Step 1F. A solution of the linear tripeptide 1f (1.51 g, 2.89 mmol) in 200 ml dry DCM was deoxygenated by N$_2$ bubbling. Hoveyda's 1$^{st}$ generation catalyst (5 mol % eq.) was then added as a solid. The reaction was refluxed under N$_2$ atmosphere for 12 h. The solvent was evaporated and the residue was purified by silica gel flash chromatography using gradient elution with hexanes:EtOAc (9:1→5:1→3:1→1:1→1:2→1:5). The cyclic peptide precursor 1i was isolated as a white powder (1.24 g, 87%). For further details of the synthetic methods employed to produce the cyclic peptide precursor 1, see WO 00/059929 (2000).

MS (ESI) m/z=516.28 (M+Na)$^+$.

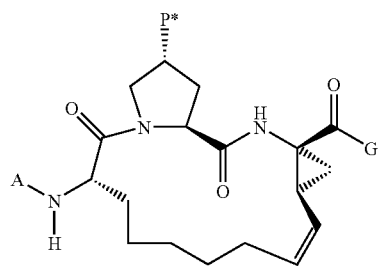

IX

Example 1

Compound of Formula IX, wherein

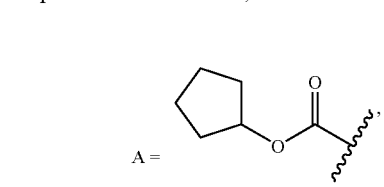

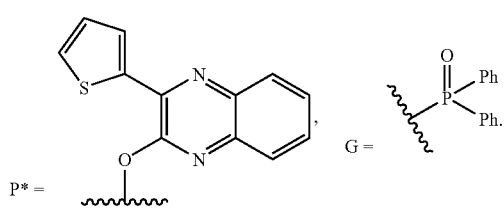

Step 2A.

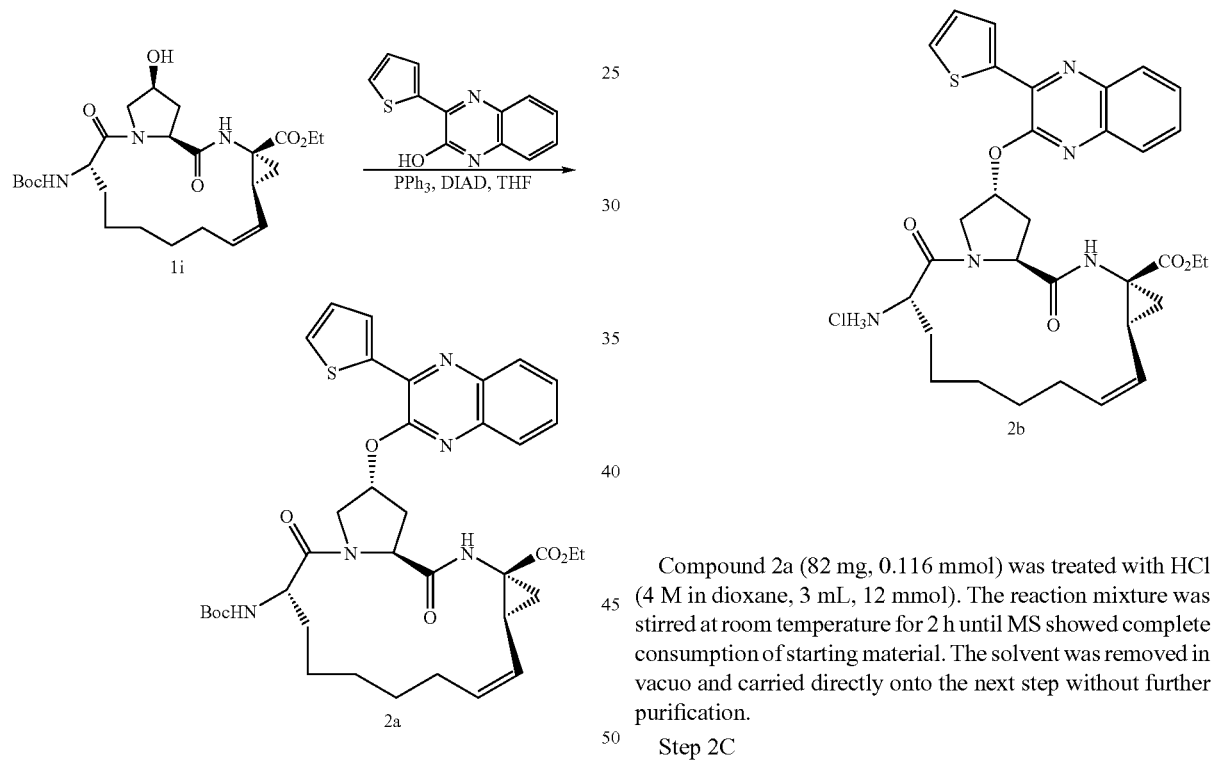

To a cooled mixture of macrocyclic precursor 1i, 3-(thiophen-2-yl)-1H-quinoxalin-2-one (1.1 equiv.), and triphenylphosphine (2 equiv.) in THF was added DIAD (2 equiv.) dropwise at 0° C. The resulting mixture was held at 0° C. for 15 min. before being warmed to room temperature. After 1 h, the mixture was concentrated under vacuum and the residue was purified by flash chromatography eluting with 60% EtOAc in hexanes to give 2a as a clear oil (100 mg, 99%).

MS (ESI) m/z=704.4 (M+H)$^+$.

H$^1$-NMR [CDCl$_3$, δ (ppm)]: 8.6 (d, 1H), 8.0 (d, 1H), 7.8 (d, 1H), 7.6 (m, 2H), 7.5 (d, 2H), 7.2 (t, 1H), 7.0 (brs, 1H), 6.0 (brt, 1H), 5.5 (m, 1H), 5.3 (brd, 1H), 5.2 (t, 1H), 5.0 (m. 1H), 4.6 (brt, 1H), 4.1-4.3 (m, 3H), 3.1 (m, 1H), 5.3 (m, 1H), 2.1-2.3 (m, 2H), 1.3 (brs, 9H), 1.2 (t, 3H).

Step 2B.

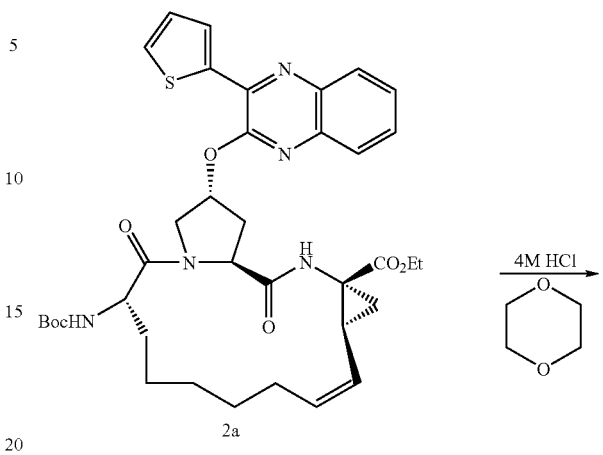

Compound 2a (82 mg, 0.116 mmol) was treated with HCl (4 M in dioxane, 3 mL, 12 mmol). The reaction mixture was stirred at room temperature for 2 h until MS showed complete consumption of starting material. The solvent was removed in vacuo and carried directly onto the next step without further purification.

Step 2C

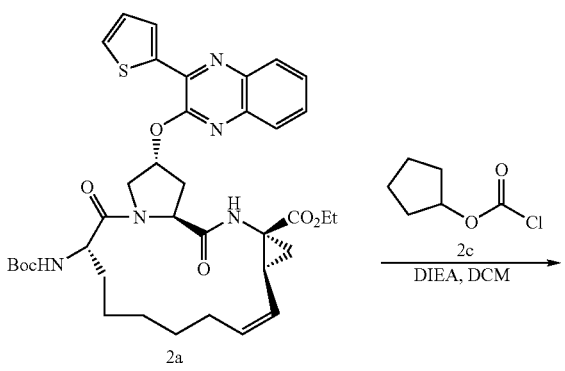

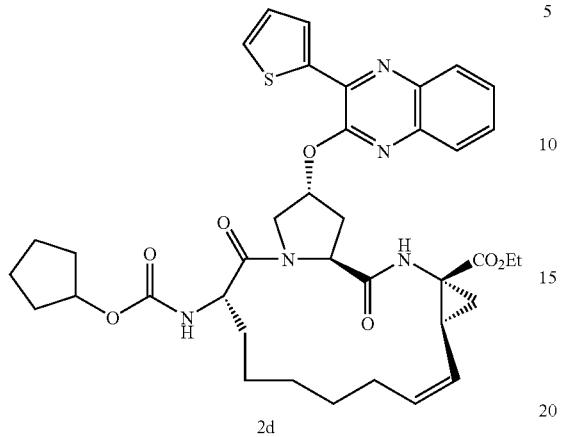

2d

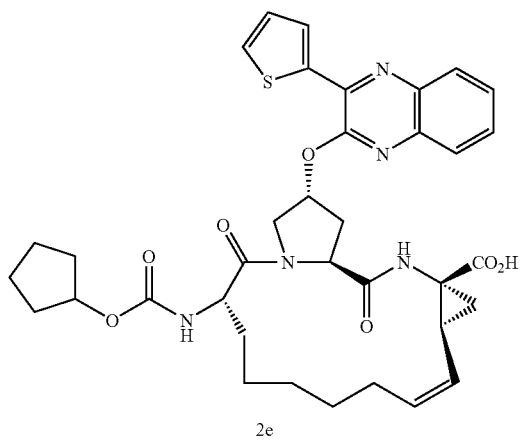

2e

The chloroformate reagent 2c was prepared by subjecting 0.22 mmol cyclopentanol in THF (5 ml) to 0.45 mmol of phosgene in toluene (20%). The resulting reaction mixture was stirred at room temperature for 2 h and the solvent was then removed in vacuo. To the residue was added DCM and the resulting mixture was subsequently concentrated in vacuo (repeat 2×) yielding chloroformate reagent 2c.

Amine salt 2b was dissolved in DCM (3 mL) then treated with cyclopentyl chloroformate (2c, 0.22 mmol) and DIEA (0.35 mL, 2 mmol). The reaction mixture was stirred for 2.5 h. Ethyl acetate (15 mL) was added to the solution, and the resulting reaction mixture was washed with saturated aqueous NaHCO$_3$ solution, water, and brine consecutively. The organic layer was dried over anhydrous sodium sulfate. The organic phase was then filtered, concentrated in vacuo and purified by flash chromatography (EtOAc/hexanes 1:2) to give 60.0 mg of the cyclopentyl carbamate 2d.

MS (ESI) m/z 716.31 (M+H)$^+$.

Step 2D.

Carbamate 2d was dissolved in THF/MeOH/H$_2$O (2:1:0.5) and subsequently subjected to lithium hydroxide (10 equiv.) at room temperature for 20 h. The excess solvents were evaporated in vacuo, and the resulting residue was diluted with water and acidified to pH ~5. The mixture was extracted with EtOAc (2×). The combined organic extracts were washed once with brine, dried (MgSO$_4$), filtered and concentrated in vacuo to give carboxylic acid 2e, (42.0 mg, 55% for three steps).

MS (ESI) m/z 688.37 (M+H)$^+$.

$^{13}$C-NMR (125 MHz, CD$_3$OD): δ 174.6, 173.5, 173.0, 156.7, 152.9, 141.1, 140.0, 139.2, 138.8, 133.4, 130.8, 130.1, 129.3, 128.0, 127.2, 126.7, 126.3, 77.5, 76.2, 59.7, 53.3, 52.6, 40.3, 34.8, 34.4, 32.4, 32.2, 32.1, 30.8, 27.5, 27.4, 26.4, 23.6, 23.3, 23.0, 22.3.

Step 2E.

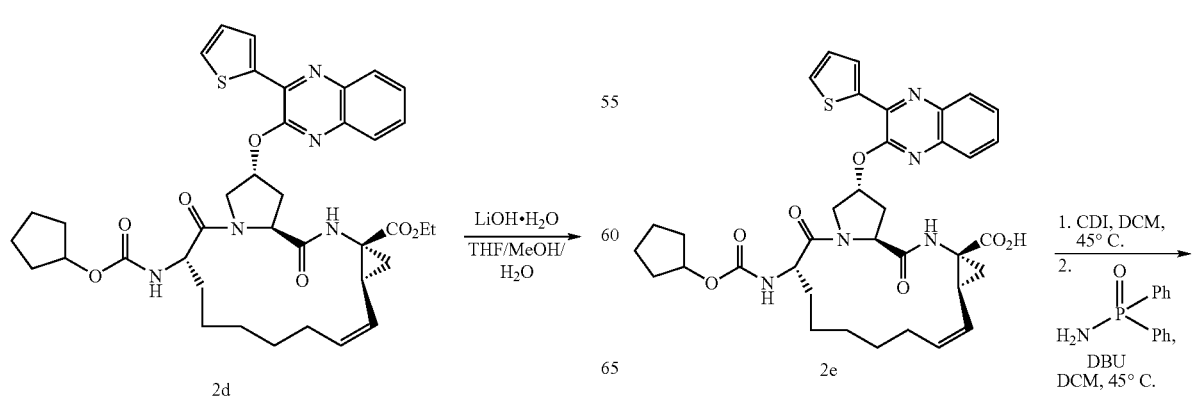

-continued

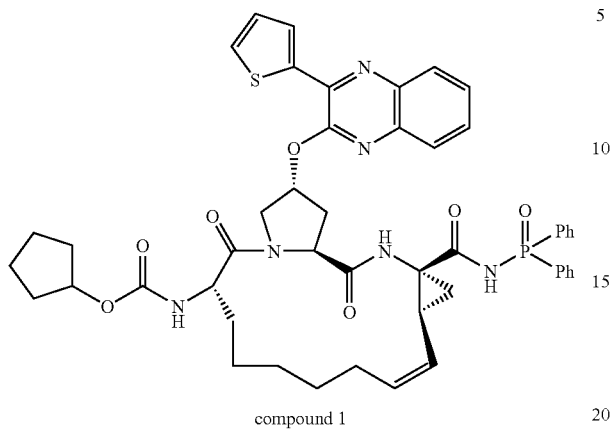

compound 1

In a one dram vial, carboxylic acid 2a (0.015 g, 0.022 mmol) was dissolved in 0.75 mL DCM, then treated with CDI (5.3 mg, 0.033 mmol). The resulting mixture was then moved to a 45° C. oil bath and stirred for 1 h. After cooling to rt, the vial was opened and diphenylphosphinamide (14.3 mg, 0.066 mmol) was added. The vial was then purged N$_2$, capped, and moved back to the 45° C. oil bath, where it was stirred for 3 h. After cooling, the reaction mixture was loaded directly onto a plug of SiO$_2$ and purified via flash chromatography using EtOAc in hexanes (20%→50%→95%) to yield the title compound, (8.0 mg, 41%) as a white solid.

MS (ESI) m/z=887.3 (M+H)$^+$.

Example 2

Compound of Formula IX, wherein

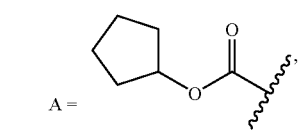

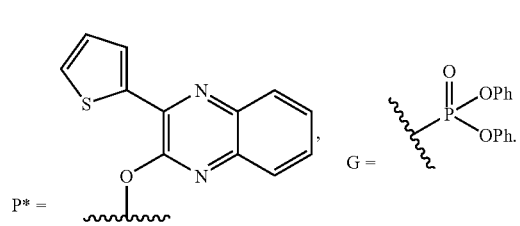

Step 2E from above was followed using diphenylphosphoramidate instead of diphenylphosphinamide.

MS (ESI) m/z=919.4 (M+H)$^+$.

Example 3

Compound of Formula IX, wherein

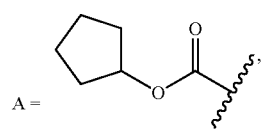

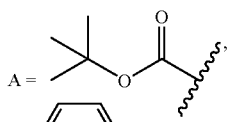

Step 2E from above was followed using diethylphosphoramidate instead of diphenylphosphinamide.

MS (ESI) m/z=823.3 (M+H)$^+$.

Example 4

Compound of Formula IX, wherein

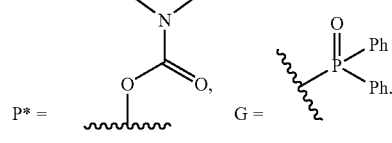

Step 5a.

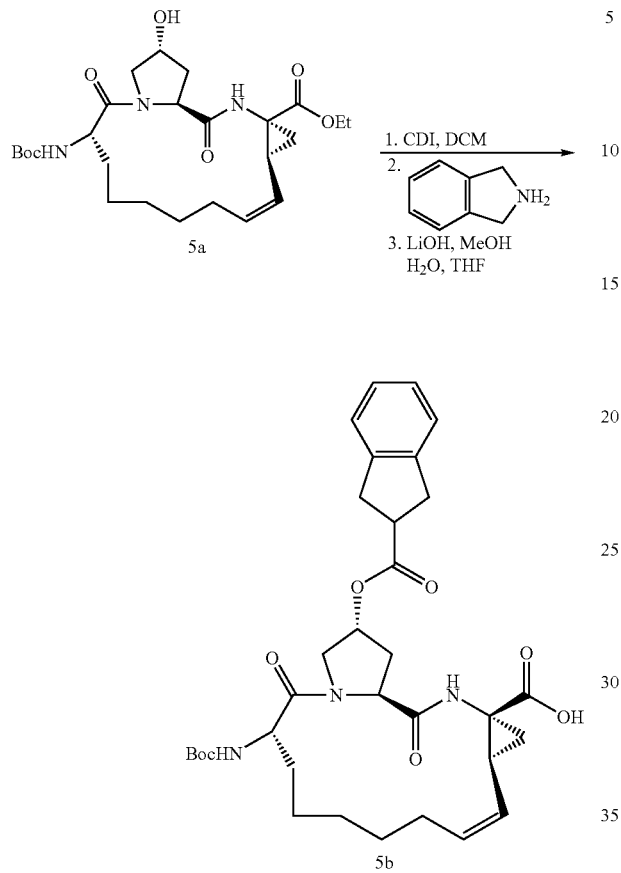

Step 5b.

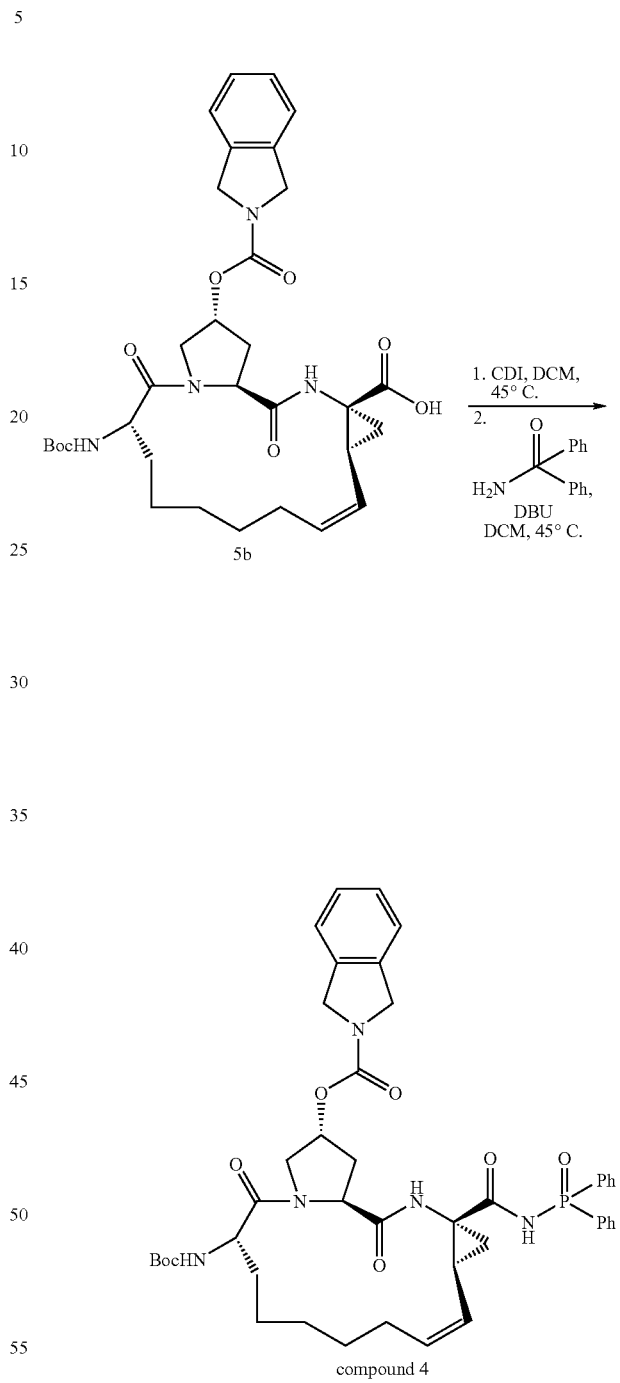

Synthesis of the title compound was initiated by the condensation of alcohol 5a (200 mg, 0.40 mmol—generated using trans-hydroxyproline and the methodology outlined in Example 1) with CDI (79 mg, 0.49 mmol) in 5 mL dichloromethane at rt. Once this coupling was complete as confirmed by MS analysis, isoindoline (145 mg, 1.21 mmol) was added and the resulting mixture was stirred overnight. The reaction mixture was diluted with dichloromethane (20 mL) and washed with 1N aq. HCl (20 mL) and brine (20 mL). The organic portion was then dried ($Na_2SO_4$), filtered, and concentrated in vacuo. The crude oil was purified via flash chromatography (silica gel) using dichloromethane/EtOAc/acetone (60:20:1) as eluent to afford the corresponding carbamate (220 mg, 85%) as a white solid.

Once the carbamate portion was installed, ester hydrolysis was carried out in standard fashion using LiOH in a THF/MeOH/water (1.5, 0.5, 0.5 mL, respectfully) solvent mixture. Upon completion, the reaction mixture was diluted with 50 mL DCM and 5 mL water, which was acidified with 1N aq. HCl. The layers were separated and the aqueous portion was washed three additional times with 10 mL DCM. The organic portions were combined and washed once with brine (20 mL). Finally, the organic layer was dried ($Na_2SO_4$), filtered, and concentrated in vacuo. The crude acid 5b was carried on to the coupling step without any further purification.

MS (ESI) m/z=611.3 $(M+H)^+$.

Using 2 mg of carboxylic acid 5b, Step 2E was followed exploiting diphenylphosphinamide as the nucleophilic entity in the second step.

MS (ESI) m/z=810.4 $(M+H)^+$.

Examples 5-113
(Formula VII, Table 3) may be prepared following procedures similar to those outlined in Examples 1-4.
TABLE 3
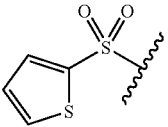
VII
| Example # | A | P* | 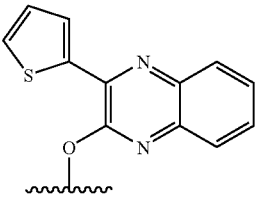 |
|---|---|---|---|
| 5 | 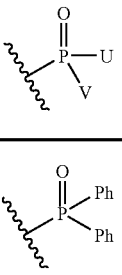 | 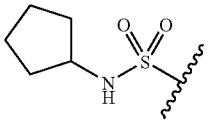 | 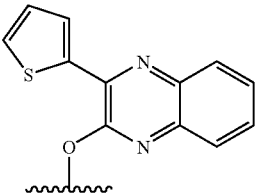 |
| 6 | 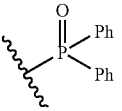 | 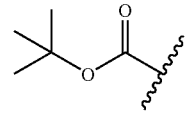 | 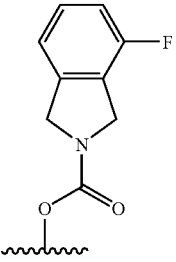 |
| 7 | 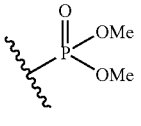 | 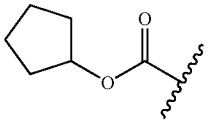 | 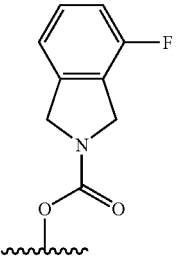 |
| 8 | 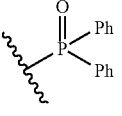 | | |

TABLE 3-continued
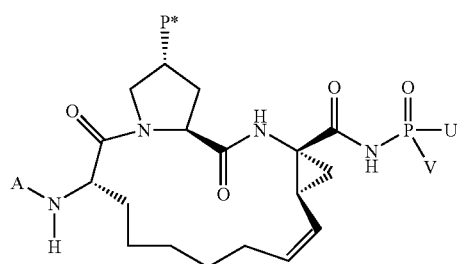
| Example # | A | P* | 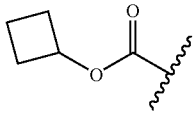 |
|---|---|---|---|
| 9 | 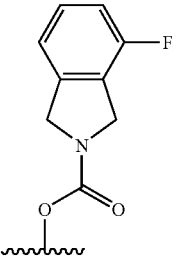 | 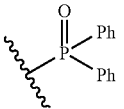 | 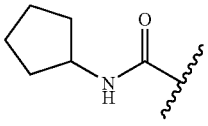 |
| 10 | 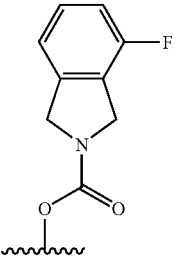 | 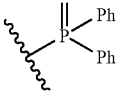 | 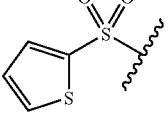 |
| 11 | 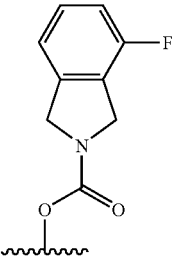 | 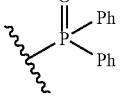 | 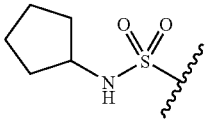 |
| 12 | 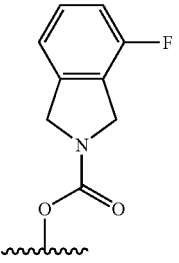 | 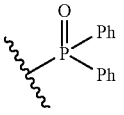 | |

TABLE 3-continued
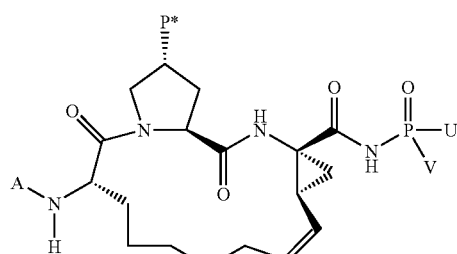
VII
| Example # | A | P* | 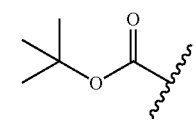 |
|---|---|---|---|
| 13 | 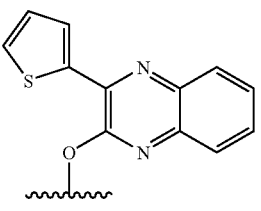 | 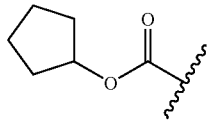 | 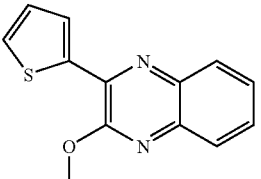 |
| 14 | 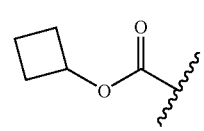 | 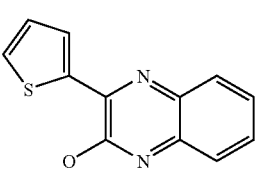 | 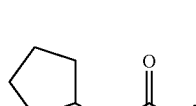 |
| 15 | 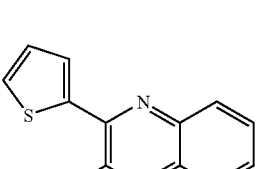 | 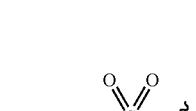 | 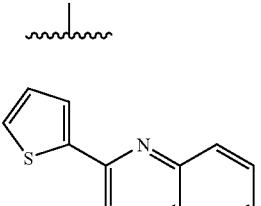 |
| 16 | | | |
| 17 | | | |

TABLE 3-continued
VII
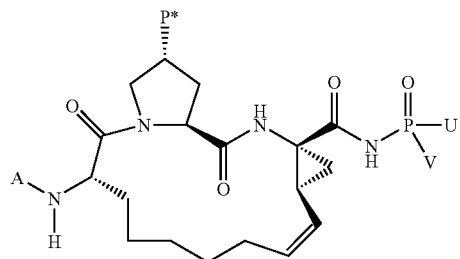
| Example # | A | P* |  |
|---|---|---|---|
| 18 | 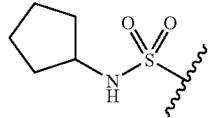 | 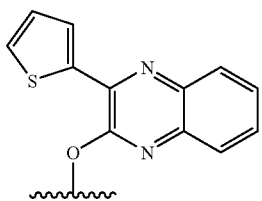 | 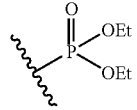 |
| 19 | 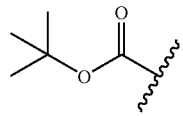 | 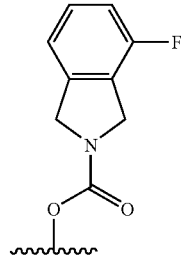 | 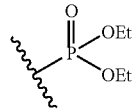 |
| 20 | 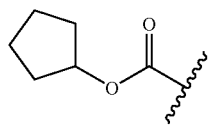 | 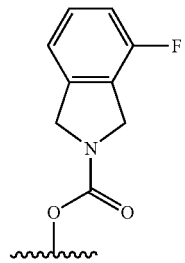 | 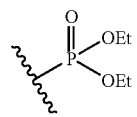 |
| 21 | 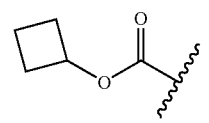 | 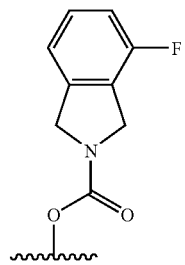 | 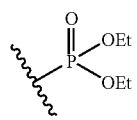 |

TABLE 3-continued
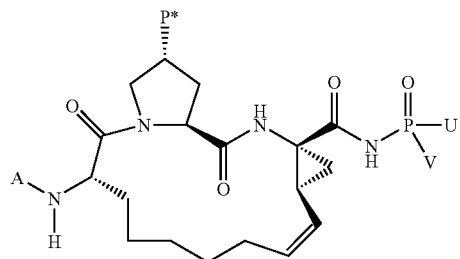
VII
| Example # | A | P* | 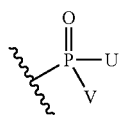 |
|---|---|---|---|
| 22 | 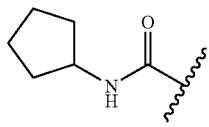 | 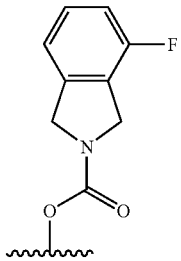 | 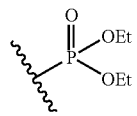 |
| 23 | 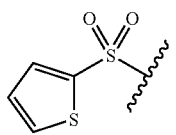 | 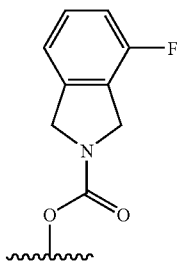 | 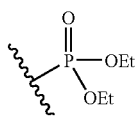 |
| 24 | 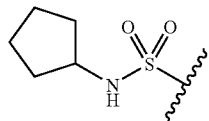 | 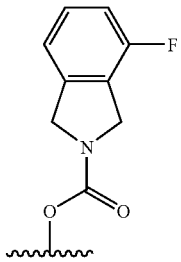 | 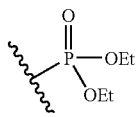 |
| 25 | 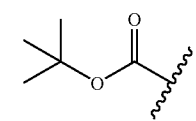 | 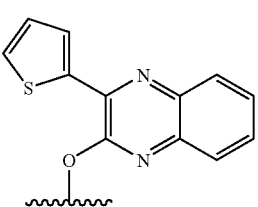 | 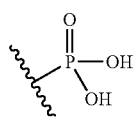 |

TABLE 3-continued
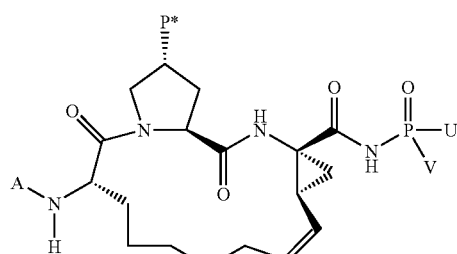
| Example # | A | P* | |
|---|---|---|---|
| 26 | 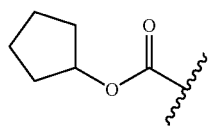 | 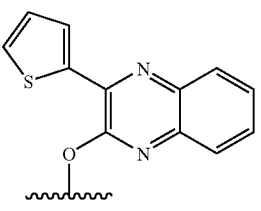 | 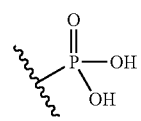 |
| 27 | 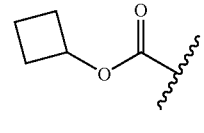 | 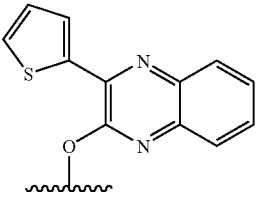 | 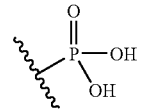 |
| 28 | 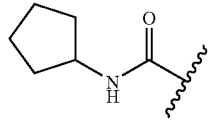 | 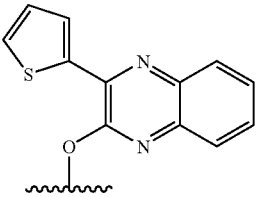 | 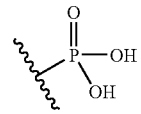 |
| 29 | 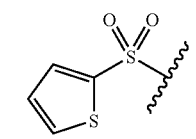 | 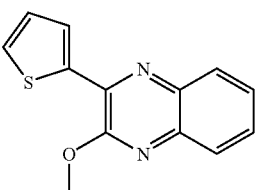 | 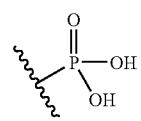 |
| 30 | 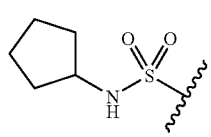 | 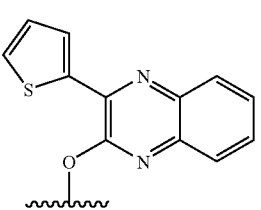 | 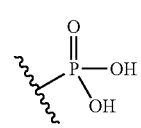 |

TABLE 3-continued
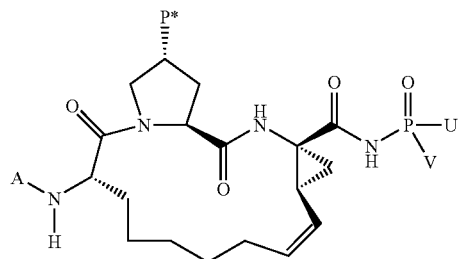
VII
| Example # | A | P* |  |
|---|---|---|---|
| 31 | 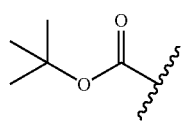 | 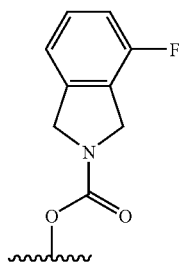 | 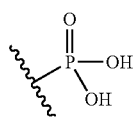 |
| 32 | 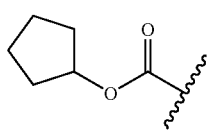 | 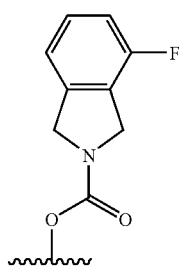 | 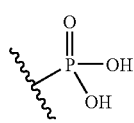 |
| 33 | 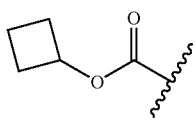 | 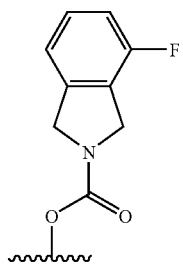 | 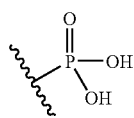 |
| 34 | 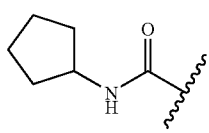 | 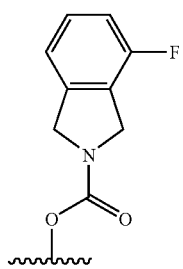 | 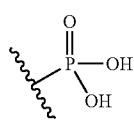 |

TABLE 3-continued

| Example # | A | P* | (phosphorus group) |
|---|---|---|---|
| 35 | thiophene-2-sulfonyl | 4-fluoroisoindoline-2-carbonyloxy | P(=O)(OH)(OH) |
| 36 | cyclopentylaminosulfonyl | 4-fluoroisoindoline-2-carbonyloxy | P(=O)(OH)(OH) |
| 37 | tert-butoxycarbonyl | 3-(thiophen-2-yl)quinoxalin-2-yloxy | P(=O)(OPh)(OPh) |
| 38 | cyclopentyloxycarbonyl | 3-(thiophen-2-yl)quinoxalin-2-yloxy | P(=O)(OMe)(OMe) |
| 39 | cyclobutoxycarbonyl | 3-(thiophen-2-yl)quinoxalin-2-yloxy | P(=O)(OPh)(OPh) |

TABLE 3-continued
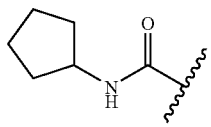
VII
| Example # | A | P* | 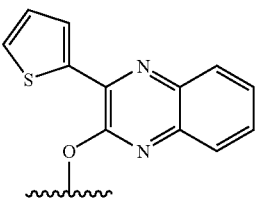 |
|---|---|---|---|
| 40 | 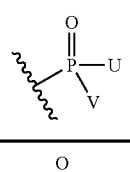 | 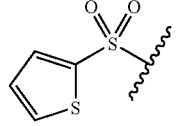 | 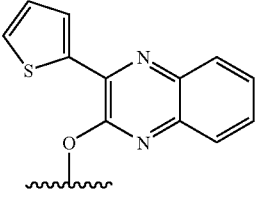 |
| 41 | 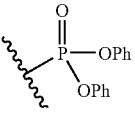 | 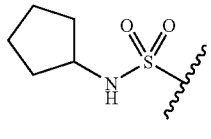 | 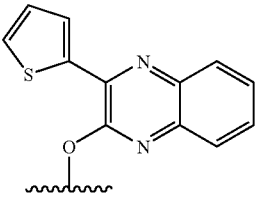 |
| 42 | 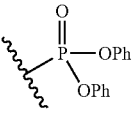 | 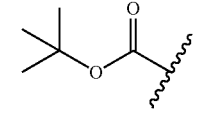 | 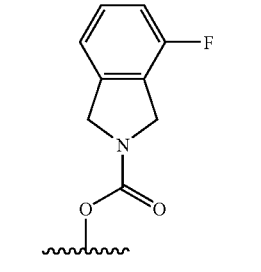 |
| 43 | 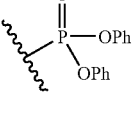 | 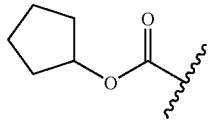 | 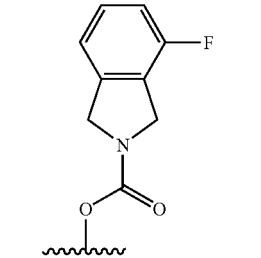 |
| 44 | 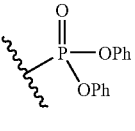 | | |

TABLE 3-continued
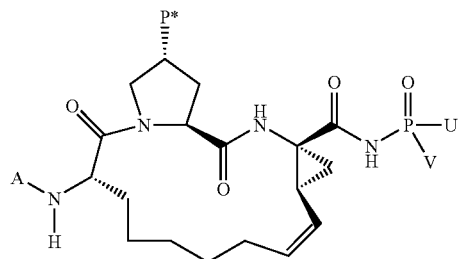
VII
| Example # | A | P* | 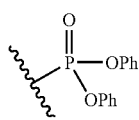 |
|---|---|---|---|
| 45 | 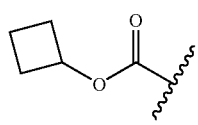 | 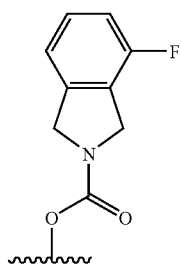 | 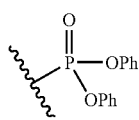 |
| 46 | 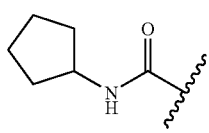 | 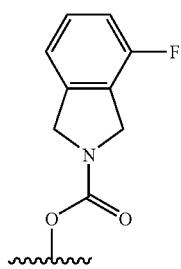 | 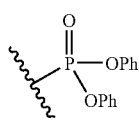 |
| 47 | 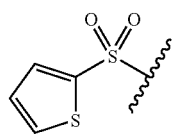 | 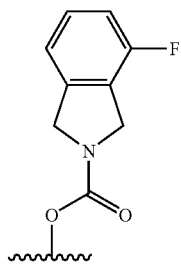 | 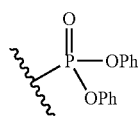 |
| 48 | 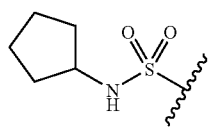 | 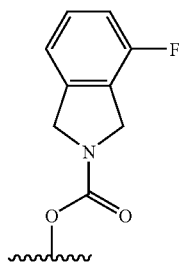 | 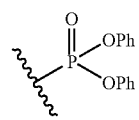 |

TABLE 3-continued
VII
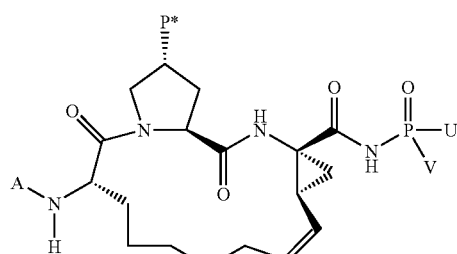
| Example # | A | P* | 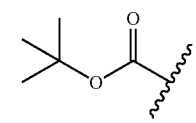 |
|---|---|---|---|
| 49 | 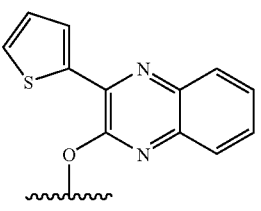 | 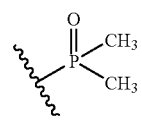 | 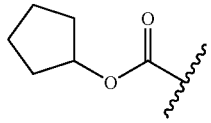 |
| 50 | 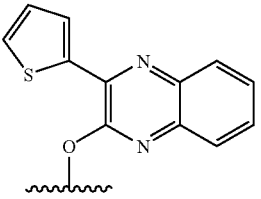 | 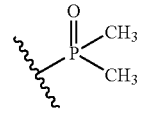 | 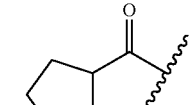 |
| 51 | 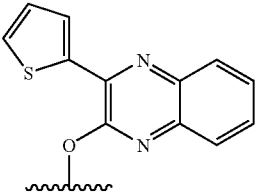 | 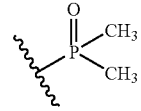 | 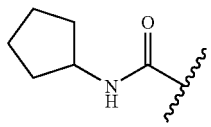 |
| 52 | 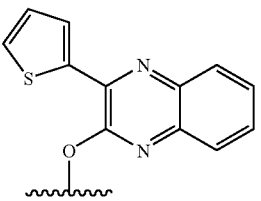 | 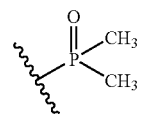 | 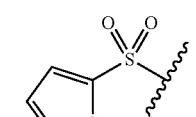 |
| 53 | 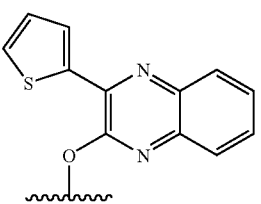 | 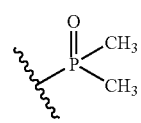 | |

TABLE 3-continued
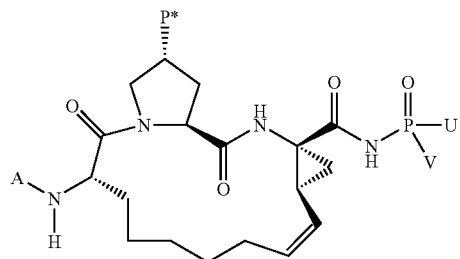
VII
| Example # | A | P* | 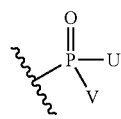 |
|---|---|---|---|
| 54 | 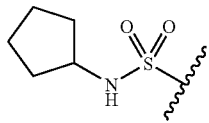 | 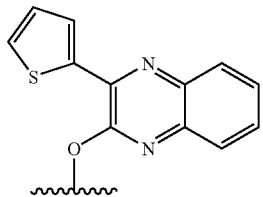 | 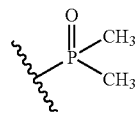 |
| 55 | 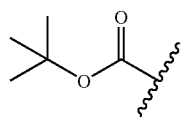 | 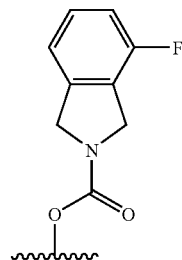 | 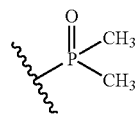 |
| 56 | 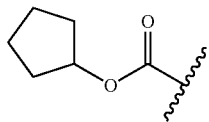 | 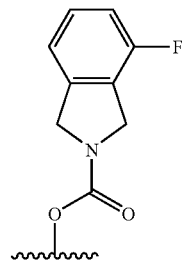 | 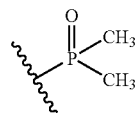 |
| 57 | 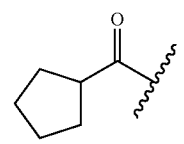 | 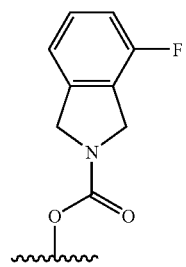 | 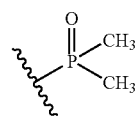 |

TABLE 3-continued
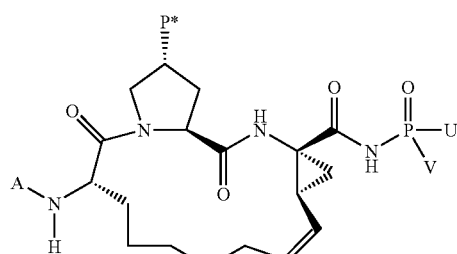
VII
| Example # | A | P* | 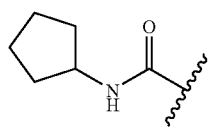 |
|---|---|---|---|
| 58 | 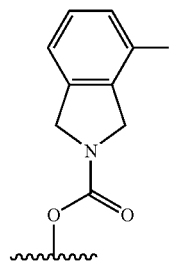 | 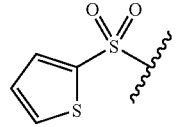 | 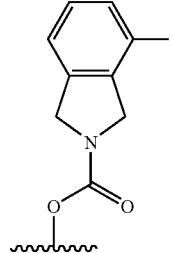 |
| 59 | 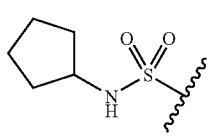 | 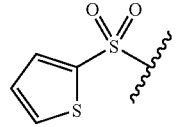 | 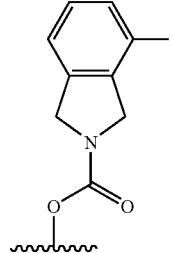 |
| 60 | 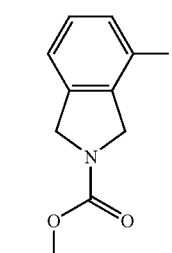 | 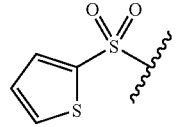 | 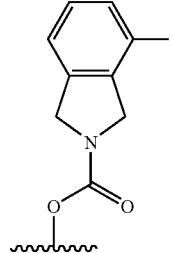 |
| 61 | 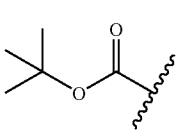 | 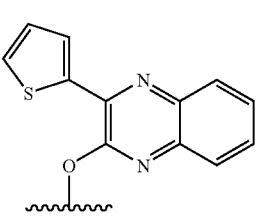 | |

TABLE 3-continued

Structure VII: macrocyclic compound with substituents A, P*, and phosphonate group (P with U, V, =O).

| Example # | A | P* | (phosphonate group) |
|---|---|---|---|
| 62 | cyclopentyl ester (cyclopentyl-O-C(=O)-) | 3-(thiophen-2-yl)quinoxalin-2-yloxy | diisopropyl phosphonate |
| 63 | cyclopentyl ketone (cyclopentyl-C(=O)-) | 3-(thiophen-2-yl)quinoxalin-2-yloxy | diisopropyl phosphonate |
| 64 | N-cyclopentyl amide (cyclopentyl-NH-C(=O)-) | 3-(thiophen-2-yl)quinoxalin-2-yloxy | diisopropyl phosphonate |
| 65 | thiophene-2-sulfonyl | 3-(thiophen-2-yl)quinoxalin-2-yloxy | diisopropyl phosphonate |
| 66 | N-cyclopentyl sulfamoyl (cyclopentyl-NH-S(=O)$_2$-) | 3-(thiophen-2-yl)quinoxalin-2-yloxy | diisopropyl phosphonate |

TABLE 3-continued
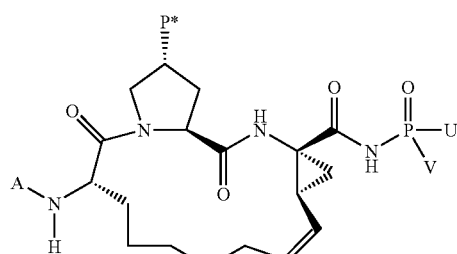
VII
| Example # | A | P* | 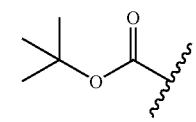 |
|---|---|---|---|
| 67 | 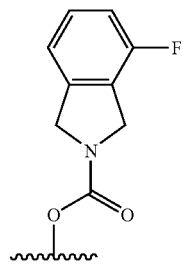 | 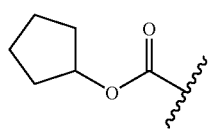 | 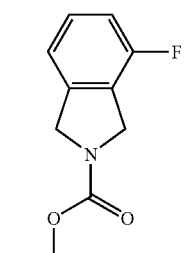 |
| 68 | 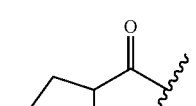 | 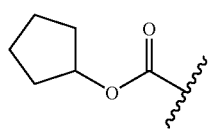 | 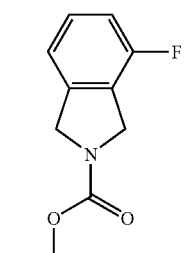 |
| 69 | 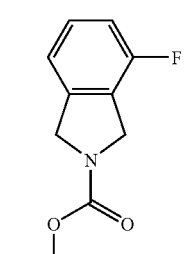 | 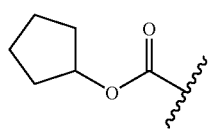 | 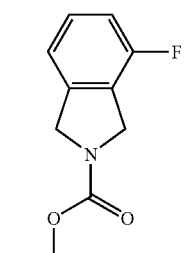 |
| 70 | 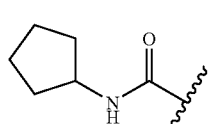 | 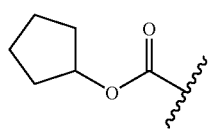 | 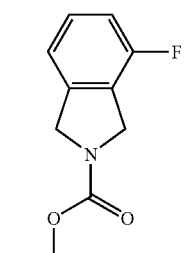 |

TABLE 3-continued (Structure VII: macrocyclic compound with substituents A, P*, and phosphorus group with U, V)

| Example # | A | P* | (phosphoryl group with U, V) |
|---|---|---|---|
| 71 | 2-thienylsulfonyl | 4-fluoro-isoindoline-2-carbonyloxy | P(=O)(O-iPr)(O-iPr) |
| 72 | cyclopentyl-NH-SO₂- | 4-fluoro-isoindoline-2-carbonyloxy | P(=O)(O-iPr)(O-iPr) |
| 73 | tert-butoxycarbonyl | 3-(thiophen-2-yl)quinoxalin-2-yloxy | phospholane 1-oxide |
| 74 | cyclopentyloxycarbonyl | 3-(thiophen-2-yl)quinoxalin-2-yloxy | phospholane 1-oxide |
| 75 | cyclopentylcarbonyl | 3-(thiophen-2-yl)quinoxalin-2-yloxy | phospholane 1-oxide |

TABLE 3-continued
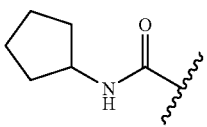
| Example # | A | P* | |
|---|---|---|---|
| 76 | 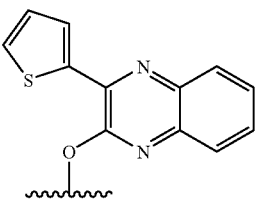 | 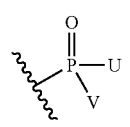 | 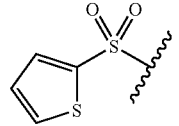 |
| 77 | 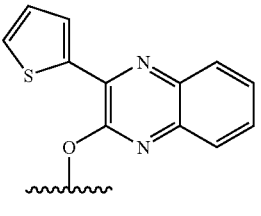 | 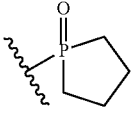 | 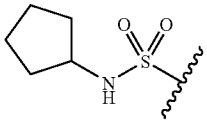 |
| 78 | 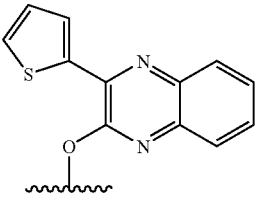 | 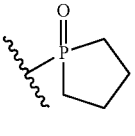 | 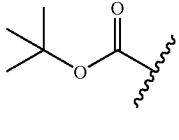 |
| 79 | 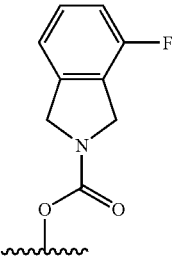 | 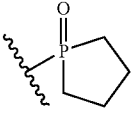 | 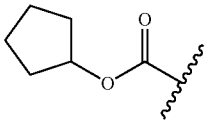 |
| 80 | 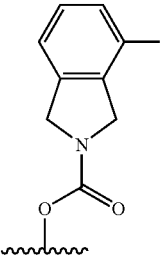 | 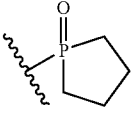 | |

TABLE 3-continued
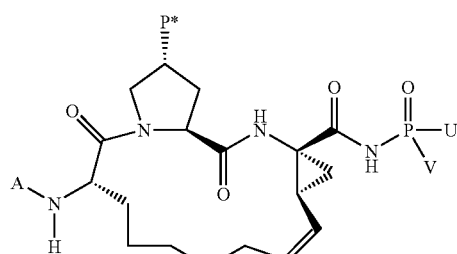
VII
| Example # | A | P* | 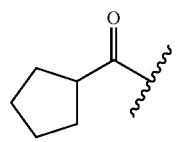 |
|---|---|---|---|
| 81 | 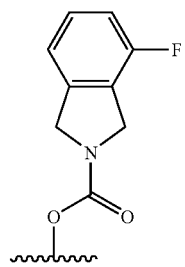 | 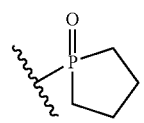 | 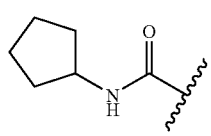 |
| 82 | 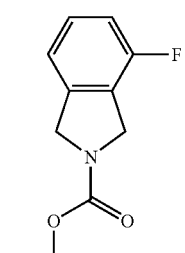 | 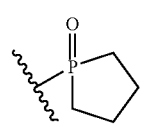 | 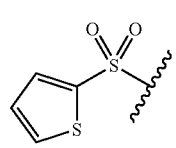 |
| 83 | 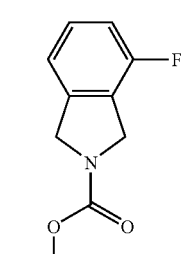 | 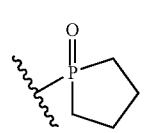 | 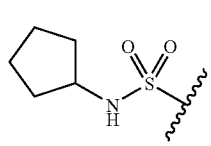 |
| 84 | 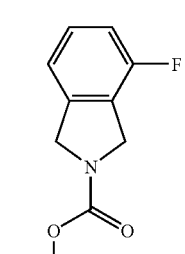 | 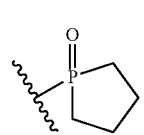 | |

TABLE 3-continued

VII

| Example # | A | P* | (O=P(U)(V)) |
|---|---|---|---|
| 85 | tert-butyl ester | 3-(thiophen-2-yl)quinoxalin-2-yloxy | dicyclopentyl phosphonate |
| 86 | cyclopentyl ester | 3-(thiophen-2-yl)quinoxalin-2-yloxy | dicyclopentyl phosphonate |
| 87 | cyclopentyl ketone | 3-(thiophen-2-yl)quinoxalin-2-yloxy | dicyclopentyl phosphonate |
| 88 | cyclopentyl amide | 3-(thiophen-2-yl)quinoxalin-2-yloxy | dicyclopentyl phosphonate |
| 89 | thiophen-2-ylsulfonyl | 3-(thiophen-2-yl)quinoxalin-2-yloxy | dicyclopentyl phosphonate |

TABLE 3-continued
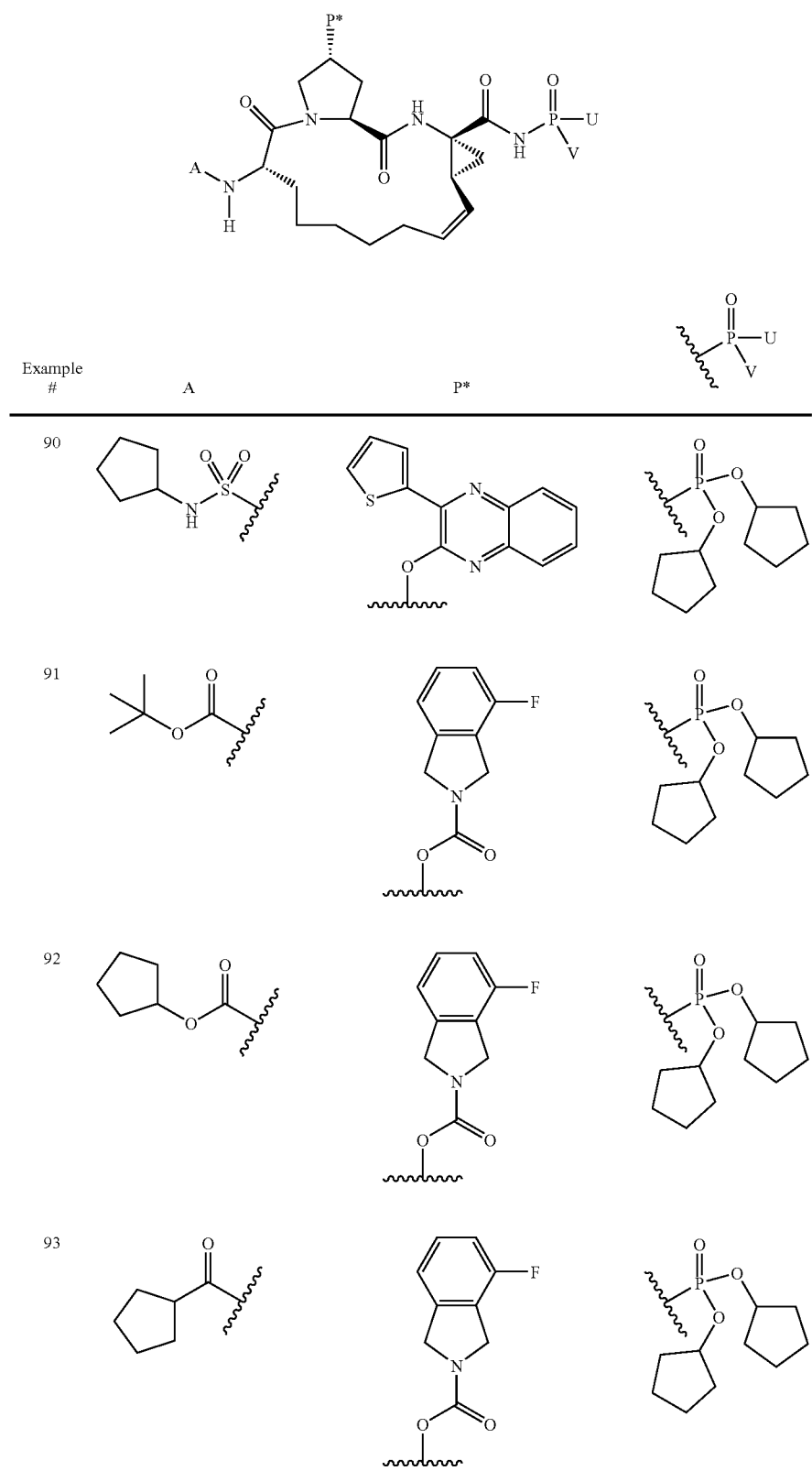

TABLE 3-continued
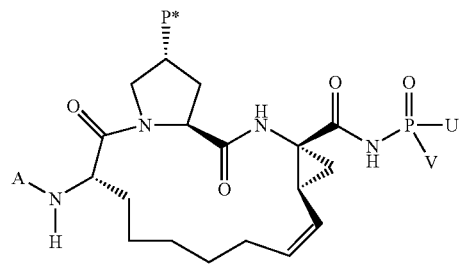
VII
| Example # | A | P* |  |
|---|---|---|---|
| 94 | 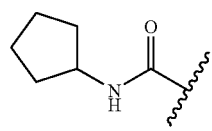 | 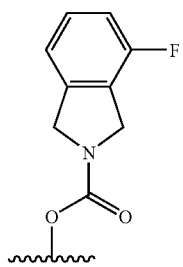 | 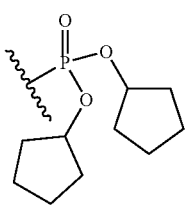 |
| 95 | 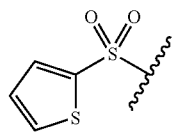 | 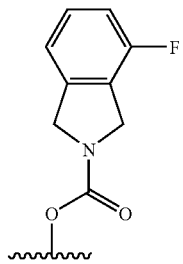 | 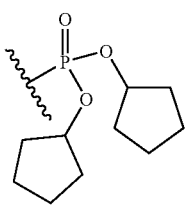 |
| 96 | 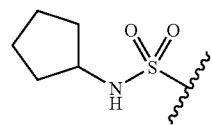 | 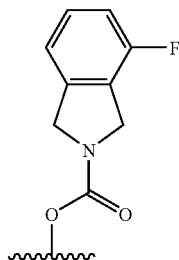 | 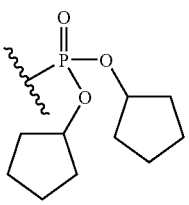 |
| 97 | 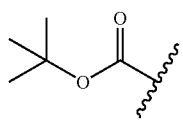 | 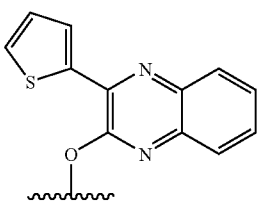 | 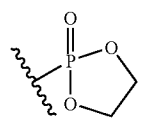 |

TABLE 3-continued
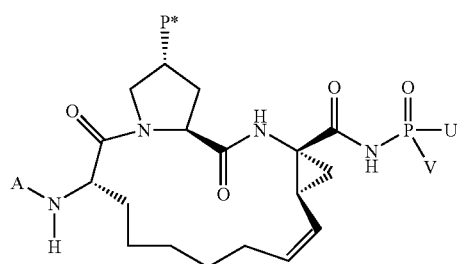
| Example # | A | P* | 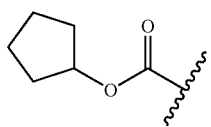 |
|---|---|---|---|
| 98 | 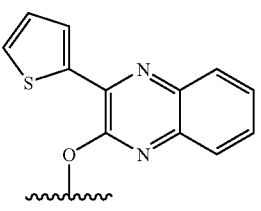 | 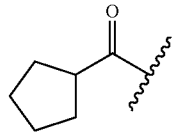 | 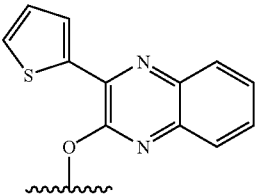 |
| 99 | 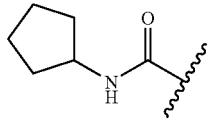 | | |
| 100 | 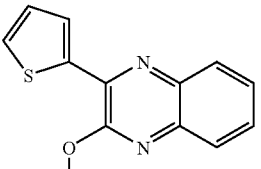 | | |
| 101 | 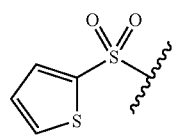 | | |
| 102 | 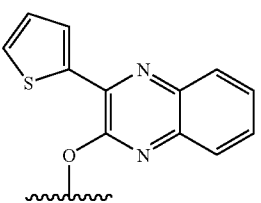 | | |

TABLE 3-continued
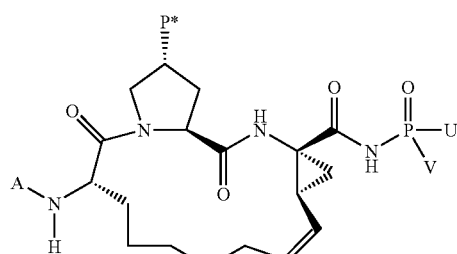
| Example # | A | P* | 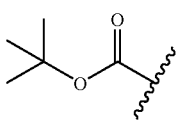 |
|---|---|---|---|
| 103 | 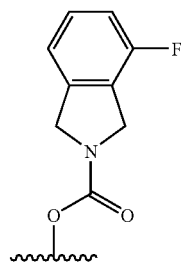 | 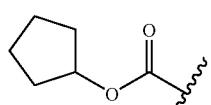 | 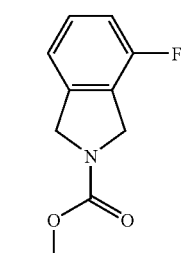 |
| 104 | 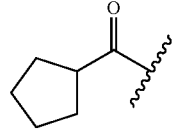 | 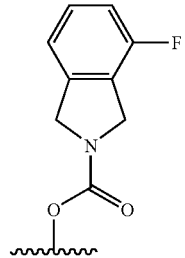 | 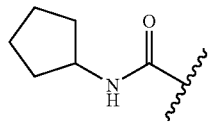 |
| 105 | 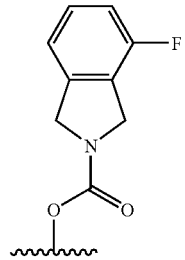 | | |
| 106 | | | |

TABLE 3-continued
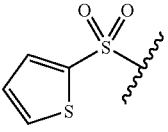
| Example # | A | P* | |
|---|---|---|---|
| 107 | 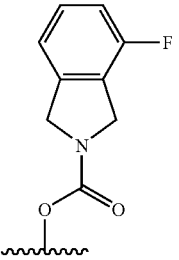 | 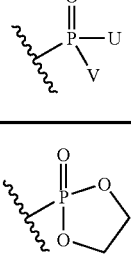 | 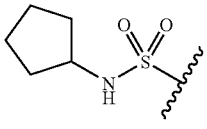 |
| 108 | 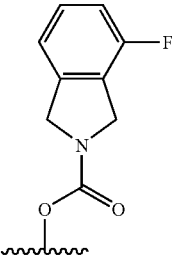 | 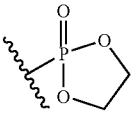 | 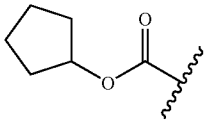 |
| 109 | 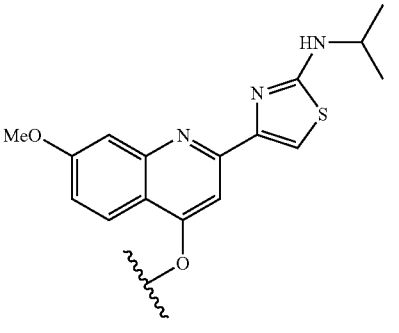 | 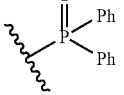 | 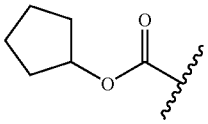 |
| 110 | 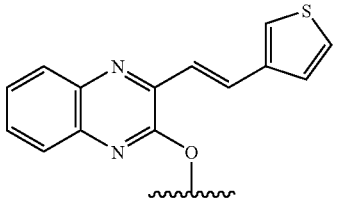 | 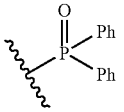 | |

TABLE 3-continued
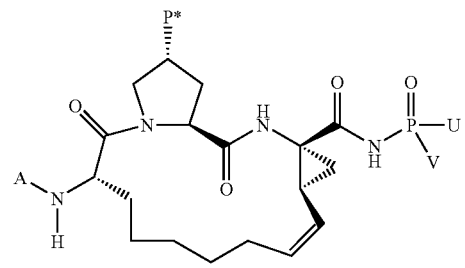
VII
| Example # | A | P* | 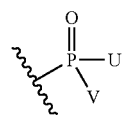 |
|---|---|---|---|
| 111 | 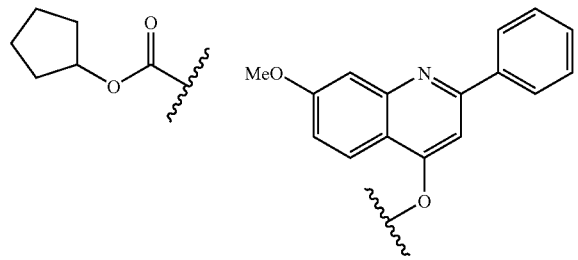 | | 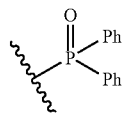 |
| 112 | 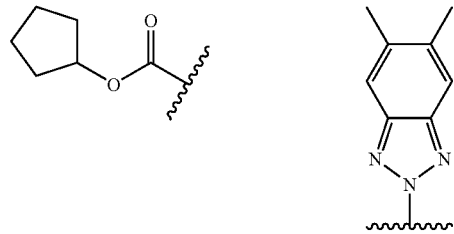 | | 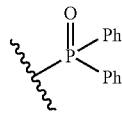 |
| 113 | 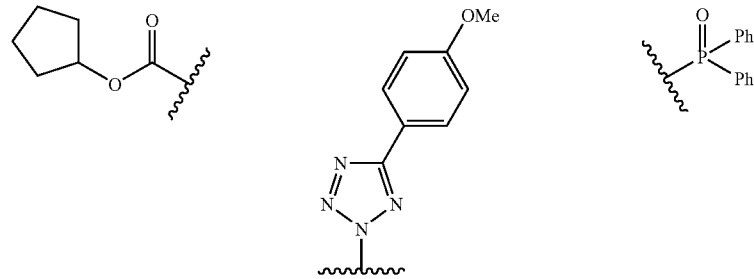 | | 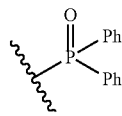 |

…
Examples 114-226
(Formula VIII, Table 4) may be prepared following procedures similar to those outlined in Examples 1-5 using the acyclic tripeptide.
TABLE 4
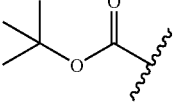
| Example # | A | P* | 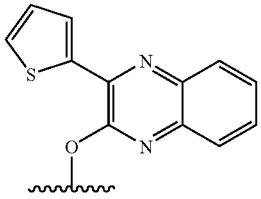 | L |
|---|---|---|---|---|
| 114 | 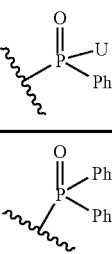 |  |  | 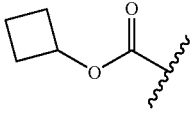 |
| 115 | 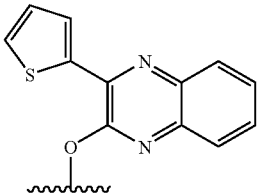 | 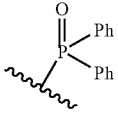 |  |  |
| 116 | 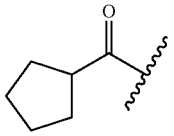 | 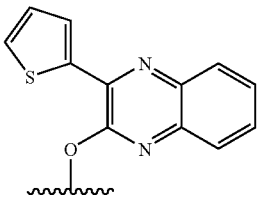 | 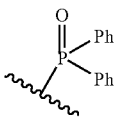 |  |
| 117 |  | 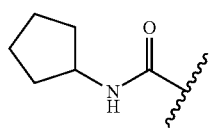 | 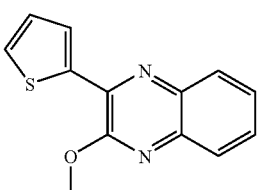 | 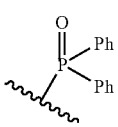 |
| 118 |  |  | 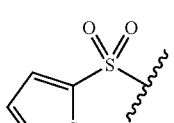 | 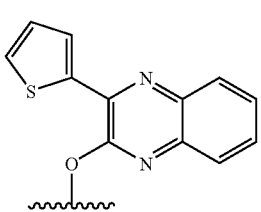 |

TABLE 4-continued

| Example # | A | P* | (phosphorus group) | L |
|---|---|---|---|---|
| 119 | cyclopentyl-NH-SO2- | 2-thienyl-quinoxalin-3-yloxy | P(=O)(Ph)(Ph) | tert-butyl |
| 120 | tert-butyl-O-C(=O)- | 4-fluoro-isoindoline-2-carboxylate-O- | P(=O)(Ph)(Ph) | tert-butyl |
| 121 | cyclopentyl-O-C(=O)- | 4-fluoro-isoindoline-2-carboxylate-O- | P(=O)(Ph)(Ph) | tert-butyl |
| 122 | cyclobutyl-O-C(=O)- | 4-fluoro-isoindoline-2-carboxylate-O- | P(=O)(Ph)(Ph) | tert-butyl |

TABLE 4-continued
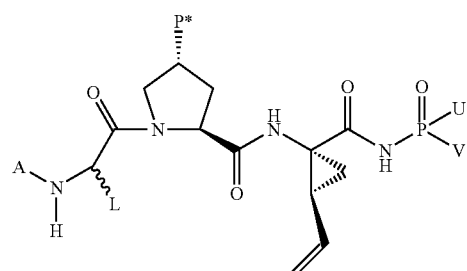
| Example # | A | P* | 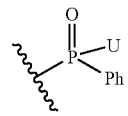 | L |
|---|---|---|---|---|
| 123 | 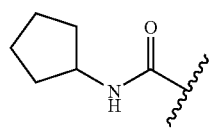 | 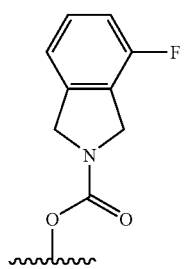 | 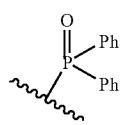 | 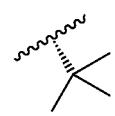 |
| 124 | 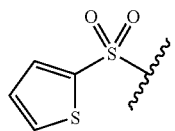 | 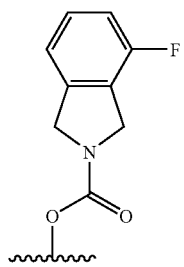 | 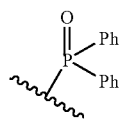 | 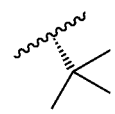 |
| 125 | 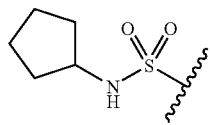 | 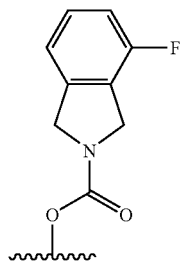 | 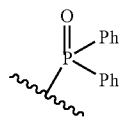 | 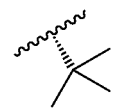 |
| 126 | 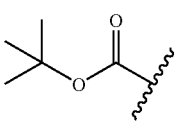 | 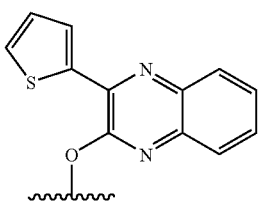 | 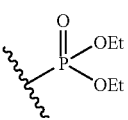 | 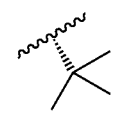 |

TABLE 4-continued
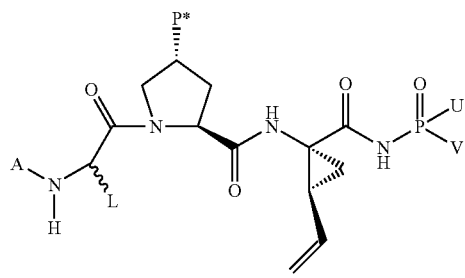
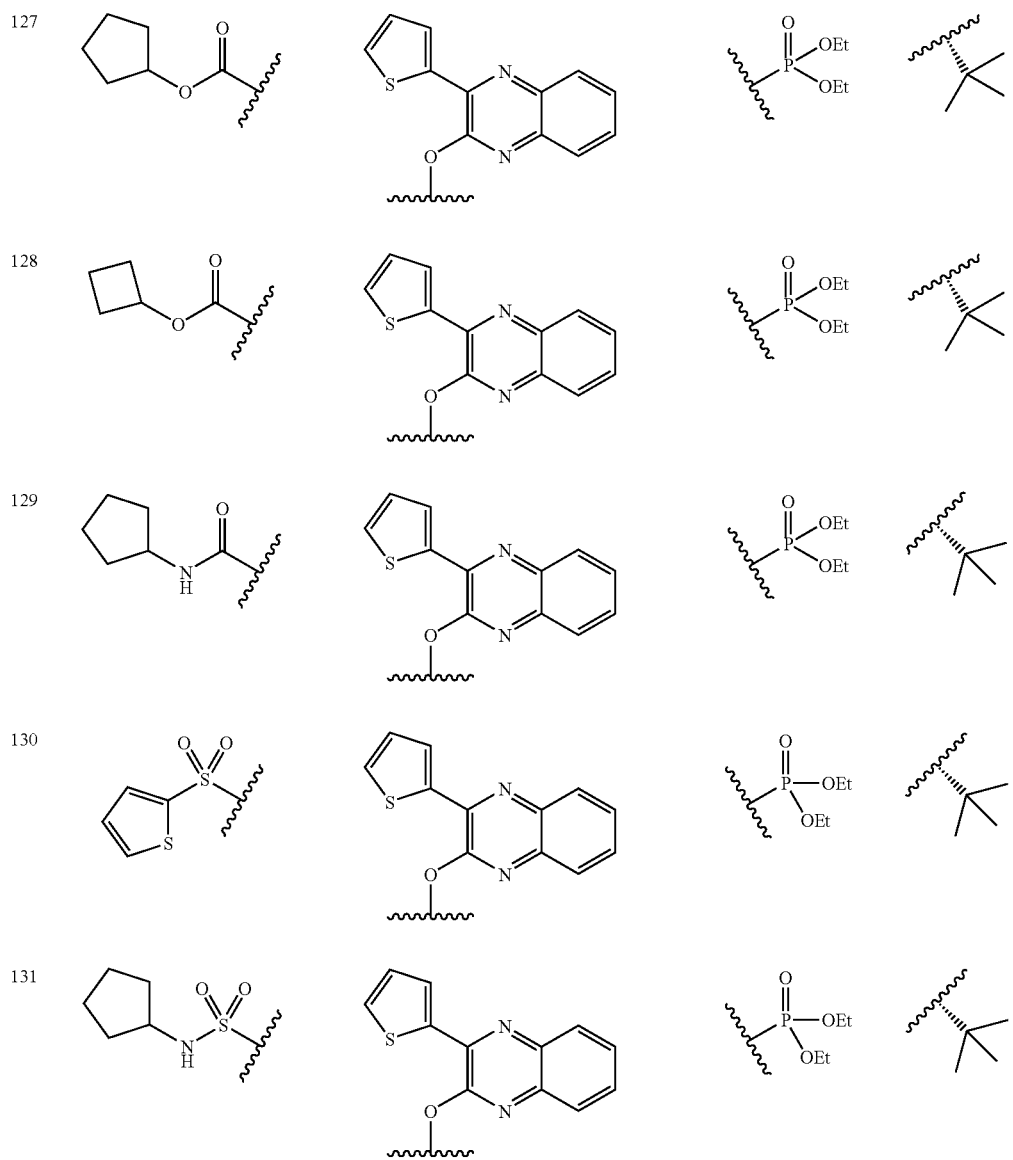

TABLE 4-continued

VIII

| Example # | A | P* | | L |
|---|---|---|---|---|
| 132 | tert-butyl ester | 4-F isoindoline-N-carboxylate | P(=O)(OEt)(OEt) | tert-butyl |
| 133 | cyclopentyl ester | 4-F isoindoline-N-carboxylate | P(=O)(OEt)(OEt) | tert-butyl |
| 134 | cyclobutyl ester | 4-F isoindoline-N-carboxylate | P(=O)(OEt)(OEt) | tert-butyl |
| 135 | cyclopentyl amide | 4-F isoindoline-N-carboxylate | P(=O)(OEt)(OEt) | tert-butyl |

TABLE 4-continued

| Example # | A | P* | | L |
|---|---|---|---|---|
| 136 | thiophene-2-sulfonyl | 4-fluoro-isoindoline-N-carboxy-O- | OEt, OEt | tert-butyl |
| 137 | cyclopentyl-NH-sulfonyl | 4-fluoro-isoindoline-N-carboxy-O- | OEt, OEt | tert-butyl |
| 138 | tert-butyl ester | 3-(thien-2-yl)quinoxalin-2-yloxy | OH, OH | tert-butyl |
| 139 | cyclopentyl ester | 3-(thien-2-yl)quinoxalin-2-yloxy | OH, OH | tert-butyl |
| 140 | cyclopentyl ketone | 3-(thien-2-yl)quinoxalin-2-yloxy | OH, OH | tert-butyl |

TABLE 4-continued

| Example # | A | P* | [P(O)(U)(Ph)] | L |
|---|---|---|---|---|
| 141 | cyclopentyl-NH-C(O)- | 2-thienyl-quinoxalin-3-yloxy | P(O)(OH)(OH) | tert-butyl |
| 142 | 2-thienyl-SO₂- | 2-thienyl-quinoxalin-3-yloxy | P(O)(OH)(OH) | tert-butyl |
| 143 | cyclopentyl-NH-SO₂- | 2-thienyl-quinoxalin-3-yloxy | P(O)(OH)(OH) | tert-butyl |
| 144 | tert-butyl-O-C(O)- | 4-fluoro-isoindolin-2-yl-C(O)-O- | P(O)(OH)(OH) | tert-butyl |
| 145 | cyclopentyl-O-C(O)- | 4-fluoro-isoindolin-2-yl-C(O)-O- | P(O)(OH)(OH) | tert-butyl |

TABLE 4-continued
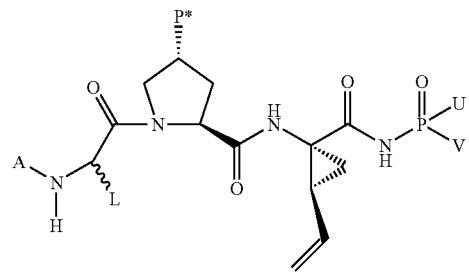
| Example # | A | P* | 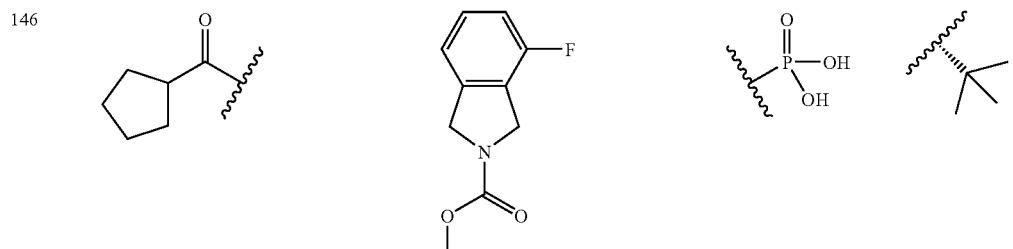 | L |
|---|---|---|---|---|
| 146 | | | 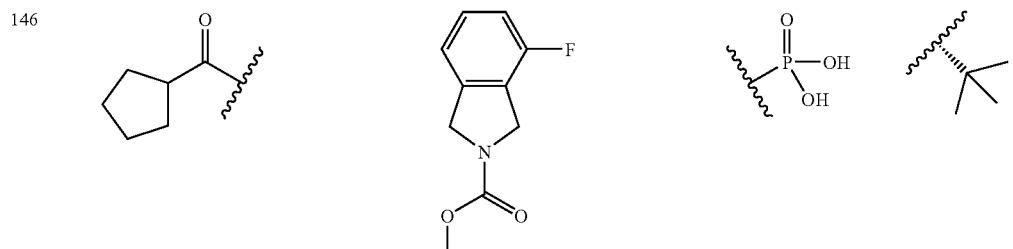 | |
| 147 | | | 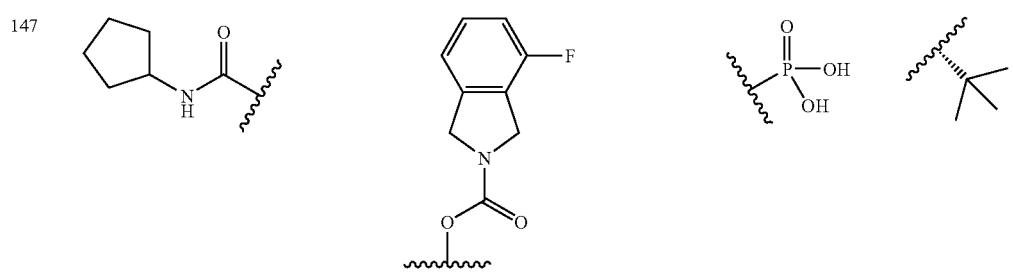 | |
| 148 | | | 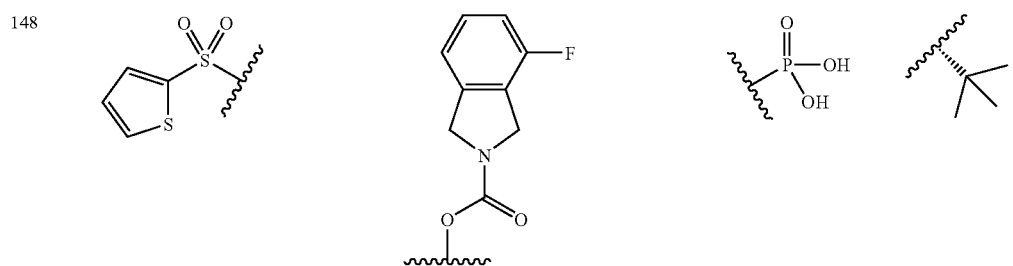 | |
| 149 | | | 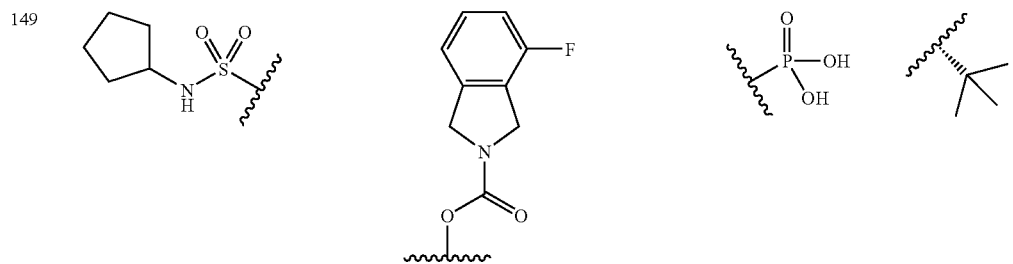 | |

TABLE 4-continued
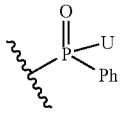
VIII
| Example # | A | P* |  | L |
|---|---|---|---|---|
| 150 | 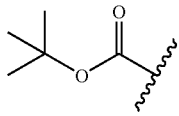 | 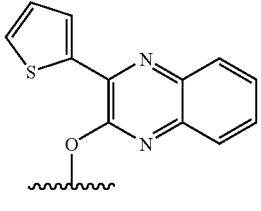 | 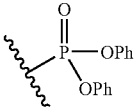 |  |
| 151 | 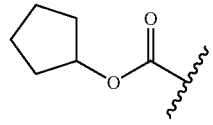 | 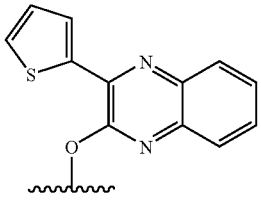 | 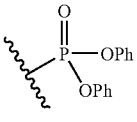 |  |
| 152 | 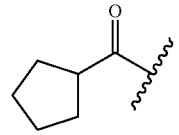 | 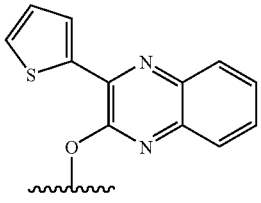 | 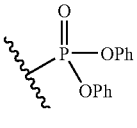 |  |
| 153 | 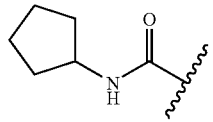 | 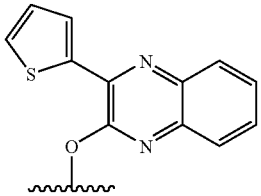 | 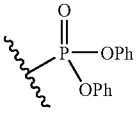 |  |
| 154 | 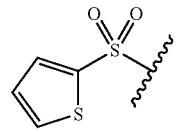 | 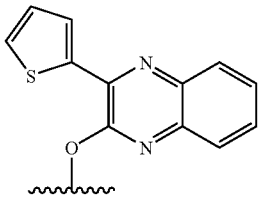 | 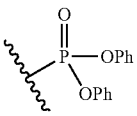 |  |

TABLE 4-continued
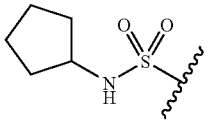
| Example # | A | P* | 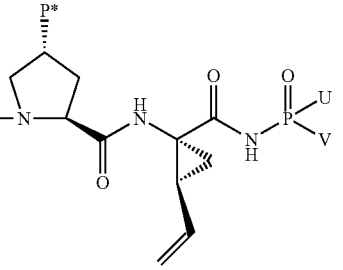 | L |
|---|---|---|---|---|
| 155 | 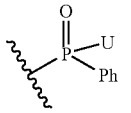 |  | 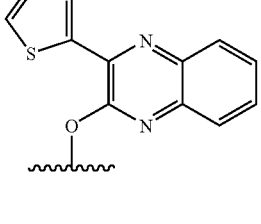 | 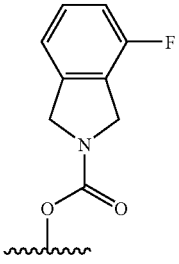 |
| 156 | 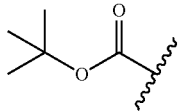 | 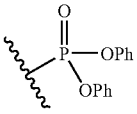 |  | 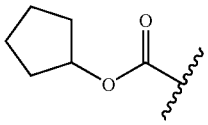 |
| 157 | 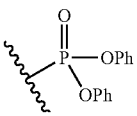 |  | 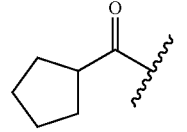 | 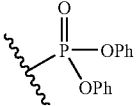 |
| 158 |  | | | |

TABLE 4-continued
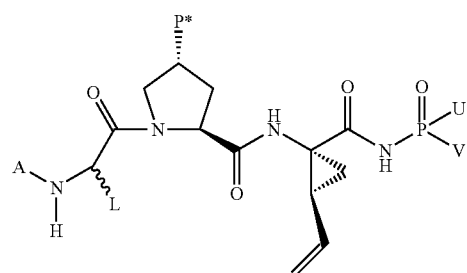
VIII
| Example # | A | P* | 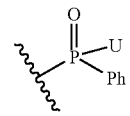 | L |
|---|---|---|---|---|
| 159 | 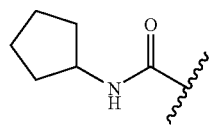 | 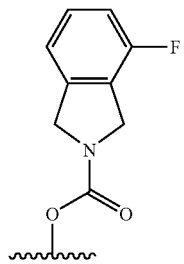 | 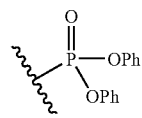 | 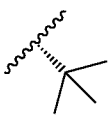 |
| 160 | 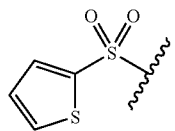 | 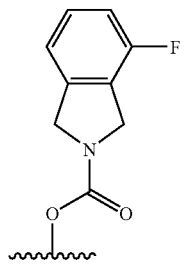 | 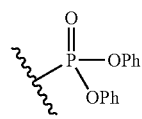 | 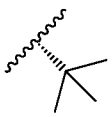 |
| 161 | 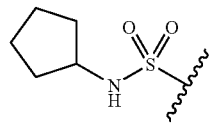 | 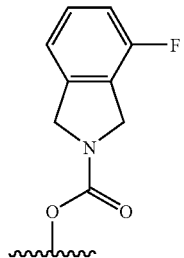 | 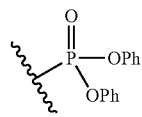 | 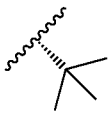 |
| 162 | 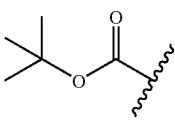 | 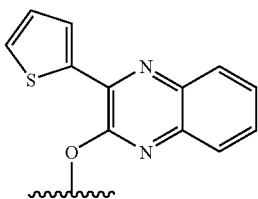 | 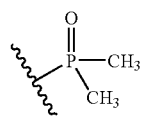 | 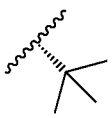 |

TABLE 4-continued

VIII

| Example # | A | P* | | L |
|---|---|---|---|---|
| 163 | cyclopentyl ester | thiophene-quinoxaline-O | P(=O)(CH₃)(CH₃) | tert-butyl |
| 164 | cyclopentyl ketone | thiophene-quinoxaline-O | P(=O)(CH₃)(CH₃) | tert-butyl |
| 165 | cyclopentyl amide | thiophene-quinoxaline-O | P(=O)(CH₃)(CH₃) | tert-butyl |
| 166 | thiophene sulfonyl | thiophene-quinoxaline-O | P(=O)(CH₃)(CH₃) | tert-butyl |
| 167 | cyclopentyl sulfamide | thiophene-quinoxaline-O | P(=O)(CH₃)(CH₃) | tert-butyl |

TABLE 4-continued

| Example # | A | P* | | L |
|---|---|---|---|---|
| 168 | tert-butyl ester | 4-F isoindoline-N-carboxylate | P(=O)(CH3)(CH3) | t-Bu |
| 169 | cyclopentyl ester | 4-F isoindoline-N-carboxylate | P(=O)(CH3)(CH3) | t-Bu |
| 170 | cyclopentyl ketone | 4-F isoindoline-N-carboxylate | P(=O)(CH3)(CH3) | t-Bu |
| 171 | cyclopentyl amide | 4-F isoindoline-N-carboxylate | P(=O)(CH3)(CH3) | t-Bu |

TABLE 4-continued
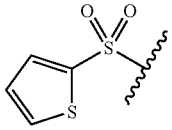
| Example # | A | P* | 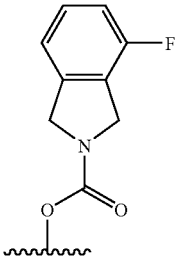 | L |
|---|---|---|---|---|
| 172 | 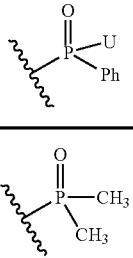 |  | 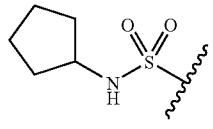 | 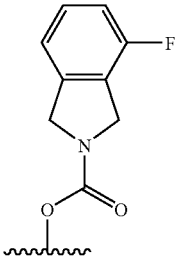 |
| 173 | 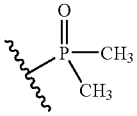 |  | 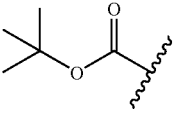 | 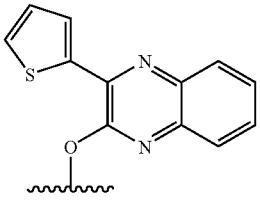 |
| 174 | 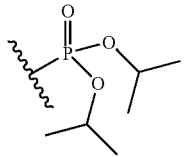 |  | 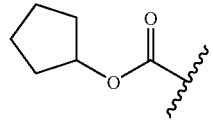 | 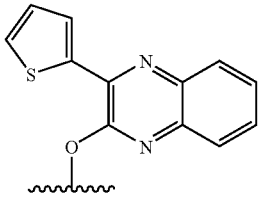 |
| 175 | 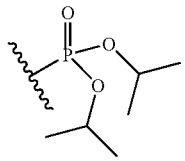 | 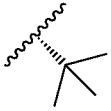 | 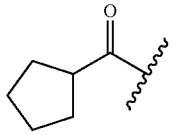 | 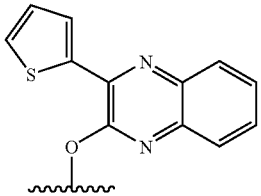 |
| 176 | 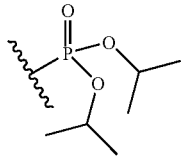 |  | | |

TABLE 4-continued

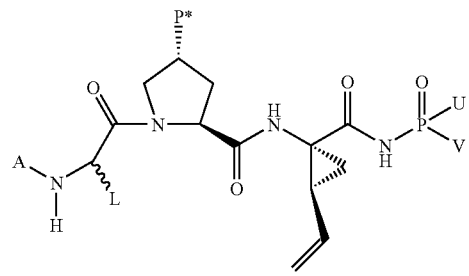

VIII

| Example # | A | P* | <br>(phosphorus group with U and Ph) | L |
|---|---|---|---|---|
| 177 | cyclopentyl-NH-C(O)- | 3-(thiophen-2-yl)quinoxalin-2-yloxy | -P(O)(OiPr)₂ | tert-butyl |
| 178 | thiophen-2-yl-SO₂- | 3-(thiophen-2-yl)quinoxalin-2-yloxy | -P(O)(OiPr)₂ | tert-butyl |
| 179 | cyclopentyl-NH-S(O)₂- | 3-(thiophen-2-yl)quinoxalin-2-yloxy | -P(O)(OiPr)₂ | tert-butyl |
| 180 | tert-butyl-O-C(O)- | 7-fluoroisoindolin-2-yl-C(O)O- | -P(O)(OiPr)₂ | tert-butyl |
| 181 | cyclopentyl-O-C(O)- | 7-fluoroisoindolin-2-yl-C(O)O- | -P(O)(OiPr)₂ | tert-butyl |

TABLE 4-continued
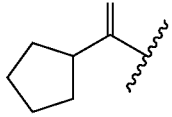
| Example # | A | P* | | L |
|---|---|---|---|---|
| 182 | 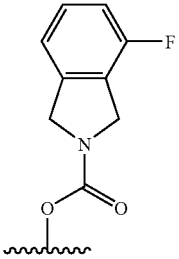 | 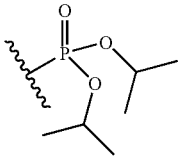 |  | 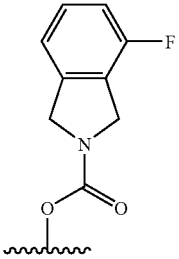 |
| 183 | 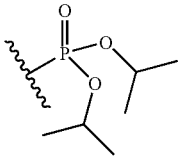 |  | 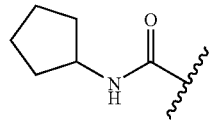 | 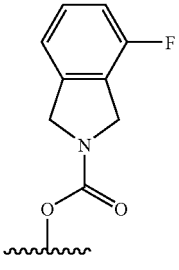 |
| 184 | 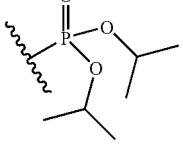 |  | 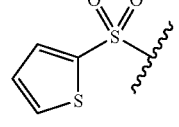 | 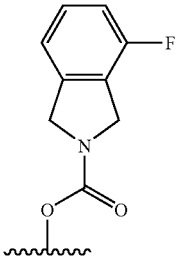 |
| 185 | 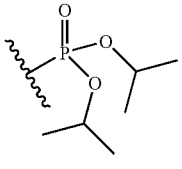 |  | 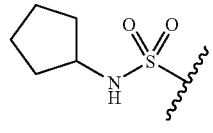 | 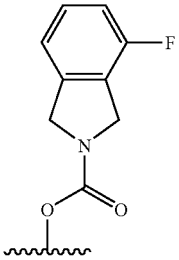 |

TABLE 4-continued

VIII

| Example # | A | P* | | L |
|---|---|---|---|---|
| 186 | tert-butyl ester | 2-thienyl-quinoxalinyloxy | phospholane oxide | tert-butyl |
| 187 | cyclopentyl ester | 2-thienyl-quinoxalinyloxy | phospholane oxide | tert-butyl |
| 188 | cyclopentyl ketone | 2-thienyl-quinoxalinyloxy | phospholane oxide | tert-butyl |
| 189 | cyclopentyl amide | 2-thienyl-quinoxalinyloxy | phospholane oxide | tert-butyl |
| 190 | 2-thienylsulfonyl | 2-thienyl-quinoxalinyloxy | phospholane oxide | tert-butyl |

TABLE 4-continued
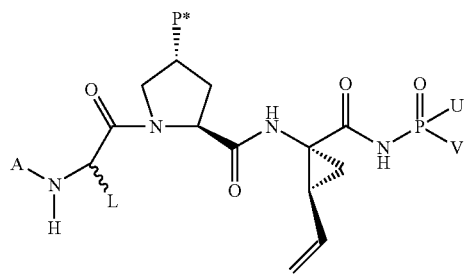
VIII
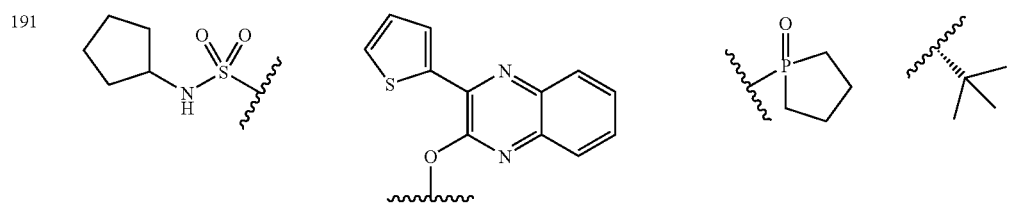
| Example # | A | P* | 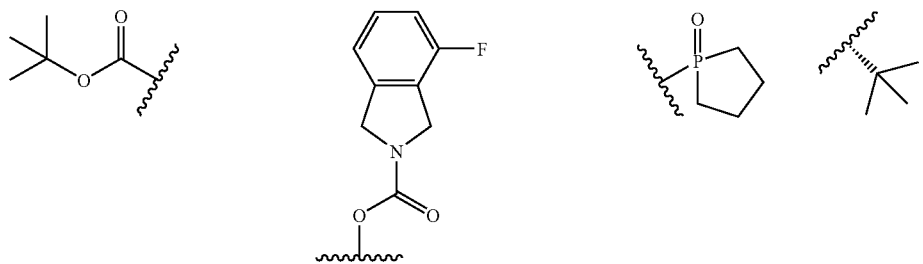 | L |
|---|---|---|---|---|
191
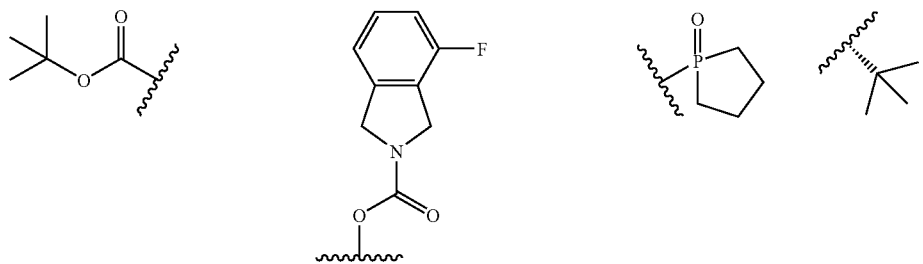
192
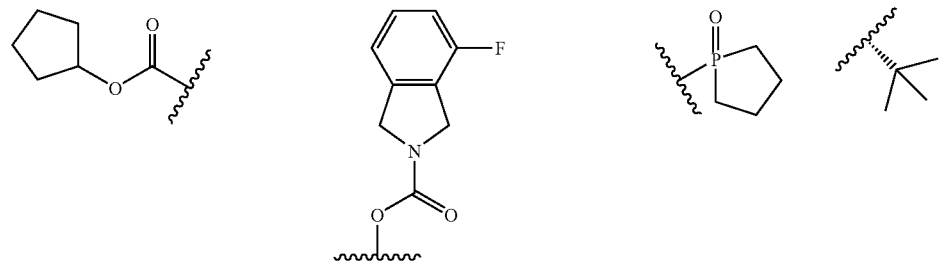
193
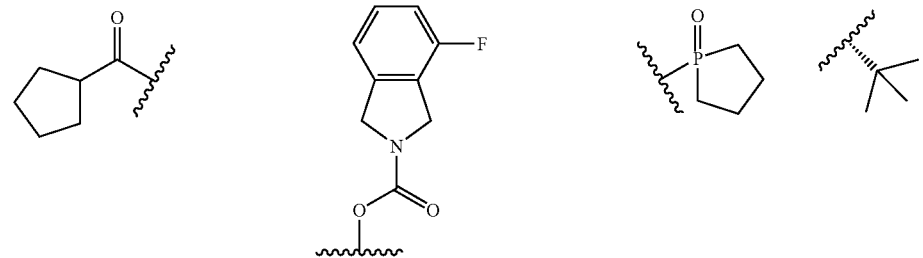
194

TABLE 4-continued
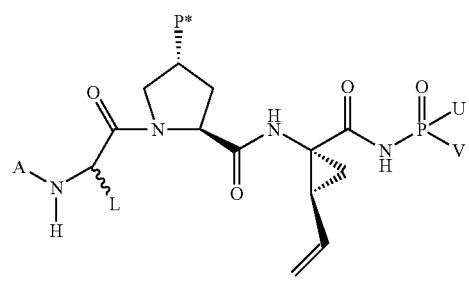
VIII
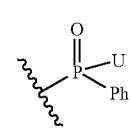
| Example # | A | P* | | L |
|---|---|---|---|---|
| 195 | 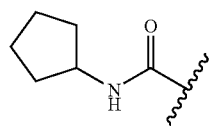 | 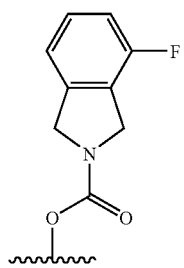 | | |
| 196 | 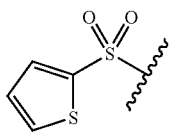 | 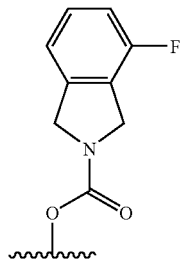 | 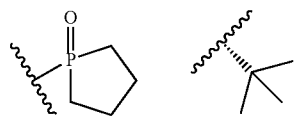 | |
| 197 | 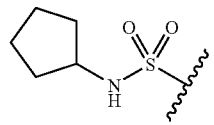 | 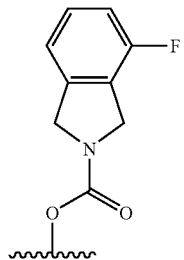 | 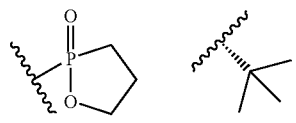 | |
| 198 | 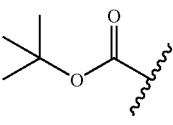 | 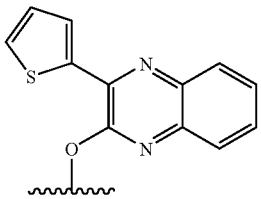 | 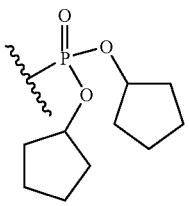 | |

TABLE 4-continued

VIII

| Example # | A | P* | | L |
|---|---|---|---|---|
| 199 | cyclopentyl ester | 3-(thiophen-2-yl)quinoxalin-2-yloxy | dicyclopentyl phosphonate | tert-butyl |
| 200 | cyclopentyl ketone | 3-(thiophen-2-yl)quinoxalin-2-yloxy | dicyclopentyl phosphonate | tert-butyl |
| 201 | cyclopentyl amide | 3-(thiophen-2-yl)quinoxalin-2-yloxy | dicyclopentyl phosphonate | tert-butyl |
| 202 | thiophene-2-sulfonyl | 3-(thiophen-2-yl)quinoxalin-2-yloxy | dicyclopentyl phosphonate | tert-butyl |
| 203 | cyclopentyl sulfamoyl | 3-(thiophen-2-yl)quinoxalin-2-yloxy | dicyclopentyl phosphonate | tert-butyl |

TABLE 4-continued
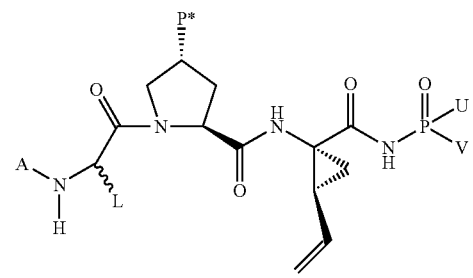
VIII
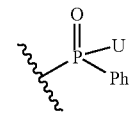
| Example # | A | P* | L |
|---|---|---|---|
| 204 | 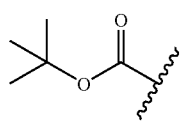 | 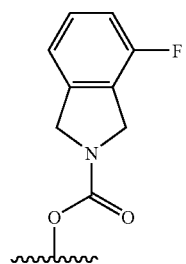 | 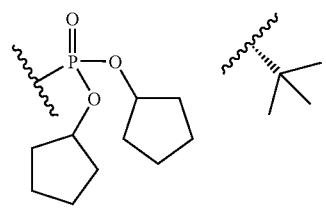 |
| 205 | 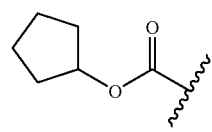 | 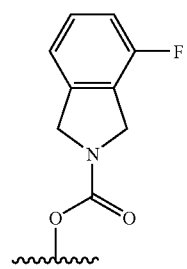 | 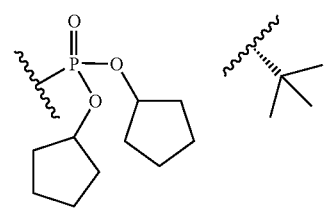 |
| 206 | 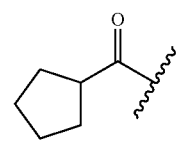 | 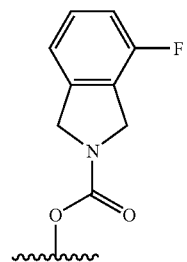 | 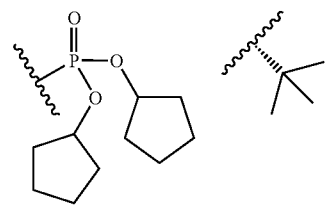 |
| 207 | 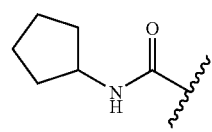 | 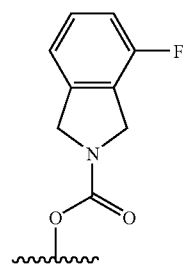 | 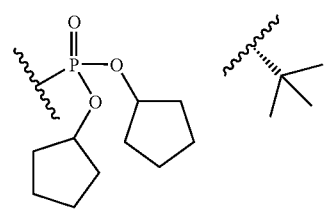 |

TABLE 4-continued

TABLE 4-continued
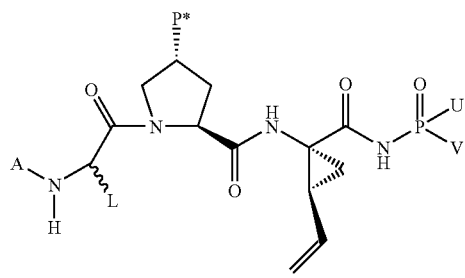
| Example # | A | P* | 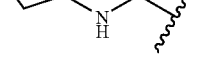 | L |
|---|---|---|---|---|
| 213 | | | | |
| 214 | | | | |
| 215 | | | | |
| 216 | | | | |
| 217 | | | | |

TABLE 4-continued

VIII

| Example # | A | P* | (phosphorus group) | L |
|---|---|---|---|---|
| 218 | cyclopentyl-C(=O)- | 4-F isoindoline-2-carbonyloxy | 1,3,2-dioxaphospholane 2-oxide | tert-butyl |
| 219 | cyclopentyl-NH-C(=O)- | 4-F isoindoline-2-carbonyloxy | 1,3,2-dioxaphospholane 2-oxide | tert-butyl |
| 220 | 2-thienyl-SO₂- | 4-F isoindoline-2-carbonyloxy | 1,3,2-dioxaphospholane 2-oxide | tert-butyl |
| 221 | cyclopentyl-NH-SO₂- | 4-F isoindoline-2-carbonyloxy | 1,3,2-dioxaphospholane 2-oxide | tert-butyl |

TABLE 4-continued
VIII
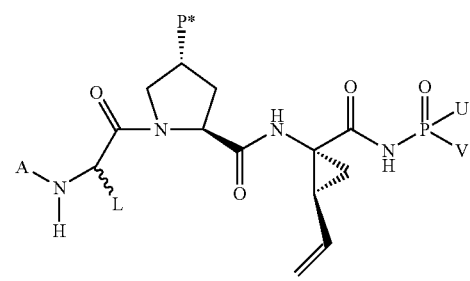
| Example # | A | P* |  | L |
|---|---|---|---|---|
| 222 | | | | |
| 223 | | | | |
| 224 | | | | |
| 225 | | | | |
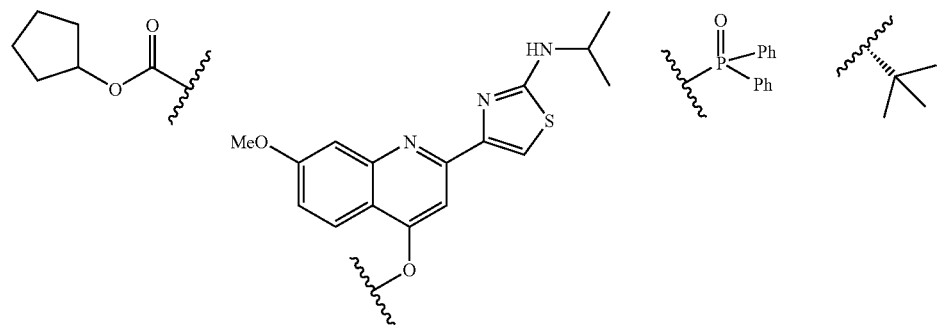
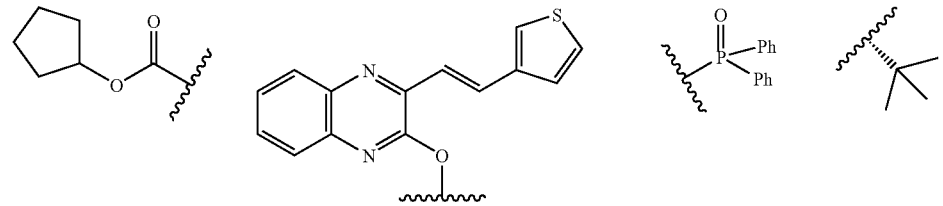
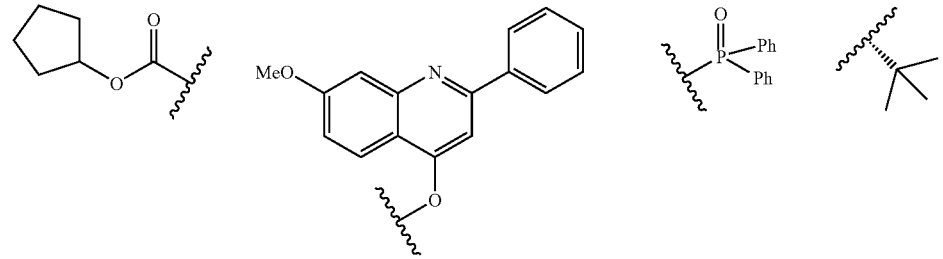
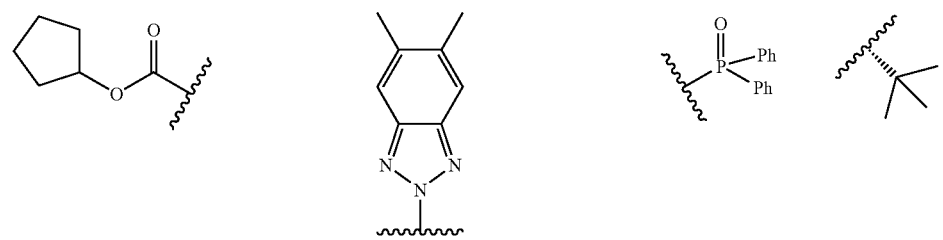

TABLE 4-continued

| Example # | A | P* | L |
|---|---|---|---|
| 226 | (cyclopentyl ester group) | (4-methoxyphenyl tetrazole group) | (tert-butyl group), U = Ph, V = Ph |

The compounds of the present invention exhibit potent inhibitory properties against the HCV NS3 protease. The following examples describe assays in which the compounds of the present invention can be tested for anti-HCV effects.

Example 227

NS3/NS4a Protease Enzyme Assay

HCV protease activity and inhibition is assayed using an internally quenched fluorogenic substrate. A DABCYL and an EDANS group are attached to opposite ends of a short peptide. Quenching of the EDANS fluorescence by the DABCYL group is relieved upon proteolytic cleavage. Fluorescence is measured with a Molecular Devices Fluoromax (or equivalent) using an excitation wavelength of 355 nm and an emission wavelength of 485 nm.

The assay is run in Corning white half-area 96-well plates (VWR 29444-312 [Corning 3693]) with full-length NS3 HCV protease 1b tethered with NS4A cofactor (final enzyme concentration 1 to 15 nM). The assay buffer is complemented with 10 μM NS4A cofactor Pep 4A (Anaspec 25336 or in-house, MW 1424.8). RET S1 (Ac-Asp-Glu-Asp(EDANS)-Glu-Glu-Abu-[COO]Ala-Ser-Lys-(DABCYL)-NH$_2$, (SEQ ID NO:4) AnaSpec 22991, MW 1548.6) is used as the fluorogenic peptide substrate. The assay buffer contains 50 mM Hepes at pH 7.5, 30 mM NaCl and 10 mM BME. The enzyme reaction is followed over a 30 minutes time course at room temperature in the absence and presence of inhibitors.

The peptide inhibitors HCV Inh 1 (Anaspec 25345, MW 796.8) Ac-Asp-Glu-Met-Glu-Glu-Cys-OH, (SEQ ID NO: 5) [−20° C.] and HCV Inh 2 (Anaspec 25346, MW 913.1) Ac-Asp-Glu-Dif-Cha-Cys-OH, (SEQ ID NO: 6) are used as reference compounds.

IC50 values are calculated using XLFit in ActivityBase (IDBS) using equation 205: $y=A+((B-A)/(1+((C/x)^D)))$.

Example 228

Cell-Based Replicon Assay

Quantification of HCV replicon RNA in cell lines (HCV Cell Based Assay) Cell lines, including Huh-11-7 or Huh 9-13, harboring HCV replicons (Lohmann, et al Science 285: 110-113, 1999) are seeded at $5 \times 10^3$ cells/well in 96 well plates and fed media containing DMEM (high glucose), 10% fetal calf serum, penicillin-streptomycin and non-essential amino acids. Cells are incubated in a 7.5% $CO_2$ incubator at 37° C. At the end of the incubation period, total RNA is extracted and purified from cells using Qiagen Rneasy 96 Kit (Catalog No. 74182). To amplify the HCV RNA so that sufficient material can be detected by an HCV specific probe (below), primers specific for HCV (below) mediate both the reverse transcription of the HCV RNA and the amplification of the cDNA by polymerase chain reaction (PCR) using the TaqMan One-Step RT-PCR Master Mix Kit (Applied Biosystems catalog no. 4309169). The nucleotide sequences of the RT-PCR primers, which are located in the NS5B region of the HCV genome, are the following:

```
HCV Forward primer "RBNS5bfor"
5'GCTGCGGCCTGTCGAGCT:      (SEQ ID NO: 1)

HCV Reverse primer "RBNS5Brev"
5'CAAGGTCGTCTCCGCATAC.     (SEQ ID NO 2)
```

Detection of the RT-PCR product is accomplished using the Applied Biosystems (ABI) Prism 7500 Sequence Detection System (SDS) that detects the fluorescence that is emitted when the probe, which is labeled with a fluorescence reporter dye and a quencher dye, is processed during the PCR reaction. The increase in the amount of fluorescence is measured during each cycle of PCR and reflects the increasing amount of RT-PCR product. Specifically, quantification is based on the threshold cycle, where the amplification plot crosses a defined fluorescence threshold. Comparison of the threshold cycles of the sample with a known standard provides a highly sensitive measure of relative template concentration in different samples (ABI User Bulletin #2 Dec. 11, 1997). The data is analyzed using the ABI SDS program version 1.7. The relative template concentration can be converted to RNA copy numbers by employing a standard curve of HCV RNA standards with known copy number (ABI User Bulletin #2 Dec. 11, 1997).

The RT-PCR product was detected using the following labeled probe:

```
5' FAM-CGAAGCTCCAGGACTGCACGATGCT-   (SEQ ID NO: 3)
TAMRA

FAM = Fluorescence reporter dye.

TAMRA: = Quencher dye.
```

The RT reaction is performed at 48° C. for 30 minutes followed by PCR. Thermal cycler parameters used for the PCR reaction on the ABI Prism 7500 Sequence Detection System are: one cycle at 95° C., 10 minutes followed by 40 cycles each of which include one incubation at 95° C. for 15 seconds and a second incubation for 60° C. for 1 minute.

To normalize the data to an internal control molecule within the cellular RNA, RT-PCR is performed on the cellular messenger RNA glyceraldehydes-3-phosphate dehydrogenase (GAPDH). The GAPDH copy number is very stable in the cell lines used. GAPDH RT-PCR is performed on the same exact RNA sample from which the HCV copy number is determined. The GAPDH primers and probes, as well as the standards with which to determine copy number, are contained in the ABI Pre-Developed TaqMan Assay Kit (catalog no. 4310884E). The ratio of HCV/GAPDH RNA is used to calculate the activity of compounds evaluated for inhibition of HCV RNA replication.

Activity of Compounds as Inhibitors of HCV Replication (Cell Based Assay) in Replicon Containing Huh-7 Cell Lines The effect of a specific anti-viral compound on HCV replicon RNA levels in Huh-11-7 or 9-13 cells is determined by comparing the amount of HCV RNA normalized to GAPDH (e.g. the ratio of HCV/GAPDH) in the cells exposed to compound versus cells exposed to the 0% inhibition and the 100% inhibition controls. Specifically, cells are seeded at $5 \times 10^3$ cells/well in a 96 well plate and are incubated either with: 1) media containing 1% DMSO (0% inhibition control), 2) 100 international units, IU/ml Interferon-alpha 2b in media/1% DMSO or 3) media/1% DMSO containing a fixed concentration of compound. 96 well plates as described above are then incubated at 37° C. for 3 days (primary screening assay) or 4 days (IC50 determination). Percent inhibition is defined as:

$$\% \text{ Inhibition} = [100 - ((S - C2)/C1 - C2))] \times 100$$

where

S=the ratio of HCV RNA copy number/GAPDH RNA copy number in the sample;

C1=the ratio of HCV RNA copy number/GAPDH RNA copy number in the 0% inhibition control (media/1% DMSO); and C2=the ratio of HCV RNA copy number/GAPDH RNA copy number in the 100% inhibition control (100 IU/ml Interferon-alpha 2b).

The dose-response curve of the inhibitor is generated by adding compound in serial, three-fold dilutions over three logs to wells starting with the highest concentration of a specific compound at 10 uM and ending with the lowest concentration of 0.01 uM. Further dilution series (1 uM to 0.001 uM for example) is performed if the IC50 value is not in the linear range of the curve. IC50 is determined based on the IDBS Activity Base program using Microsoft Excel "XL Fit" in which A=100% inhibition value (100 IU/ml Interferon-alpha 2b), B=0% inhibition control value (media/% DMSO) and C=midpoint of the curve as defined as C=(B−A/2)+A. A, B and C values are expressed as the ratio of HCV RNA/GAPDH RNA as determined for each sample in each well of a 96 well plate as described above. For each plate the average of 4-6 wells are used to define the 100% and 0% inhibition values.

In the above assays, representative compounds are found to have activity.

Although the invention has been described with respect to various preferred embodiments, it is not intended to be limited thereto, but rather those skilled in the art will recognize that variations and modifications may be made therein which are within the spirit of the invention and the scope of the appended claims.

What is claimed:
1. A compound represented by Formula III or Formula IV:

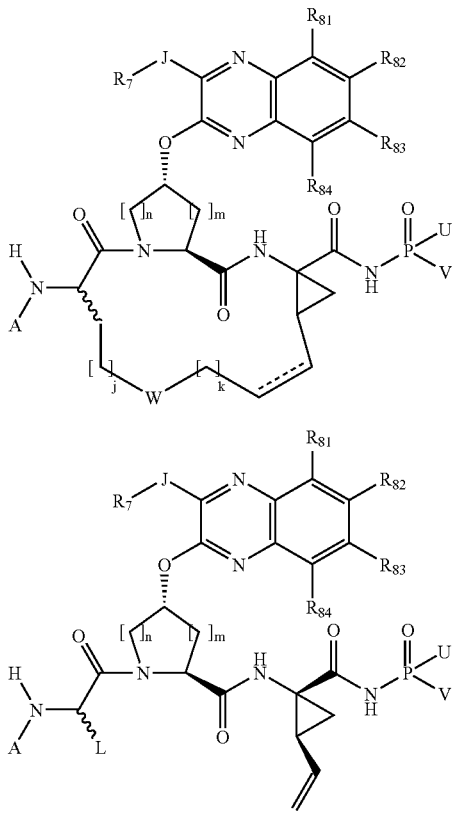

or a pharmaceutically acceptable salt, ester, or prodrug thereof;
wherein
A is selected from —(C═O)—O—$R_1$, —(C═O)—$R_2$, —C(═O)—NH—$R_2$, —S(O)$_2$—$R_1$, and —S(O)$_2$NH$R_2$;
$R_1$ is selected from the group consisting of:
(i) aryl;
(ii) substituted aryl;
(iii) heteroaryl;
(iv) substituted heteroaryl;
(v) heterocycloalkyl;
(vi) substituted heterocycloalkyl;
(vii) —$C_1$-$C_8$ alkyl;
(viii) —$C_2$-$C_8$ alkenyl;
(ix) —$C_2$-$C_8$ alkynyl containing 0, 1, 2, or 3 heteroatoms selected from O, S, or N;
(x) substituted —$C_1$-$C_8$ alkyl;
(xi) substituted —$C_2$-$C_8$ alkenyl;
(xii) substituted —$C_2$-$C_8$ alkynyl containing 0, 1, 2, or 3 heteroatoms selected from O, S or N;
(xiii) —$C_3$-$C_{12}$ cycloalkyl;
(xiv) substituted —$C_3$-$C_{12}$ cycloalkyl;
(xv) —$C_3$-$C_{12}$ cycloalkenyl; and
(xvi) substituted —$C_3$-$C_{12}$ cycloalkenyl;
$R_2$ is selected from the group consisting of:
(i) hydrogen;
(ii) aryl;
(iii) substituted aryl;
(iv) heteroaryl;
(v) substituted heteroaryl;
(vi) heterocycloalkyl;
(vii) substituted heterocycloalkyl;
(viii) —$C_1$-$C_8$ alkyl;
(ix) —$C_2$-$C_8$ alkenyl;
(x) —$C_2$-$C_8$ alkynyl containing 0, 1, 2, or 3 heteroatoms selected from O, S, or N;
(xi) substituted —$C_1$-$C_8$ alkyl;
(xii) substituted —$C_2$-$C_8$ alkenyl;
(xiii) substituted —$C_2$-$C_8$ alkynyl containing 0, 1, 2, or 3 heteroatoms selected from O, S or N;
(xiv) —$C_3$-$C_{12}$ cycloalkyl;
(xv) substituted —$C_3$-$C_{12}$ cycloalkyl;
(xvi) —$C_3$-$C_{12}$ cycloalkenyl; and
(xvii) substituted -$C_3$-$C_{12}$ cycloalkenyl;
L is selected from the group consisting of:
(i) —$C_1$-$C_8$ alkyl;
(ii) —$C_2$-$C_8$ alkenyl;
(iii) —$C_2$-$C_8$ alkynyl containing 0, 1, 2, or 3 heteroatoms selected from O, S or N;
(iv) substituted —$C_1$-$C_8$ alkyl;
(v) substituted —$C_2$-$C_8$ alkenyl;
(vi) substituted —$C_2$-$C_8$ alkynyl containing 0, 1, 2, or 3 heteroatoms selected from O, S or N;
(vii) —$C_3$-$C_{12}$ cycloalkyl;
(viii) substituted —$C_3$-$C_{12}$ cycloalkyl;
(ix) —$C_3$-$C_{12}$ cycloalkenyl;
(x) substituted —$C_3$-$C_{12}$ cycloalkenyl;
(xi) heterocyclic;
(xii) substituted heterocyclic;
(xiii) aryl; and
(xiv) substituted aryl;
W is selected from —$CH_2$—, —O—, —S—, —S(O)$_2$, —CO—, —C(O)O—, —C(O)NH—, —CHF—, —$CF_2$—, aryl, substituted aryl, heteroaryl, and substituted heteroaryl;
U and V are independently chosen from the following groups:
(i) $R_5$; and
(ii) $XR_6$; or, in the alternative, U and V taken together with the phosphorus atom to which they are attached form a phosphorus-derived heterocyclic moiety;
$R_5$ is selected from the group consisting of:
(i) aryl;
(ii) substituted aryl;
(iii) heteroaryl;
(iv) substituted heteroaryl;
(v) heterocycloalkyl;
(vi) substituted heterocycloalkyl;
(vii) —$C_1$-$C_8$ alkyl;
(viii) —$C_2$-$C_8$ alkenyl;
(ix) —$C_2$-$C_8$ alkynyl containing 0, 1, 2, or 3 heteroatoms selected from O, S, or N;
(x) substituted —$C_1$-$C_8$ alkyl;
(xi) substituted —$C_2$-$C_8$ alkenyl;
(xii) substituted —$C_2$-$C_8$ alkynyl containing 0, 1, 2, or 3 heteroatoms selected from O, S or N;
(xiii) —$C_3$-$C_{12}$ cycloalkyl;
(xiv) substituted —$C_3$-$C_{12}$ cycloalkyl;
(xv) —$C_3$-$C_{12}$ cycloalkenyl; and
(xvi) substituted —$C_3$-$C_{12}$ cycloalkenyl;
$R_6$ is selected from the group consisting of:
(i) hydrogen;
(ii) aryl;
(iii) substituted aryl;
(iv) heteroaryl;
(v) substituted heteroaryl;
(vi) heterocycloalkyl;
(vii) substituted heterocycloalkyl;
(viii) —$C_1$-$C_8$ alkyl;

(ix) —$C_2$-$C_8$ alkenyl;
(x) —$C_2$-$C_8$ alkynyl containing 0, 1, 2, or 3 heteroatoms selected from O, S, or N;
(xi) substituted —$C_1$-$C_8$ alkyl;
(xii) substituted —$C_2$-$C_8$ alkenyl;
(xiii) substituted —$C_2$-$C_8$ alkynyl containing 0, 1, 2, or 3 heteroatoms selected from O, S or N;
(xiv) —$C_3$-$C_{12}$ cycloalkyl;
(xv) substituted —$C_3$-$C_{12}$ cycloalkyl;
(xvi) —$C_3$-$C_{12}$ cycloalkenyl; and
(xvii) substituted —$C_3$-$C_{12}$ cycloalkenyl;
X is absent or is selected from the group consisting of:
(i) O;
(ii) S; and
(iii) $NR_3$;
J is absent, O, S, $NR_5$, CO, (CO)$NR_5$, (CO)O, $NR_5$(CO), NH(CO)NH or $NR_5SO_2$;
$R_7$ is selected from aryl, substituted aryl, heteroaryl, and substituted heteroaryl;
$R_{81}$, $R_{82}$, $R_{83}$, and $R_{84}$ are independently selected from:
(i) hydrogen;
(ii) halogen;
(iii) —$NO_2$;
(iv) —CN;
(v) $MR_9$, wherein M is absent O, S or $NR_3R_6$;
(vi) aryl;
(vii) substituted aryl;
(viii) heteroaryl;
(ix) substituted heteroaryl;
(x) heterocycloalkyl; and
(xi) substituted heterocycloalkyl;
$R_9$ is selected from the group consisting of:
(i) hydrogen;
(ii) aryl;
(iii) substituted aryl;
(iv) heteroaryl;
(v) substituted heteroaryl;
(vi) heterocycloalkyl;
(vii) substituted heterocycloalkyl;
(viii) —$C_1$-$C_8$ alkyl;
(ix) —$C_2$-$C_8$ alkenyl;
(x) —$C_2$-$C_8$ alkynyl containing 0, 1, 2, or 3 heteroatoms selected from O, S, or N;
(xi) substituted —$C_1$-$C_8$ alkyl;
(xii) substituted —$C_2$-$C_8$ alkenyl; and
(xiii) substituted —$C_2$-$C_8$ alkynyl containing 0, 1, 2, or 3 heteroatoms selected from O, S or N;
$R_3$ is selected from the group consisting of:
(i) hydrogen;
(ii) aryl;
(iii) substituted aryl;
(iv) heteroaryl;
(v) substituted heteroaryl;
(vi) heterocycloalkyl;
(vii) substituted heterocycloalkyl;
(viii) —$C_1$-$C_8$ alkyl;
(ix) —$C_2$-$C_8$ alkenyl;
(x) —$C_2$-$C_8$ alkynyl containing 0, 1, 2, or 3 heteroatoms selected from O, S, or N;
(xi) substituted —$C_1$-$C_8$ alkyl;
(xii) substituted —$C_2$-$C_8$ alkenyl;
(xiii) substituted —$C_2$-$C_8$ alkynyl containing 0, 1, 2, or 3 heteroatoms selected from O, S or N;
(xiv) —$C_3$-$C_{12}$ cycloalkyl;
(xv) substituted —$C_3$-$C_{12}$ cycloalkyl;
(xvi) —$C_3$-$C_{12}$ cycloalkenyl; and
(xvii) substituted —$C_3$-$C_{12}$ cycloalkenyl;
j is 0, 1, 2, 3, or 4;
k is 1, 2, or 3;
m is 0, 1, or 2; and
n is 1, 2, or 3.

2. A compound of Formula VII, or a pharmaceutically acceptable salt, ester, or prodrug thereof, wherein A, P* and

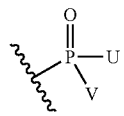

are delineated in Table 1:

TABLE 1

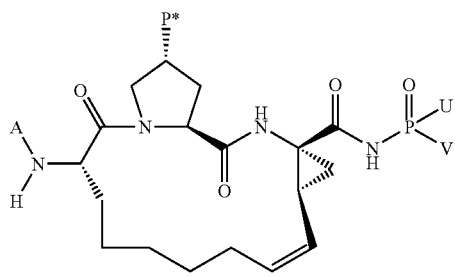

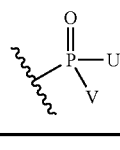

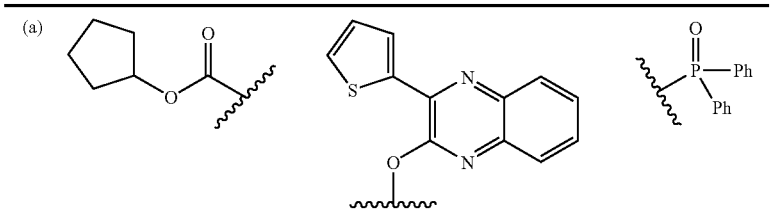

TABLE 1-continued
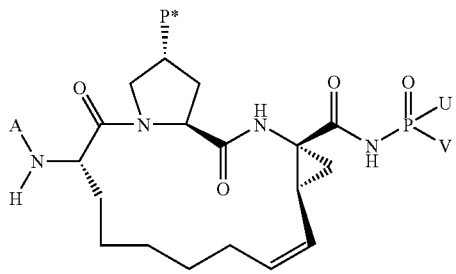
VII
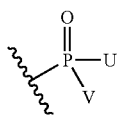
| | A | P* | |
|---|---|---|---|
| (b) | 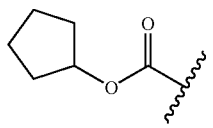 | 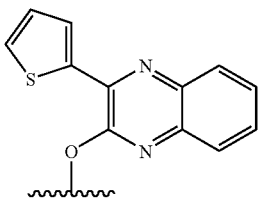 | 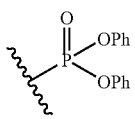 |
| (c) | 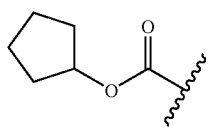 | 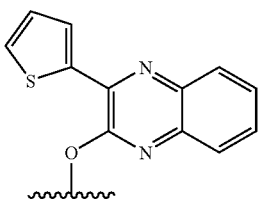 | 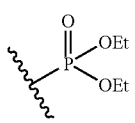 |
| (d) | 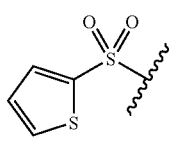 | 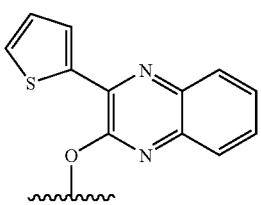 | 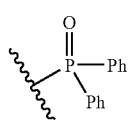 |
| (e) | 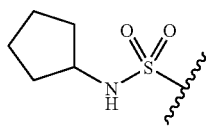 | 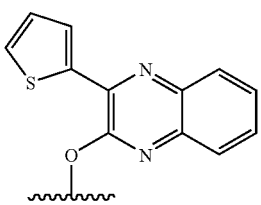 | 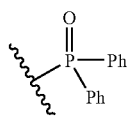 |
| (f) | 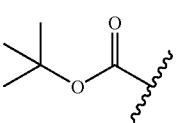 | 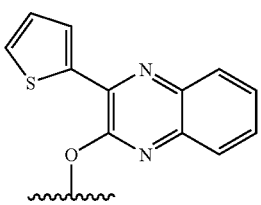 | 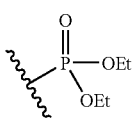 |

TABLE 1-continued
VII
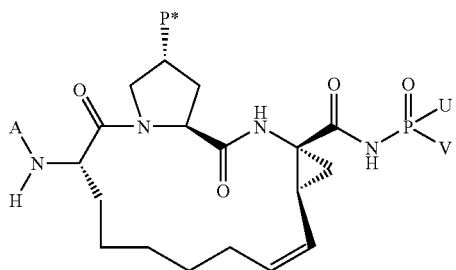
| | A | P* | 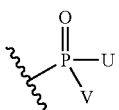 |
|---|---|---|---|
| (g) | 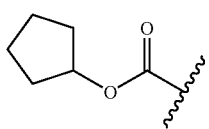 | 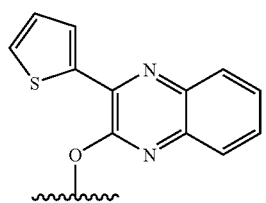 | 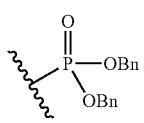 |
| (h) | 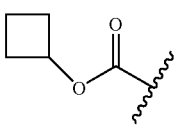 | 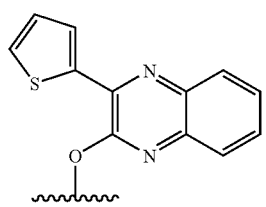 | 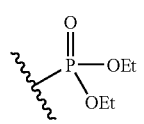 |
| (i) | 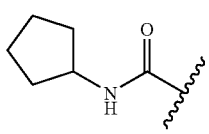 | 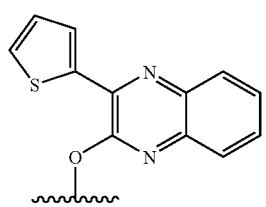 | 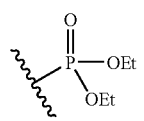 |
| (j) | 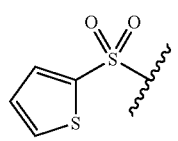 | 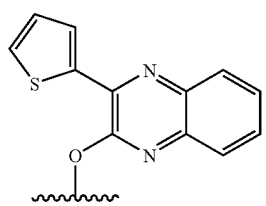 | 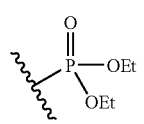 |
| (k) | 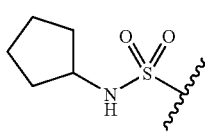 | 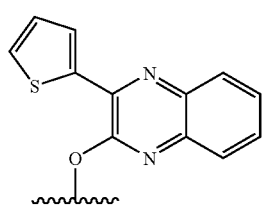 | 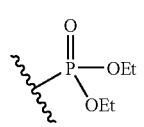 |

TABLE 1-continued
VII
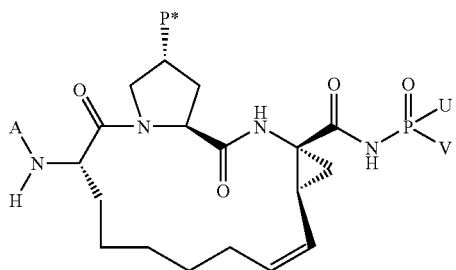
| | A | P* | 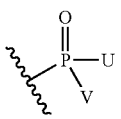 |
|---|---|---|---|
| (l) | 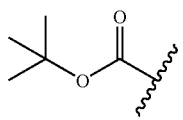 | 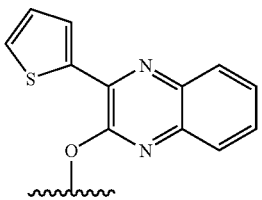 | 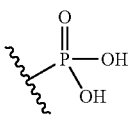 |
| (m) | 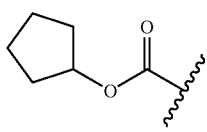 | 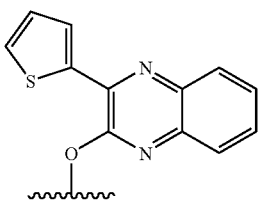 | 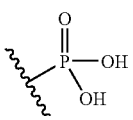 |
| (n) | 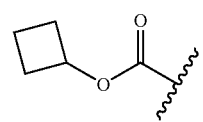 | 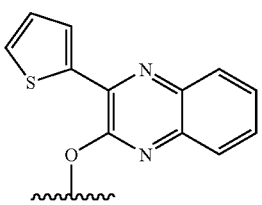 | 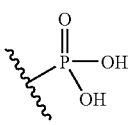 |
| (o) | 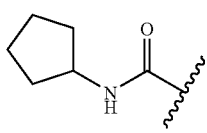 | 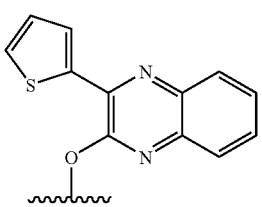 | 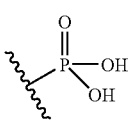 |
| (p) | 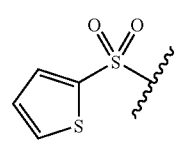 | 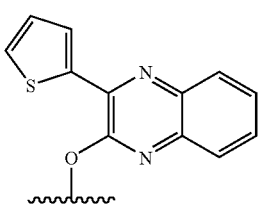 | 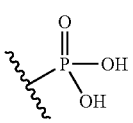 |

TABLE 1-continued
VII
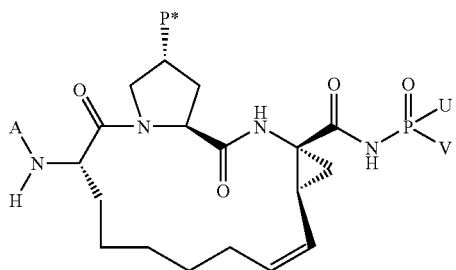
| | A | P* | 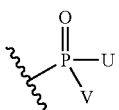 |
|---|---|---|---|
| (q) | 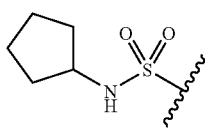 | 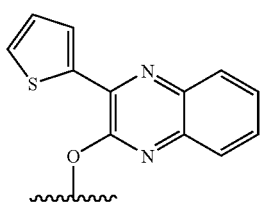 | 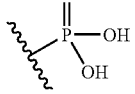 |
| (r) | 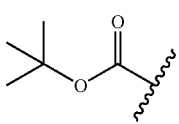 | 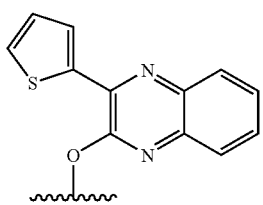 | 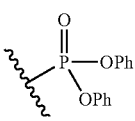 |
| (s) | 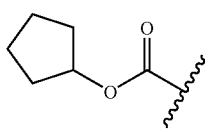 | 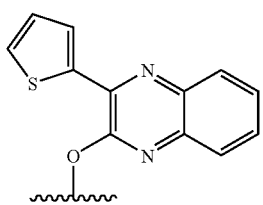 | 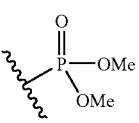 |
| (t) | 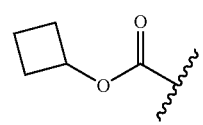 | 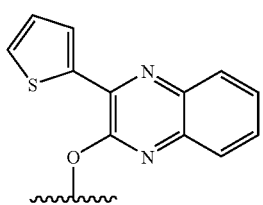 | 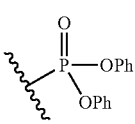 |
| (u) | 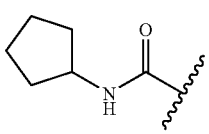 | 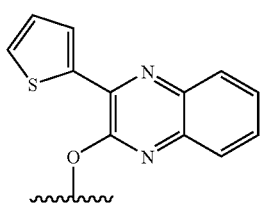 | 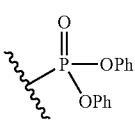 |

TABLE 1-continued
VII
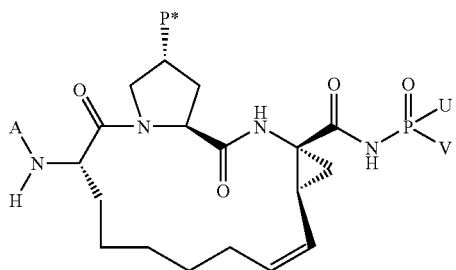
| | A | P* | 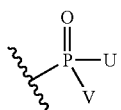 |
|---|---|---|---|
| (v) | 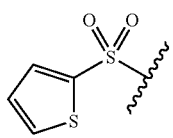 | 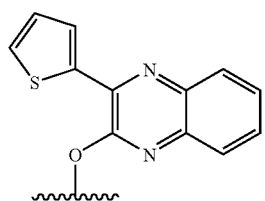 | 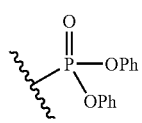 |
| (w) | 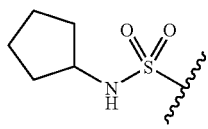 | 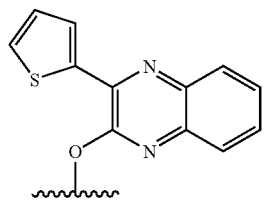 | 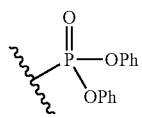 |
| (x) | 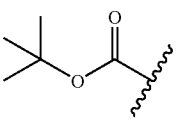 | 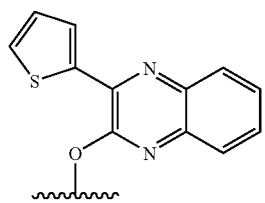 | 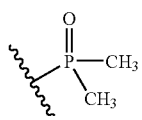 |
| (y) | 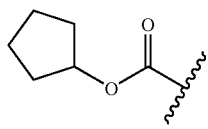 | 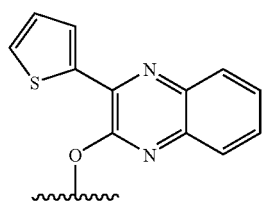 | 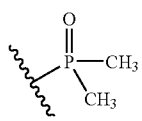 |
| (z) | 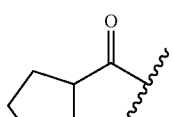 | 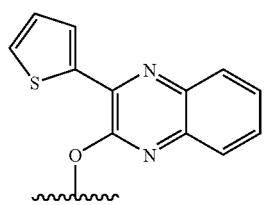 | 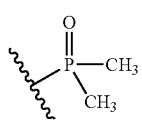 |

TABLE 1-continued
VII
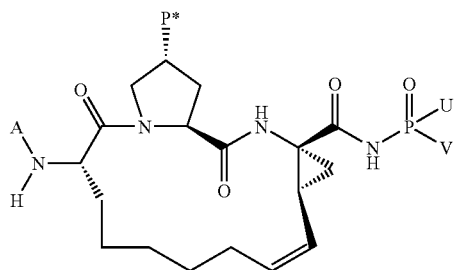
| A | P* | 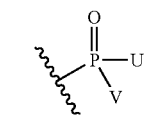 |
|---|---|---|
| (aa) 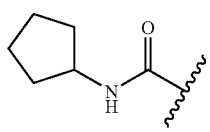 | 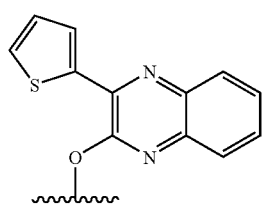 | 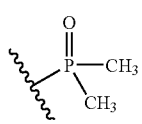 |
| (bb) 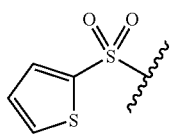 | 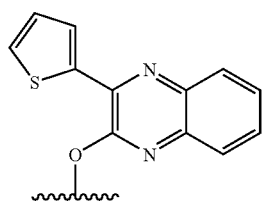 | 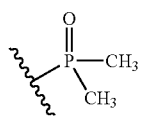 |
| (cc) 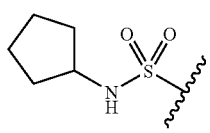 | 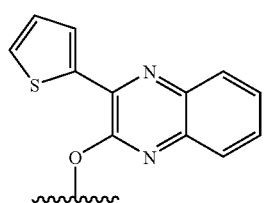 | 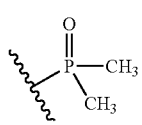 |
| (dd) 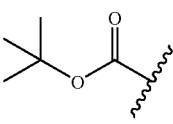 | 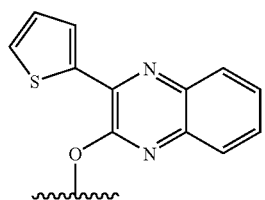 | 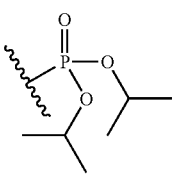 |
| (ee) 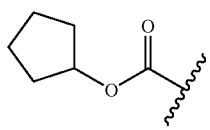 | 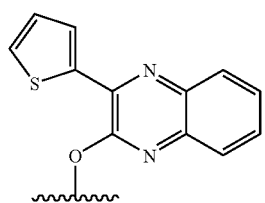 | 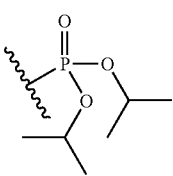 |

TABLE 1-continued
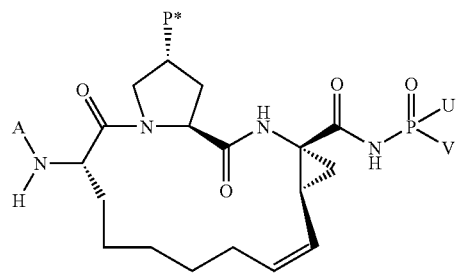
VII
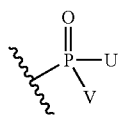
| | A | P* | |
|---|---|---|---|
| (ff) | 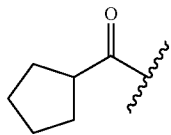 | 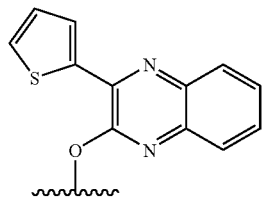 | 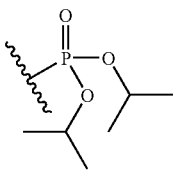 |
| (gg) | 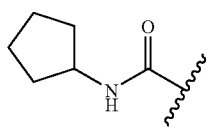 | 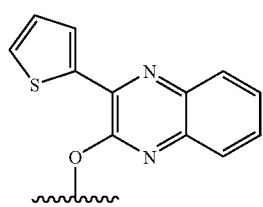 | 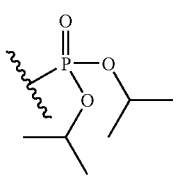 |
| (hh) | 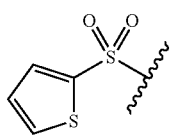 | 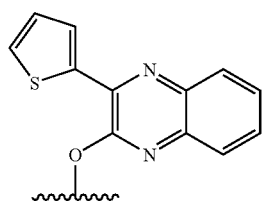 | 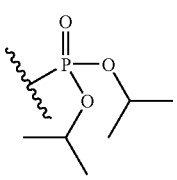 |
| (ii) | 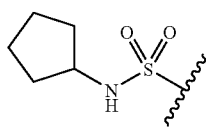 | 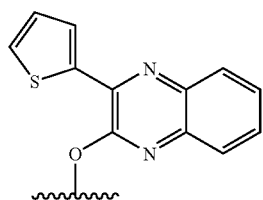 | 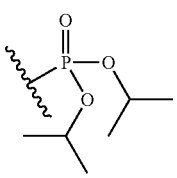 |
| (jj) | 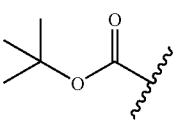 | 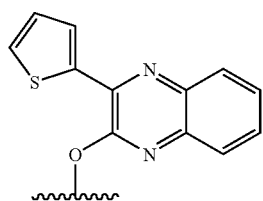 | 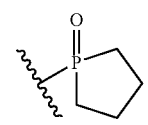 |

TABLE 1-continued
VII
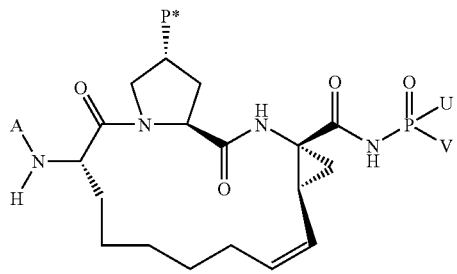
| | A | P* | 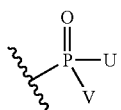 |
|---|---|---|---|
| (kk) | 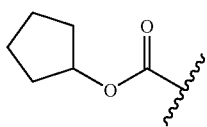 | 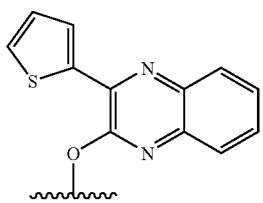 | 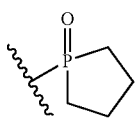 |
| (ll) | 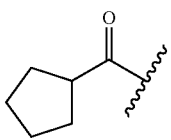 | 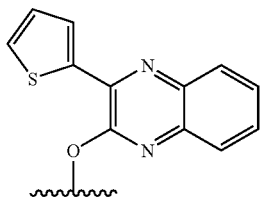 | 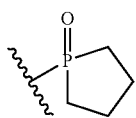 |
| (mm) | 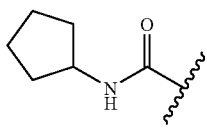 | 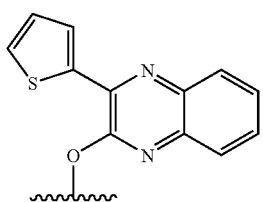 | 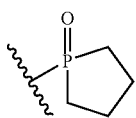 |
| (nn) | 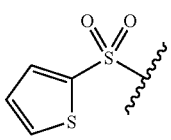 | 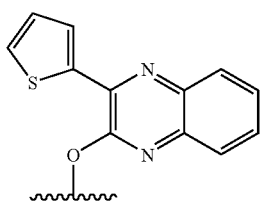 | 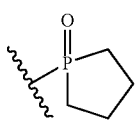 |
| (oo) | 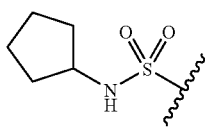 | 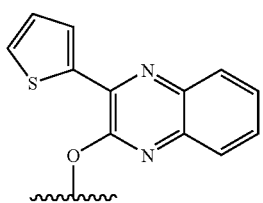 | 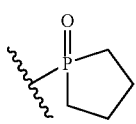 |

TABLE 1-continued
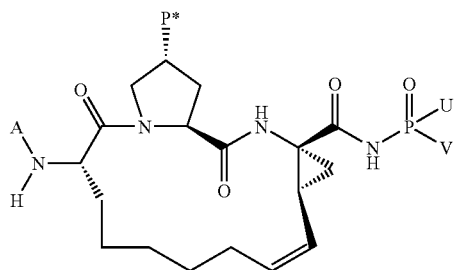
VII
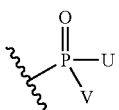
| | A | P* | |
|---|---|---|---|
| (pp) | 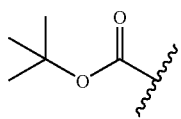 | 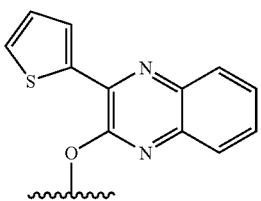 | 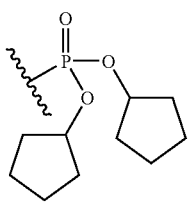 |
| (qq) | 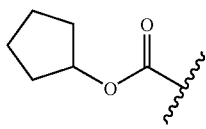 | 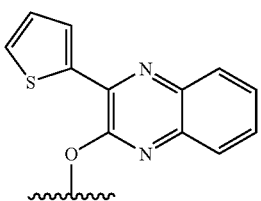 | 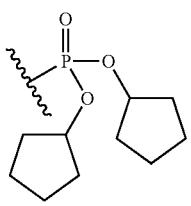 |
| (rr) | 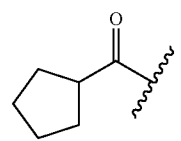 | 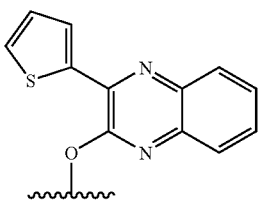 | 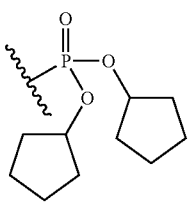 |
| (ss) | 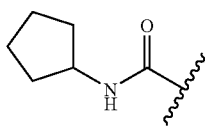 | 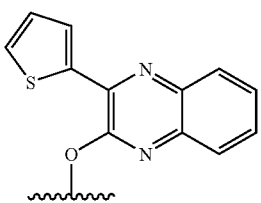 | 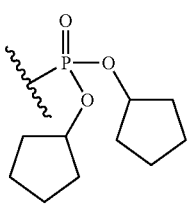 |
| (tt) | 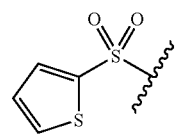 | 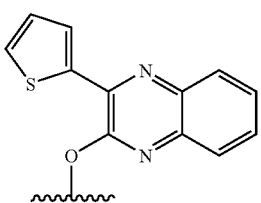 | 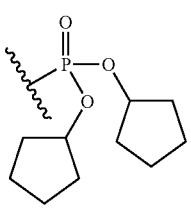 |

TABLE 1-continued
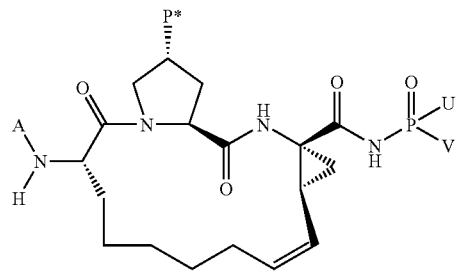
VII
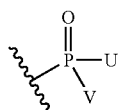
| A | P* | |
|---|---|---|
| (uu) 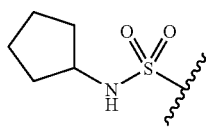 | 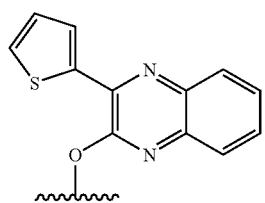 | 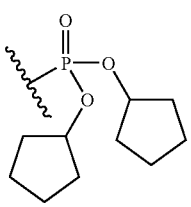 |
| (vv) 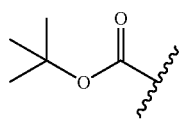 | 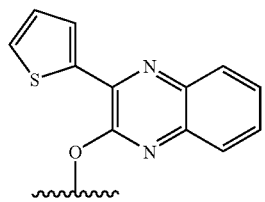 | 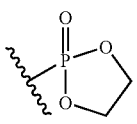 |
| (ww) 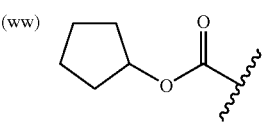 | 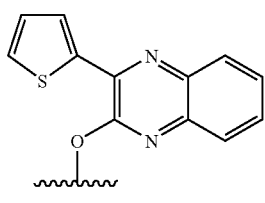 | 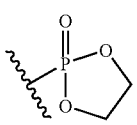 |

TABLE 1-continued
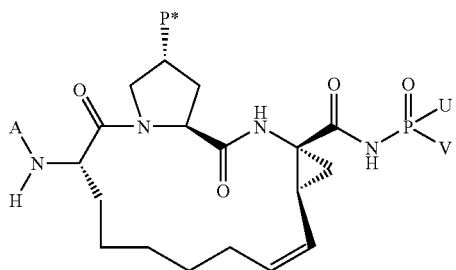
| A | P* | 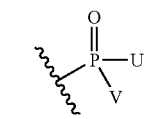 |
|---|---|---|
| (xx) 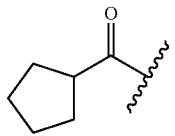 | 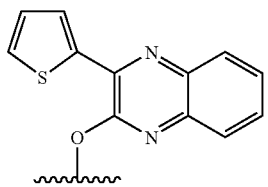 | 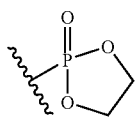 |
| (yy) 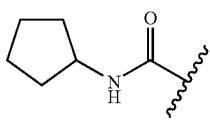 | 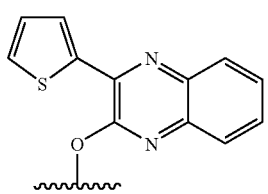 | 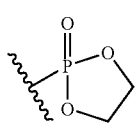 |
| (zz) 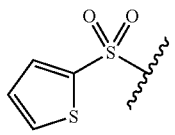 | 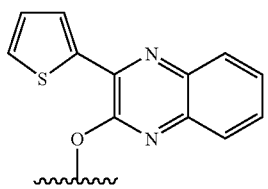 | 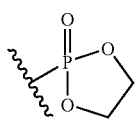 |
| (aaa) 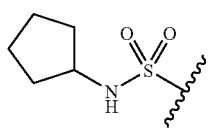 | 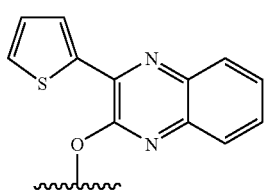 | 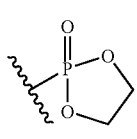 |
| (bbb) 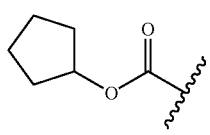 | 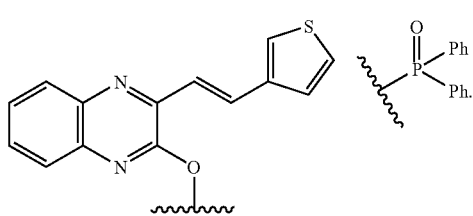 | |

3. A compound of Formula VIII, or a pharmaceutically acceptable salt, ester, or prodrug thereof, wherein A, P*,
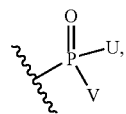
and L are delineated in Table 2:

TABLE 2-continued
VIII
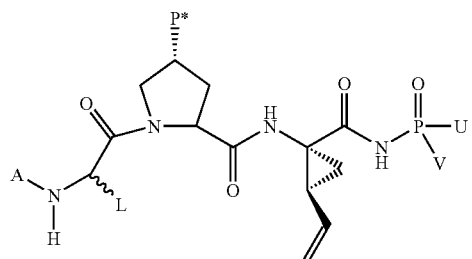
| A | P* | 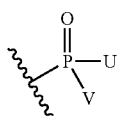 | L |
|---|---|---|---|
| (e) 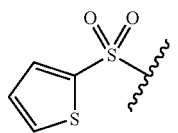 | 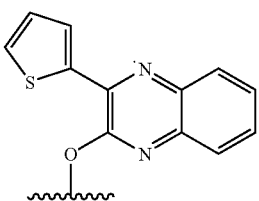 | 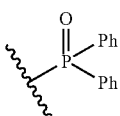 | 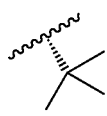 |
| (f) 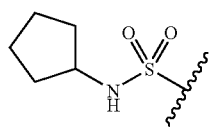 | 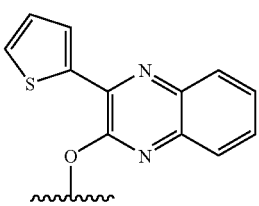 | 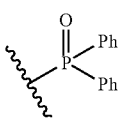 | 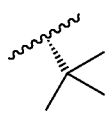 |
| (g) 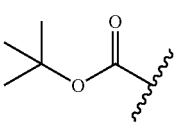 | 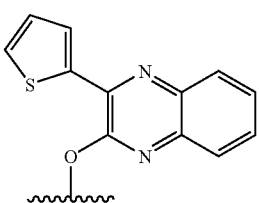 | 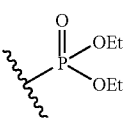 | 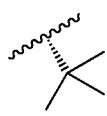 |
| (h) 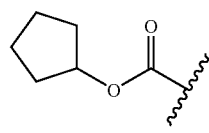 | 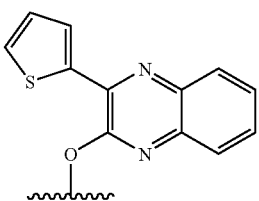 | 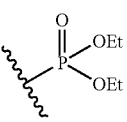 | 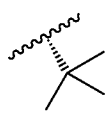 |
| (i) 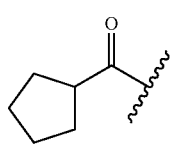 | 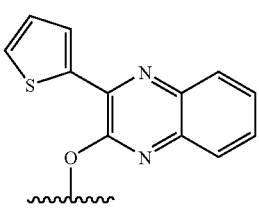 | 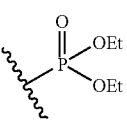 | 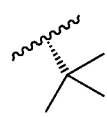 |

TABLE 2-continued
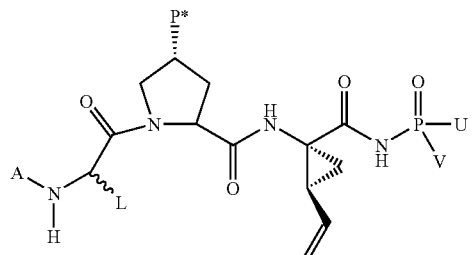
VIII
| | A | P* | 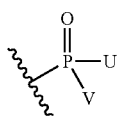 | L |
|---|---|---|---|---|
| (j) | 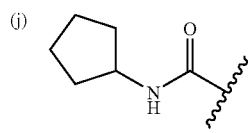 | 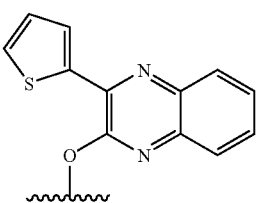 | 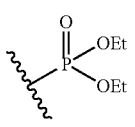 |  |
| (k) | 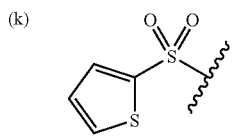 | 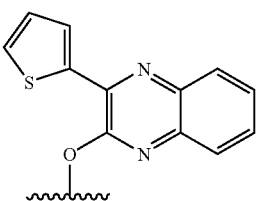 | 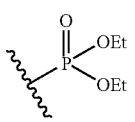 | 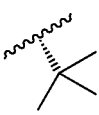 |
| (l) | 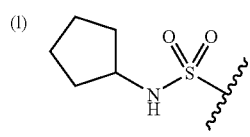 | 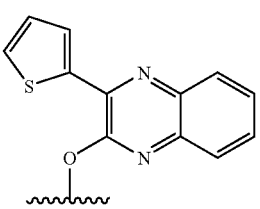 | 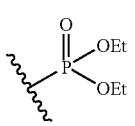 |  |
| (m) | 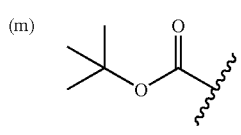 | 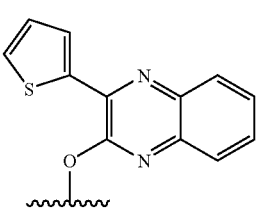 | 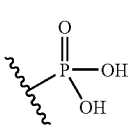 | 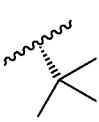 |
| (n) | 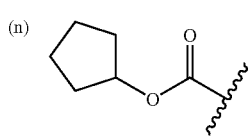 | 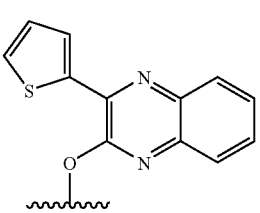 | 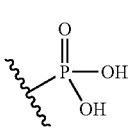 |  |

TABLE 2-continued
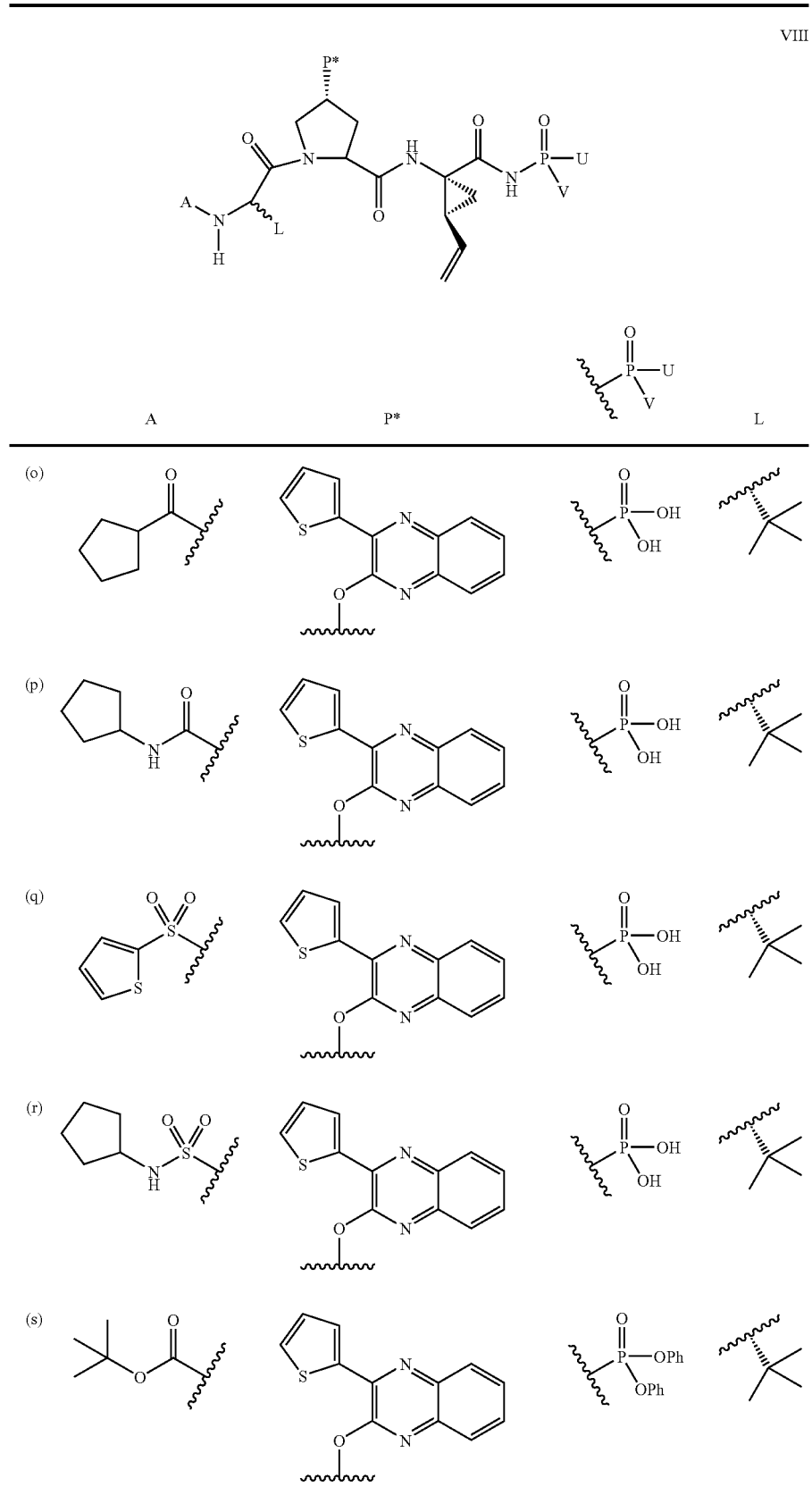

TABLE 2-continued
VIII
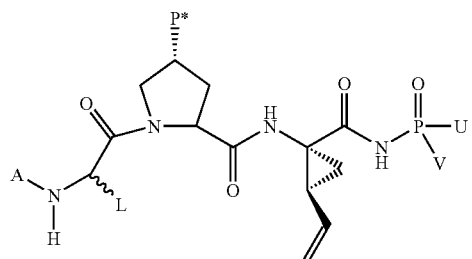
| A | P* | 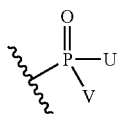 | L |
|---|---|---|---|
| (t) cyclopentyl ester | thiophene-quinoxaline-O | P(=O)(OPh)(OPh) | t-Bu |
| (u) cyclopentyl ketone | thiophene-quinoxaline-O | P(=O)(OPh)(OPh) | t-Bu |
| (v) cyclopentyl amide | thiophene-quinoxaline-O | P(=O)(OPh)(OPh) | t-Bu |
| (w) thiophene-sulfonyl | thiophene-quinoxaline-O | P(=O)(OPh)(OPh) | t-Bu |
| (x) cyclopentyl sulfonamide | thiophene-quinoxaline-O | P(=O)(OPh)(OPh) | t-Bu |

TABLE 2-continued
VIII
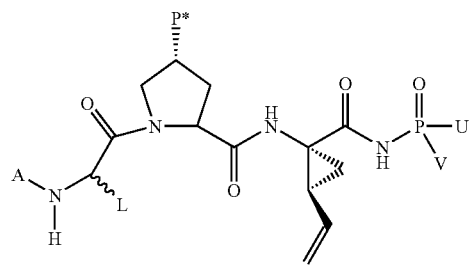
| | A | P* | 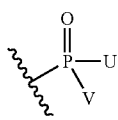 | L |
|---|---|---|---|---|
| (y) | | | | 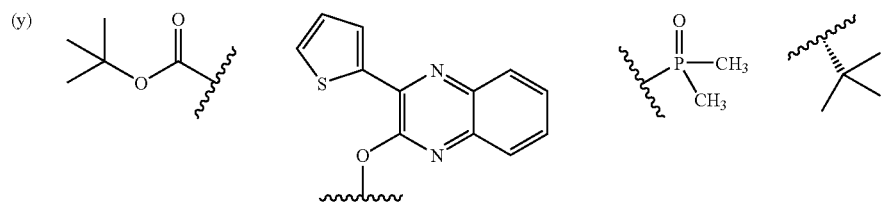 |
| (z) | | | | 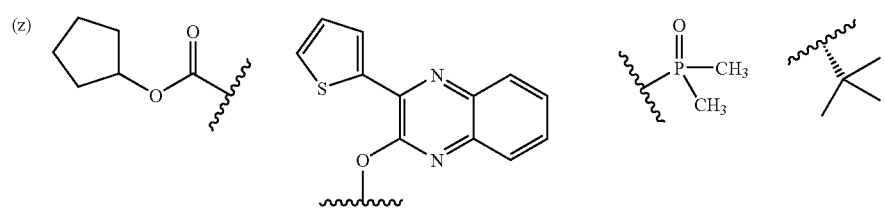 |
| (aa) | | | | 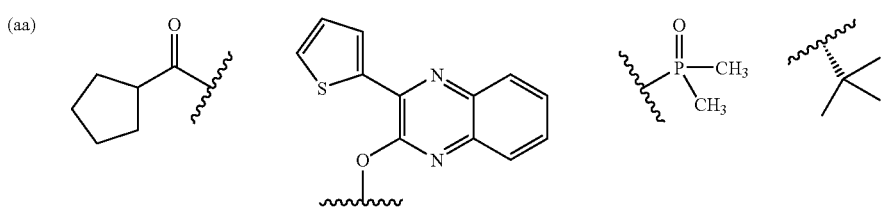 |
| (bb) | | | | 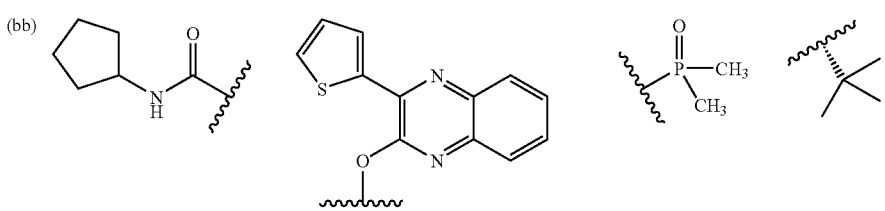 |
| (cc) | | | | 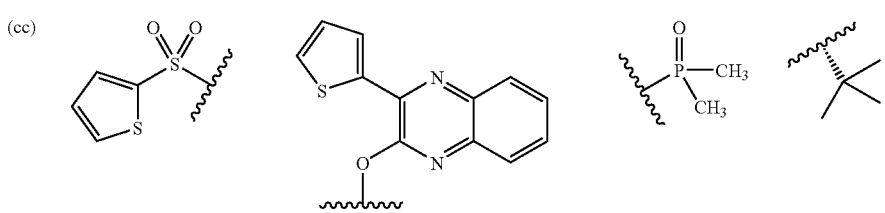 |

TABLE 2-continued
VIII
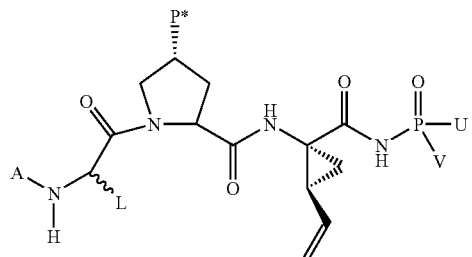
| | A | P* | 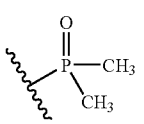 | L |
|---|---|---|---|---|
| (dd) | 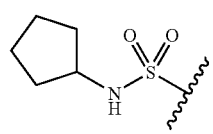 | 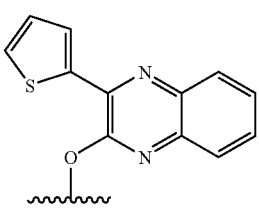 | 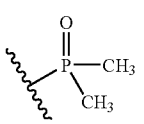 |  |
| (ee) | 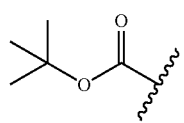 | 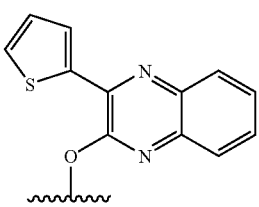 | 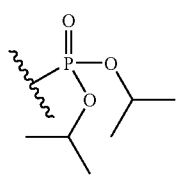 |  |
| (ff) | 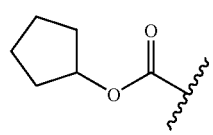 | 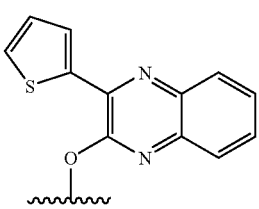 | 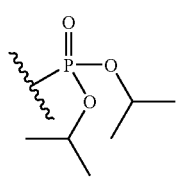 |  |
| (gg) | 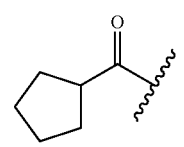 | 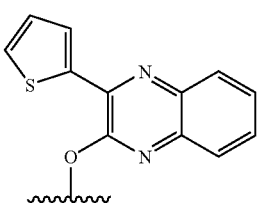 | 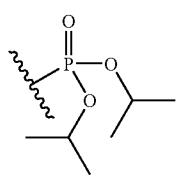 |  |
| (hh) | 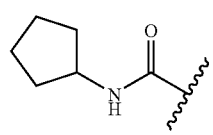 | 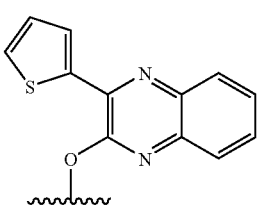 | 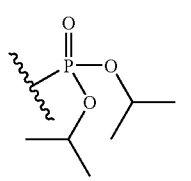 | 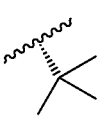 |

TABLE 2-continued

VIII

| A | P* | | L |
|---|---|---|---|
| (ii) | | | |
| (jj) | | | |
| (kk) | | | |
| (ll) | | | |
| (mm) | | | |

TABLE 2-continued

VIII

| A | P* | | L |
|---|---|---|---|
| (nn) | | | |
| (oo) | | | |
| (pp) | | | |
| (qq) | | | |
| (rr) | | | |

TABLE 2-continued
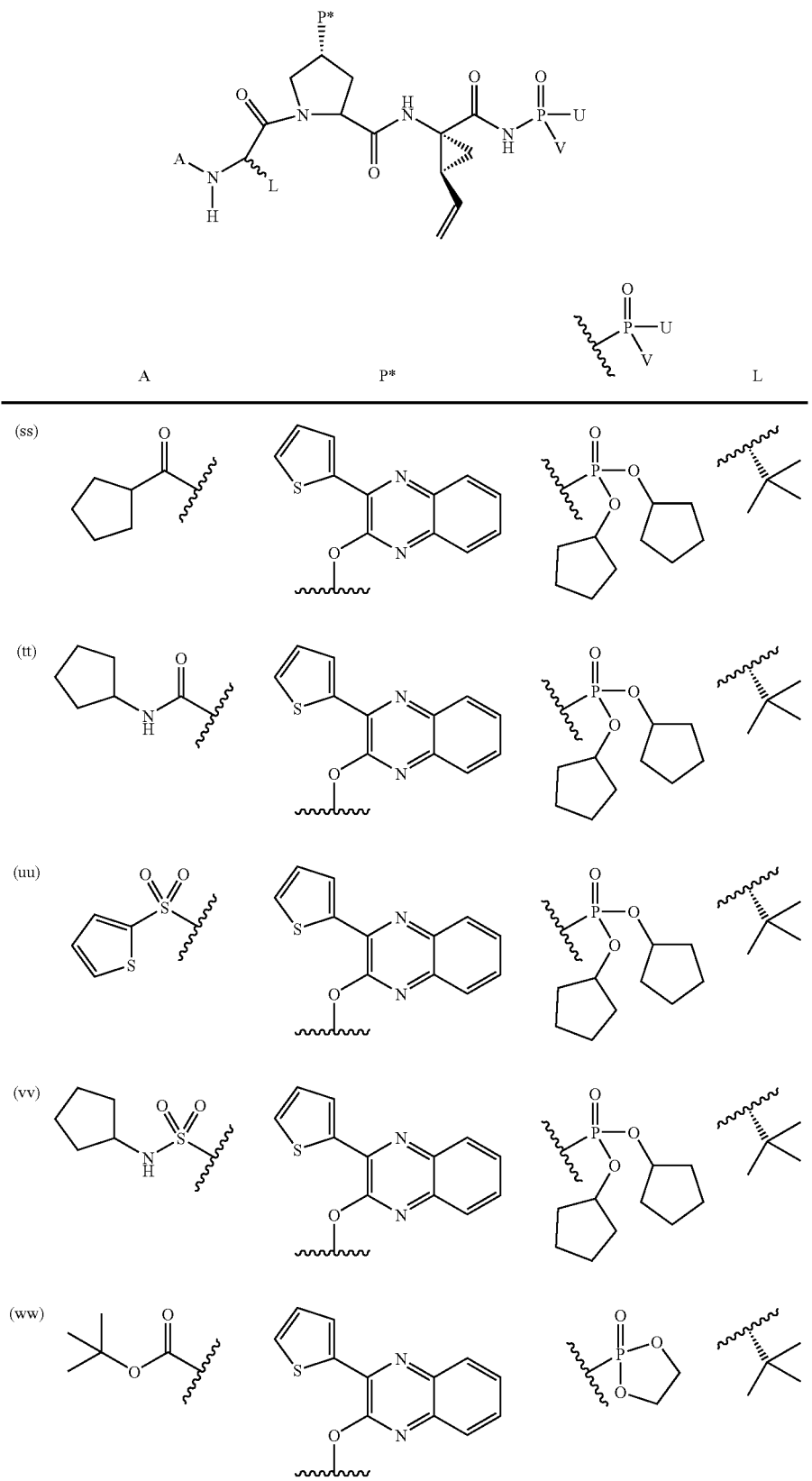

TABLE 2-continued
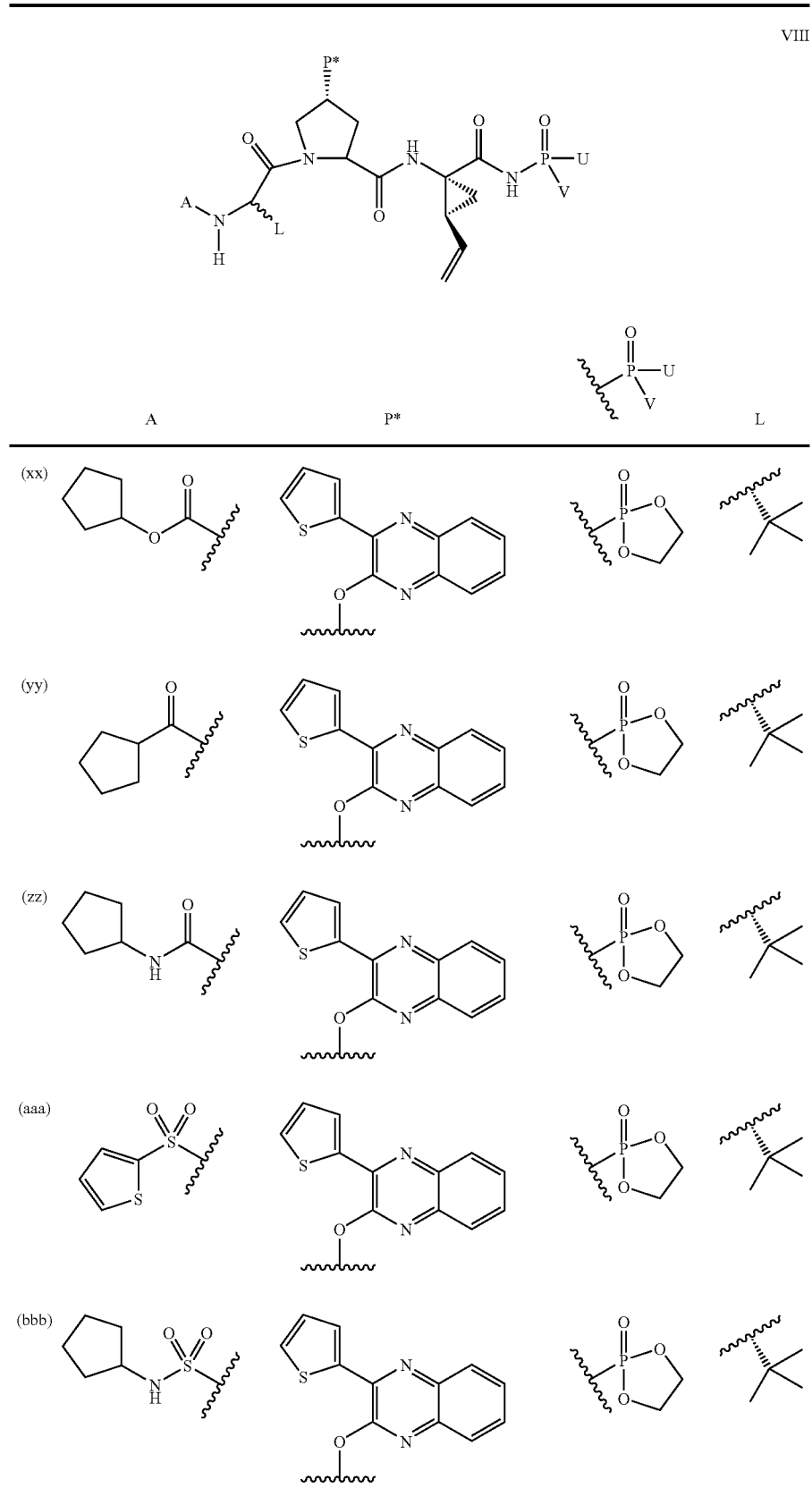

TABLE 2-continued

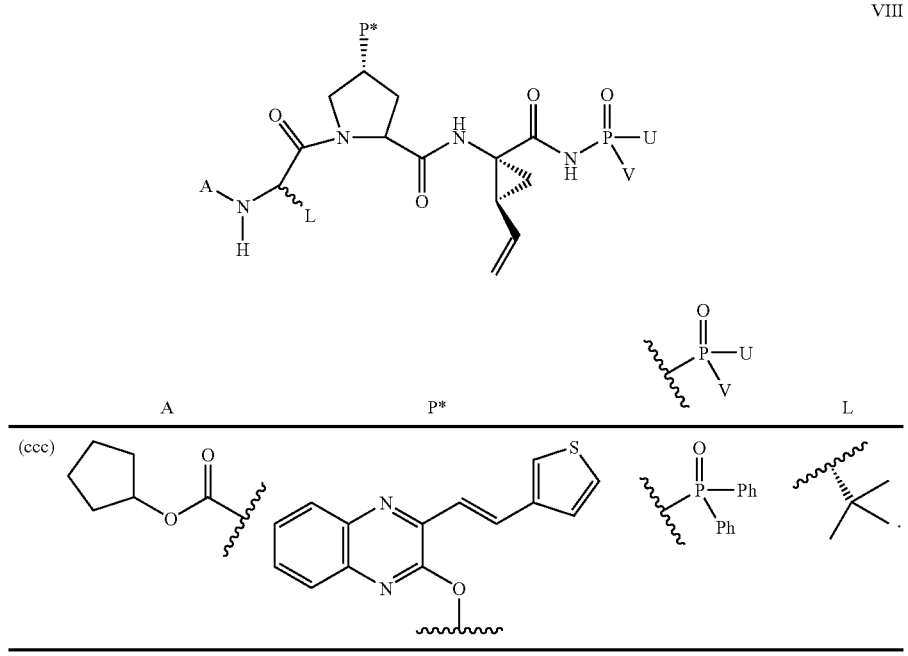

VIII

| A | P* | L |
|---|----|---|
| (ccc) cyclopentyl ester | quinoxaline-thiophene | P(O)Ph₂ or t-Bu |

4. A pharmaceutical composition comprising a therapeutically effective amount of a compound according to claims 1, or a pharmaceutically acceptable salt, ester, or prodrug thereof, alone, or in combination with a pharmaceutically acceptable carrier or excipient.

5. A method of treating a hepatitis C viral infection in a subject, comprising administering to the subject a pharmaceutical composition according to claim 4.

6. A method of inhibiting the replication of hepatitis C virus, the method comprising contacting the hepatitis C virus with an inhibitory amount of a compound of claim 1.

7. The method of claim 5 further comprising administering an additional anti-hepatitis C virus agent.

8. The method of claim 7, wherein said additional anti-hepatitis C virus agent is selected from the group consisting of: α-interferon, β-interferon, ribavarin, and adamantine.

9. The method of claim 7, wherein said additional anti-hepatitis C virus agent is an inhibitor of hepatitis C virus helicase, polymerase, metalloprotease, or IRES.

* * * * *

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Forward Primer

<400> SEQUENCE: 1
gctgcggcct gtcgagct                                                   18

<210> SEQ ID NO 2
<211> LENGTH: 19
<212> TYPE: DNA
<213> ORGANISM: Artificial Sequence
<220> FEATURE:
```

```
<223> OTHER INFORMATION: Reverse Primer

<400> SEQUENCE: 2
caaggtcgtc tccgcatac                                                    19

<210> SEQ ID NO 3
<211> LENGTH: 25
<212> TYPE: DNA
<213> ORGANISM: Artificial Sequence
<220> FEATURE:
<223> OTHER INFORMATION: Probe

<400> SEQUENCE: 3
cgaagctcca ggactgcacg atgct                                             25

<210> SEQ ID NO 4
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 6
<223> OTHER INFORMATION: Xaa = 2-aminobutyric acid

<400> SEQUENCE: 4

Asp Glu Asp Glu Glu Xaa Ala Ser Lys
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

Asp Glu Met Glu Glu Cys
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 3
<223> OTHER INFORMATION: Xaa = 3,3-diphenyl alanine
<220> FEATURE:
<221> NAME/KEY: VARIANT
<222> LOCATION: 4
<223> OTHER INFORMATION: Xaa = beta-cyclohexyl-alanine

<400> SEQUENCE: 6

Asp Glu Xaa Xaa Cys
1               5
```